United States Patent
(12) United States Patent
Royle et al.

(10) Patent No.: US 11,401,342 B2
(45) **Date of Patent: *Aug. 2, 2022**

US011401342B2

(54) THERAPEUTIC MOLECULES BINDING PSMA

(71) Applicant: CRESCENDO BIOLOGICS LIMITED, Cambridge (GB)

(72) Inventors: Nikki Royle, Cambridge (GB); Steve Vance, Cambridge (GB); Viviane Zelenay, Cambridge (GB)

(73) Assignee: CRESCENDO BIOLOGICS LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/627,968

(22) PCT Filed: Jul. 9, 2018

(86) PCT No.: PCT/GB2018/051941

§ 371 (c)(1),
(2) Date: Dec. 31, 2019

(87) PCT Pub. No.: WO2019/012260

PCT Pub. Date: Jan. 17, 2019

(65) Prior Publication Data

US 2020/0131274 A1 Apr. 30, 2020

(30) Foreign Application Priority Data

Jul. 10, 2017 (GB) ..................................... 1711068

(51) Int. Cl.

| | |
|---|---|
| ***C07K 16/30*** | (2006.01) |
| ***G01N 33/574*** | (2006.01) |
| ***A61K 47/68*** | (2017.01) |
| ***A61K 47/60*** | (2017.01) |

(52) U.S. Cl.

CPC .......... *C07K 16/3069* (2013.01); *A61K 47/60* (2017.08); *A61K 47/6817* (2017.08); *A61K 47/6869* (2017.08); *G01N 33/57434* (2013.01); *G01N 33/57492* (2013.01); *C07K 2317/14* (2013.01); *C07K 2317/21* (2013.01); *C07K 2317/31* (2013.01); *C07K 2317/565* (2013.01); *C07K 2317/569* (2013.01); *C07K 2317/73* (2013.01); *C07K 2317/77* (2013.01); *C07K 2317/92* (2013.01); *C07K 2317/94* (2013.01)

(58) Field of Classification Search

CPC ............ C07K 16/3069; C07K 2317/14; C07K 2317/21; C07K 2317/31; C07K 2317/565; C07K 2317/569

See application file for complete search history.

(56) References Cited

U.S. PATENT DOCUMENTS

| | | | |
|---|---|---|---|
| 10,975,161 B2 | 4/2021 | Balloi et al. | |
| 11,236,174 B2 | 2/2022 | McGuinness et al. | |
| 2010/0122358 A1 | 5/2010 | Brueggemann et al. | |
| 2019/0023807 A1 | 1/2019 | Balloi et al. | |
| 2019/0144561 A1 | 5/2019 | McGuinness et al. | |
| 2020/0362051 A1 * | 11/2020 | Brucklacher-Waldert | C07K 16/30 |
| 2020/0392244 A1 | 12/2020 | Balloi et al. | |
| 2022/0112305 A1 | 4/2022 | McGuinness et al. | |

FOREIGN PATENT DOCUMENTS

| | | |
|---|---|---|
| CN | 103087171 A | 5/2013 |
| CN | 103333249 A | 10/2013 |
| CN | 104159909 A | 11/2014 |
| CN | 105384825 | 3/2016 |
| EP | 2363404 B1 | 9/2016 |
| WO | 2006089230 A2 | 8/2006 |
| WO | 2007117264 A2 | 10/2007 |
| WO | 2013126712 A1 | 8/2013 |
| WO | 2014/141192 | 9/2014 |
| WO | 2014198223 A1 | 12/2014 |
| WO | 2015/142675 | 9/2015 |
| WO | 2015143079 A1 | 9/2015 |
| WO | 2016/025880 | 2/2016 |
| WO | 2017122017 A1 | 7/2017 |
| WO | 2017122019 A1 | 7/2017 |
| WO | WO 2017/122018 | 7/2017 |
| WO | WO 2017/191476 | 11/2017 |
| WO | 2019092451 A1 | 5/2019 |
| WO | 2019092452 A1 | 5/2019 |

OTHER PUBLICATIONS

"U.S. Appl. No. 16/069,495; office action dated Aug. 11, 2020."
"Examination Report corresponding to European Application No. 17700734.1 dated Jul. 24, 2020."
"Examination Report corresponding to European Application No. 17724869.7 dated Dec. 4, 2019."
"International Search Report and Written Opinion corresponding to International Application No. PCT/GB2018/051941 dated Sep. 14, 2018."
Bander , et al., "Targeted Systematic Therapy of Prostate Cancer With a Monoclonal Antibody to Prostate-Specific Membrane Antigen", Semin Oncol. 30:667-677 (2003).
Bruggemann , et al., "A Repertoire of Monoclonal Antibodies With Human Heavy Chains From Transgenic Mice", Proceedings of the National Academy Sciences, National Academy of Sciences, vol. 86, No. 17, Sep. 1, 1989 (Sep. 1, 1989 ), pp. 6709-6713.
Cizeau , et al., "Engineering and characterization of anti-PSMA humabody-deBouganin fusion proteins", Proceedings of the American Association for Cancer Research Annual Meeting 2018; Apr. 2018 (Apr. 2018), Retrieved from the Internet: URL:http://cancerres.aacrjournals.org.

(Continued)

*Primary Examiner* — Brad Duffy
*Assistant Examiner* — Cheom-Gil Cheong
(74) *Attorney, Agent, or Firm* — Myers Bigel, P.A.

(57) ABSTRACT

The invention relates to improved binding molecules that bind specifically to prostate specific membrane antigen (PSMA), in particular, single human variable heavy chain domain antibodies and related methods for treatment of cancer.

22 Claims, 28 Drawing Sheets

Figure 1A:
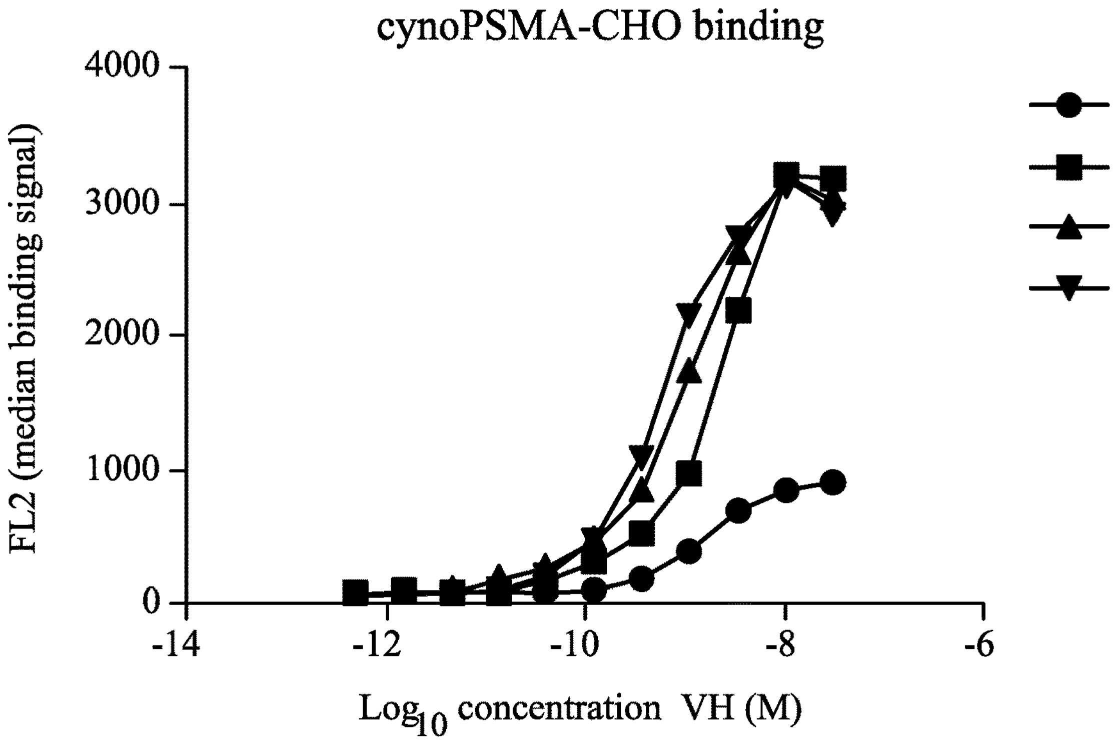
Figure 1A:
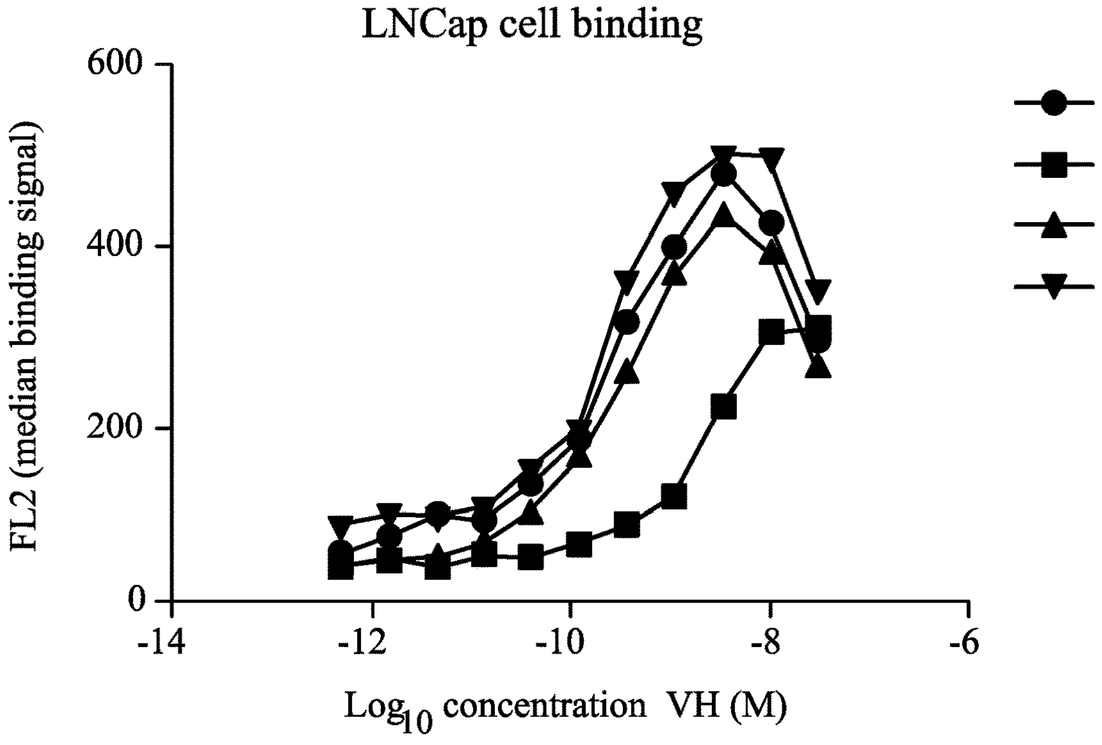
Figure 1A:
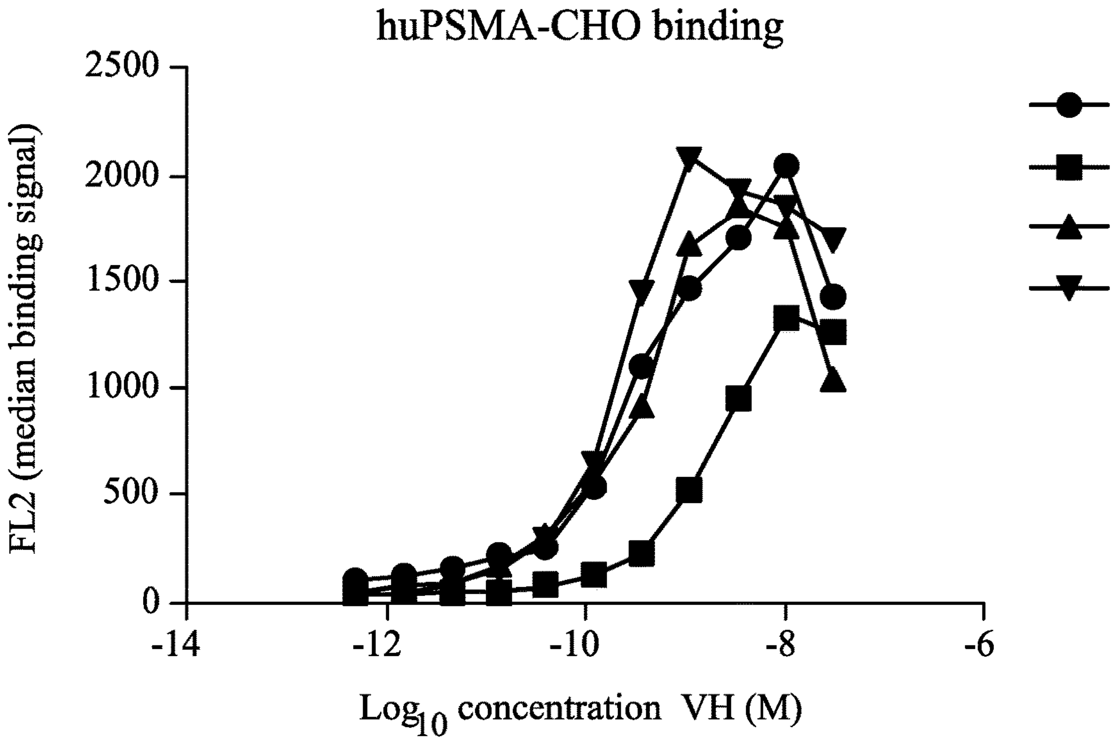
Figure 1A:
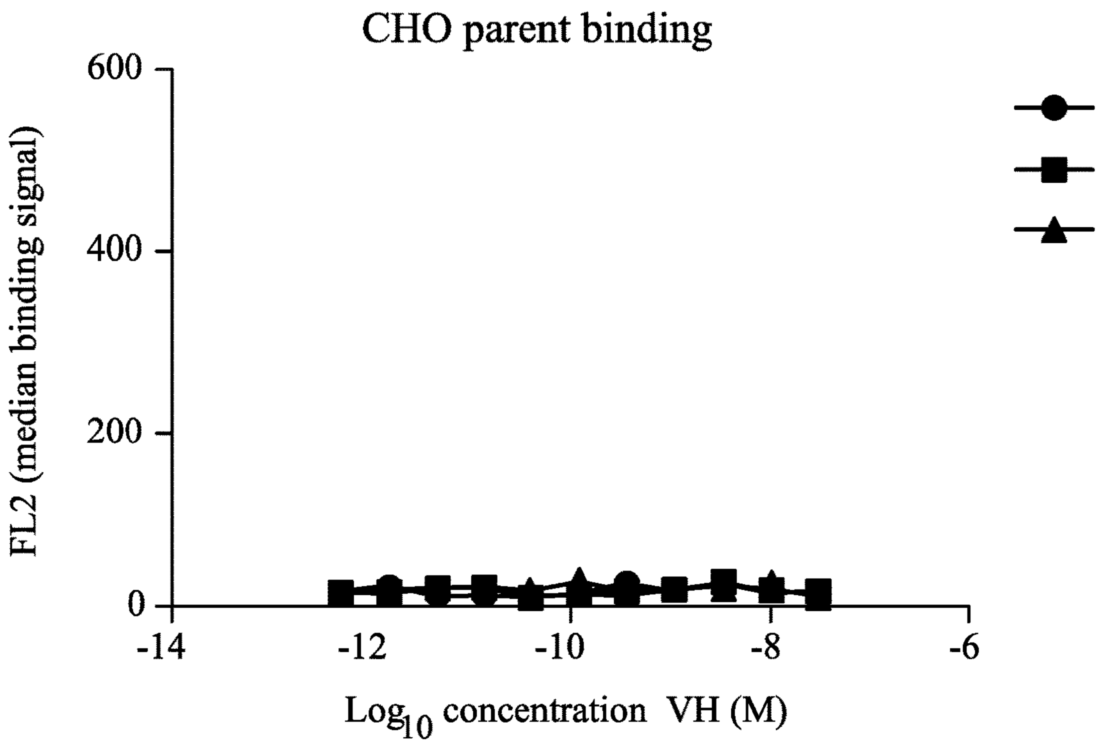

Specification includes a Sequence Listing.

(56) References Cited

OTHER PUBLICATIONS

Guo, Yelei , et al., "Chimeric Antigen Receptor-Modified T Cells for Solid Tumors: Challenges and Prospects", Journal of Immunology Research vol. 2016 (Feb. 21, 2016) 11 pages.
Zare , et al., "Production of nanobodies against prostate-specific membrane antigen (PSMA) recognizing LnCaP cells", Int J Biol Markers 29(2):e169-e179 (2014).
Evazalipour et al. "Generation and characterization of nanobodies targeting PSMA for molecular imaging of prostate cancer", Contrast Media & Molecular Imaging 9(3):211-220 (2014).
Examination Report corresponding to European Application No. 17701006.3 dated Jun. 5, 2019.
"U.S. Appl. No. 16/069,497; office action dated May 12, 2021."
Bahara, Nur Hidaya Hairul, et al., "Construction of a Semisynthetic Human VH Single-Domain Antibody Library and Selection of Domain Antibodies against alpha-Crystalline of *Mycobacterium tuberculosis*", Journal of Biomolecular Screening 21(1):35-43 (Jan. 2016).
Chen, Longxin , et al., "Epitope-directed antibody selection by site-specific photocrosslinking", Science Advances 6(14):eaaz7825 (Apr. 1, 2020) (9 pages).
Vincke, Cecile , et al., "Introduction to Heavy Chain Antibodies and Derived Nanobodies", Single Domain Antibodies. Methods in Molecular Biology (Methods and Protocols), vol. 911 https://doi.org/10.1007/978-1-61779-968-6_2 (Jul. 12, 2012).
Barve et al. "Prostate cancer relevant antigens and enzymes for targeted drug delivery", J Control Release 187:118-132 (2014).
Holt L J et al: "Domain antibodies: proteins for therapy", Trends in Biotechnology, Elsevier Publications, Cambridge, GB, vol. 21, No. 11, Nov. 1, 2003 (Nov. 1, 2003), pp. 484-490.
International Search Report and Written Opinion corresponding to International Application No. PCT/GB2017/050074 dated May 30, 2017.
Matthias Di Huyvetter et al: "Radiolabeled nanobodies as theranostic tools in targeted radionuclide therapy of cancer", Expert Opinion on Drug Delivery, vol. 1-6, 49-8111, No. 12, Jul. 18, 2014 (Jul. 18, 2014), pp. 1939-1954.
Rob C. Roovers et al: "A biparatopic anti-EGFR nanobody efficiently inhibits solid tumour growth", International Journal of Cancer, vol. 129, No. 8, Oct. 15, 2011 (Oct. 15, 2011), pp. 2013-2024.
Bayachou, Mekki et al. "Catalytic Two-Electron Reductions of N2) and N3 by My globin in Surfactant Films" Inorg. Chem. 2000, 39, 289-293.
Fan, Xiaozhu et al. Ultrasonic Nanobubbles Carrying Anti-PSMA Nanobody: Construction and Application in Prostate Cancer-Targeted Imaging. PLOS ONE. Jun. 25, 2015. p. 1-13.
Hamed, Production of Nanobodies Against Prostate-Specific Membrane Antigen (PSMA) Recognizing LnCaP Cells. Research Gate. The International Journal of Biological Markers. Jan. 2014.
International Search Report and Written Opinion corresponding to International Application No. PCT/GB2017/050075 dated Mar. 23, 2017.
International Preliminary Report on Patentability corresponding to International Application No. PCT/GB2017/050074 dated Jul. 26, 2018.
International Preliminary Report on Patentability corresponding to International Application No. PCT/GB2017/050075 dated Jul. 26, 2018.
International Preliminary Report on Patentability corresponding to International Application No. PCT/GB2017/051272 dated Nov. 15, 2018.
International Preliminary Report on Patentability corresponding to International Application No. PCT/GB2018/051941 dated Jan. 23, 2020.
International Search Report and Written Opinion corresponding to International Application No. PCT/GB2017/051272 dated Sep. 11, 2017.
Fatemeh Rahimi Jamnani et al. "T cells expressing VHH-directed oligoclonal chimeric HER2 antigen receptors: Towards tumor-directed oligoclonal T cell therapy", Biochimica Et Biophysica Acta (BB) General Subjects 1840(1):378-386 (2014).
Mehdi Evaza Lipour et al: "Camel Heavy Chain Antibodies Against Prostate-Specific Membrane Antigen", Hybridoma, vol. 31, No. 6; Dec. 1, 2012, pp. 424-429.
K. L. S. Chatalic et al: "A Novel N-Labeled Anti-Prostate-Specific Membrane Antigen Nanobody for Targeted SPECT/CT Imaging of Prostate Cancer", The Journal of Nuclear Medicine, vol. 56, No. 7, Jul. 1, 2015; pp. 1094-1099.
Crescendo Biologics: "Humabody fragments: Small and perfectly formed" Mar. 15, 2015 pp. B12-B13, Retrieved from the Internet: URL:http://www.crescendobiologics.com/uploads/news/id34/Crescendo0315.pdf.
McGuiness et al: "Multifunctional biologics for targeted T-cell therapy based on in vivo matured fully human VH domains", Proceedings of the American Association for Cancer Research Annual Meeting 2018; Apr. 2018.
International Search Report for PCT/GB2018/051941 dated Aug. 31, 2018.
"Office Action corresponding to Japanese Application No. 2018-537519 dated Feb. 5, 2021."
"Office Action corresponding to Japanese Application No. 2018-537533 dated Feb. 16, 2021."
Conrath, Katja Els, et al., "Camel Single-Domain Antibodies as Modular Building Units in Bispecific and Bivalent Antibody Constructs", The Journal of Biological Chemistry 276(10):7346-7350 (Mar. 2001).
Vincke, Cecile , et al., "General strategy to Humanize a Camelid Single-domain Antibody and Identification of a Universal Humanized Nanobody Scaffold", The Journal of Biological Chemistry 284(5):3273-3284 (Jan. 30, 2009).
"Office Action corresponding to Chinese Application No. 201780039280.9 dated Sep. 23, 2021."
Zare, Hamed , et al., "Production of nanobodies against prostate-specific membrane antigen (PSMA) recognizing LnCaP cells", Int J Biol Markers 29(2):e169-e179 (2014).
"U.S. Appl. No. 16/099,099; office action dated Dec. 20, 2021."

* cited by examiner (serum stability) Binding of 2.22 on CHO human PSMA (serum stability) Binding of 1.8 on CHO human PSMA (serum stability) Binding of 1.11 on CHO human PSMA (serum stability) Binding of 1.16 on CHO human PSMA (serum stability) Binding of 1.17 on CHO human PSMA (serum stability) Binding of 1.18 on CHO human PSMA e)

a)

b)

c)

d)

e)

d)

e)

d)

e)

SEQUENCE LISTING

```
<160> NUMBER OF SEQ ID NOS: 257

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.4
```

<400> SEQUENCE: 1

Ser Tyr Ala Leu Ser
1 5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.4

<400> SEQUENCE: 2

Ser Ile Gly Glu Asn Asp Gly Thr Thr Asp Tyr Ala Asp Phe Val Lys
1 5 10 15

Gly

<210> SEQ ID NO 3
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.4

<400> SEQUENCE: 3

Asp Gly Val His
1

<210> SEQ ID NO 4
<211> LENGTH: 113
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Leu Ser Trp Val Arg Gln Ala Pro Gly Lys Gly Leu Glu Trp Val
35 40 45

Ser Ser Ile Gly Glu Asn Asp Gly Thr Thr Asp Tyr Ala Asp Phe Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 5
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.8

<400> SEQUENCE: 5

Ser Tyr Ala Leu Ser
1 5

<210> SEQ ID NO 6
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.8

<400> SEQUENCE: 6

Ser Ile Gly Glu Asn Asp Gly Thr Thr Asp Tyr Ala Asp Asn Val Lys
1 5 10 15

Gly

<210> SEQ ID NO 7
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.8

<400> SEQUENCE: 7

Asp Gly Val His
1

<210> SEQ ID NO 8
<211> LENGTH: 113
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Leu Ser Trp Val Arg Gln Ala Pro Gly Lys Gly Leu Glu Trp Val
35 40 45

Ser Ser Ile Gly Glu Asn Asp Gly Thr Thr Asp Tyr Ala Asp Asn Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 9
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.12

<400> SEQUENCE: 9

```
Ser Tyr Ala Leu Ser
1               5


<210> SEQ ID NO 10
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.12

<400> SEQUENCE: 10

Ser Ile Gly Glu Asn Asp Gly Thr Thr Asp Tyr Ala Ala Asp Val Lys
1               5                   10                  15

Gly


<210> SEQ ID NO 11
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.12

<400> SEQUENCE: 11

Asp Gly Val His
1


<210> SEQ ID NO 12
<211> LENGTH: 113
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Ala Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser


<210> SEQ ID NO 13
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.16

<400> SEQUENCE: 13
```

Ser Tyr Ala Leu Ser
1 5

<210> SEQ ID NO 14
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.16

<400> SEQUENCE: 14

Ser Ile Gly Glu Asn Asp Gly Thr Thr Asp Tyr Ala Asp Val Val Lys
1 5 10 15

Gly

<210> SEQ ID NO 15
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.16

<400> SEQUENCE: 15

Asp Gly Val His
1

<210> SEQ ID NO 16
<211> LENGTH: 113
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Leu Ser Trp Val Arg Gln Ala Pro Gly Lys Gly Leu Glu Trp Val
35 40 45

Ser Ser Ile Gly Glu Asn Asp Gly Thr Thr Asp Tyr Ala Asp Val Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 17
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.20

<400> SEQUENCE: 17

Ser Tyr Ala Leu Ser 1 5

<210> SEQ ID NO 18
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.20

<400> SEQUENCE: 18

Ser Ile Gly Glu Asn Asp Gly Thr Thr Asp Tyr Ala Ala Phe Val Lys
1 5 10 15

Gly

<210> SEQ ID NO 19
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.20

<400> SEQUENCE: 19

Asp Gly Val His
1

<210> SEQ ID NO 20
<211> LENGTH: 113
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Leu Ser Trp Val Arg Gln Ala Pro Gly Lys Gly Leu Glu Trp Val
35 40 45

Ser Ser Ile Gly Glu Asn Asp Gly Thr Thr Asp Tyr Ala Ala Phe Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 21
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.24

<400> SEQUENCE: 21

Ser Tyr Ala Leu Ser
1 5

<210> SEQ ID NO 22
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.24

<400> SEQUENCE: 22

```
Ser Ile Gly Glu Asn Asp Gly Thr Thr Asp Tyr Ala Asp Thr Val Lys
1               5                   10                  15

Gly
```

<210> SEQ ID NO 23
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.24

<400> SEQUENCE: 23

```
Asp Gly Val His
1
```

<210> SEQ ID NO 24
<211> LENGTH: 113
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 25
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.28

<400> SEQUENCE: 25

```
Ser Tyr Ala Leu Ser
1               5
```

<210> SEQ ID NO 26
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.28

<400> SEQUENCE: 26

Ser Ile Gly Glu Asn Asp Gly Thr Thr Asp Tyr Ala Asp Ala Val Lys
1               5                   10                  15

Gly

<210> SEQ ID NO 27
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.28

<400> SEQUENCE: 27

Asp Gly Val His
1

<210> SEQ ID NO 28
<211> LENGTH: 113
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 29
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.32

<400> SEQUENCE: 29

Ser Tyr Ala Leu Ser
1               5

<210> SEQ ID NO 30
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.32

<400> SEQUENCE: 30

Ser Ile Gly Glu Asn Asp Gly Thr Thr Asp Tyr Ala Ala Ser Val Lys
1 5 10 15

Gly

<210> SEQ ID NO 31
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.32

<400> SEQUENCE: 31

Asp Gly Val His
1

<210> SEQ ID NO 32
<211> LENGTH: 113
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Leu Ser Trp Val Arg Gln Ala Pro Gly Lys Gly Leu Glu Trp Val
35 40 45

Ser Ser Ile Gly Glu Asn Asp Gly Thr Thr Asp Tyr Ala Ala Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 33
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.36

<400> SEQUENCE: 33

Ser Tyr Ala Leu Ser
1 5

<210> SEQ ID NO 34

```
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.36

<400> SEQUENCE: 34

Ser Ile Gly Glu Asn Asp Gly Thr Thr Asp Tyr Ala Ala Tyr Val Lys
1               5                   10                  15

Gly


<210> SEQ ID NO 35
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.36

<400> SEQUENCE: 35

Asp Gly Val His
1


<210> SEQ ID NO 36
<211> LENGTH: 113
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Ala Tyr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser


<210> SEQ ID NO 37
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO.40

<400> SEQUENCE: 37

Ser Tyr Ala Leu Ser
1               5


<210> SEQ ID NO 38
<211> LENGTH: 17
```

<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.40

<400> SEQUENCE: 38

Ser Ile Gly Glu Asn Asp Gly Thr Thr Asp Tyr Ala Ala Thr Val Lys
1 5 10 15

Gly

<210> SEQ ID NO 39
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 of SEQ ID NO.40

<400> SEQUENCE: 39

Asp Gly Val His
1

<210> SEQ ID NO 40
<211> LENGTH: 113
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Leu Ser Trp Val Arg Gln Ala Pro Gly Lys Gly Leu Glu Trp Val
35 40 45

Ser Ser Ile Gly Glu Asn Asp Gly Thr Thr Asp Tyr Ala Ala Thr Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 41
<211> LENGTH: 113
<212> TYPE: PRT
<213> ORGANISM: Homo sapiens

<400> SEQUENCE: 41

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Met Ser Trp Val Arg Gln Ala Pro Gly Lys Gly Leu Glu Trp Val
35 40 45

Ser Ser Ile Gly Glu Asn Asp Gly Thr Thr Asp Tyr Ala Asp Ser Val
50 55 60

Lys Gly Arg Phe Thr Ile Ser Arg Asp Asn Ser Lys Ser Met Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 42
<211> LENGTH: 113
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Gly Asp Asn Asn Asn Ser Thr Glu Tyr Ala Asp Ser Val
50 55 60

Lys Gly Arg Phe Thr Ile Ser Arg Asp Asn Ser Lys Ser Thr Leu Tyr
65 70 75 80

Leu Gln Met Asn Ser Leu Ser Ala Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 43
<211> LENGTH: 113
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Met Ser Trp Val Arg Gln Ala Pro Gly Lys Gly Leu Glu Trp Val
35 40 45

Ser Ser Ile Gly Asp Asn Asn Asn Ser Thr Asp Tyr Ala Asp Ser Val
50 55 60

Lys Gly Arg Phe Thr Ile Ser Arg Asp Asn Ser Lys Ser Thr Leu Tyr
65 70 75 80

Leu Gln Met Asn Ser Leu Arg Ala Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 44
<211> LENGTH: 111
<212> TYPE: PRT
<213> ORGANISM: Homo sapiens -continued

<400> SEQUENCE: 44

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Gly Asp Gly Thr Thr Tyr Tyr Ala Asp Ser Val Lys Gly
50 55 60

Arg Phe Thr Ile Ser Arg Asp Asn Ser Lys Ser Thr Leu Tyr Leu Gln
65 70 75 80

Met Asn Ser Leu Arg Ala Glu Asp Thr Ala Val Tyr Tyr Cys Ala Lys
85 90 95

Asp Gly Val His Trp Gly Gln Gly Thr Leu Val Thr Val Ser Ser
100 105 110

<210> SEQ ID NO 45
<211> LENGTH: 113
<212> TYPE: PRT
<213> ORGANISM: Homo sapiens

<400> SEQUENCE: 45

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Ser Trp Val Arg Gln Ala Pro Gly Lys Gly Leu Glu Trp Val
35 40 45

Ser Ser Ile Gly Glu Asn Asp Arg Thr Thr Tyr Tyr Val Asp Ser Val
50 55 60

Lys Gly Arg Phe Thr Ile Ser Arg Asp Asn Ser Lys Ser Thr Leu Tyr
65 70 75 80

Leu Gln Met Asn Ser Leu Arg Ala Glu Asp Thr Ala Val Tyr Tyr Cys
85 90 95

Ala Lys Asp Gly Val His Trp Gly Gln Gly Thr Leu Val Thr Val Ser
100 105 110

Ser

<210> SEQ ID NO 46
<211> LENGTH: 113
<212> TYPE: PRT
<213> ORGANISM: Homo sapiens

<400> SEQUENCE: 46

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Gly Asp Asn Asn Arg Thr Thr Tyr Tyr Ala Asp Ser Val
50 55 60

Lys Gly Arg Phe Thr Ile Ser Arg Asp Asn Ser Lys Ser Thr Leu Tyr
65 70 75 80

Leu Gln Met Asn Ser Leu Arg Ala Glu Asp Thr Ala Val Tyr Tyr Cys

```
                85                  90                  95

Ala Lys Asp Gly Val His Trp Gly Gln Gly Thr Leu Val Thr Val Ser
            100                 105                 110

Ser


<210> SEQ ID NO 47
<211> LENGTH: 111
<212> TYPE: PRT
<213> ORGANISM: Homo sapiens

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Asp Gly Thr Thr Tyr Tyr Ala Asp Ser Val Lys Gly
    50                  55                  60

Arg Phe Thr Ile Ser Arg Asp Asn Ser Lys Ser Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Gly Val His Trp Gly Gln Gly Thr Leu Val Thr Val Ser Ser
            100                 105                 110


<210> SEQ ID NO 48
<211> LENGTH: 113
<212> TYPE: PRT
<213> ORGANISM: Homo sapiens

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser


<210> SEQ ID NO 49
<211> LENGTH: 113
<212> TYPE: PRT
<213> ORGANISM: Homo sapiens

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
```

-continued

```
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser


<210> SEQ ID NO 50
<211> LENGTH: 113
<212> TYPE: PRT
<213> ORGANISM: Homo sapiens

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Ala Thr Thr Asp Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser


<210> SEQ ID NO 51
<211> LENGTH: 113
<212> TYPE: PRT
<213> ORGANISM: Homo sapiens

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Asp Thr Thr Asp Tyr Ala Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110
```

-continued

Ser

<210> SEQ ID NO 52
<211> LENGTH: 113
<212> TYPE: PRT
<213> ORGANISM: Homo sapiens

<400> SEQUENCE: 52

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Ala Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 53
<211> LENGTH: 113
<212> TYPE: PRT
<213> ORGANISM: Homo sapiens

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn His Thr Thr Asp Tyr Ala Ala Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 54
<211> LENGTH: 113
<212> TYPE: PRT
<213> ORGANISM: Homo sapiens

<400> SEQUENCE: 54

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
```

-continued

```
        35                  40                  45

Ser Ser Ile Gly Glu Asn Asn Ala Thr Thr Asp Tyr Ala Asp Val Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser


<210> SEQ ID NO 55
<211> LENGTH: 113
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn His Thr Thr Asp Tyr Ala Ala Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser


<210> SEQ ID NO 56
<211> LENGTH: 113
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn His Thr Thr Asp Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 57
<211> LENGTH: 113
<212> TYPE: PRT
<213> ORGANISM: Homo sapiens

<400> SEQUENCE: 57

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Asp Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 58
<211> LENGTH: 113
<212> TYPE: PRT
<213> ORGANISM: Homo sapiens

<400> SEQUENCE: 58

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Ala Thr Thr Asp Tyr Ala Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 59
<211> LENGTH: 113
<212> TYPE: PRT
<213> ORGANISM: Homo sapiens

<400> SEQUENCE: 59

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asn Asp Thr Thr Asp Tyr Ala Ala Tyr Val
```

50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 60
<211> LENGTH: 113
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Leu Ser Trp Val Arg Gln Ala Pro Gly Lys Gly Leu Glu Trp Val
35 40 45

Ser Ser Ile Gly Glu Asn Asn His Thr Thr Asp Tyr Ala Ala Thr Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser

<210> SEQ ID NO 61
<211> LENGTH: 339
<212> TYPE: DNA
<213> ORGANISM: Homo sapiens

<400> SEQUENCE: 61
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga ataacgctac cacagactac 180
gcagacttcg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 62
<211> LENGTH: 339
<212> TYPE: DNA
<213> ORGANISM: Homo sapiens

<400> SEQUENCE: 62
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180
gcagacgccg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 63
<211> LENGTH: 339
<212> TYPE: DNA
<213> ORGANISM: Homo sapiens

<400> SEQUENCE: 63
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180
gcagccgacg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 64
<211> LENGTH: 339
<212> TYPE: DNA
<213> ORGANISM: Homo sapiens

<400> SEQUENCE: 64
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180
gcagacgtcg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 65
<211> LENGTH: 339
<212> TYPE: DNA
<213> ORGANISM: Homo sapiens

<400> SEQUENCE: 65
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180
gcagccttcg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 66
<211> LENGTH: 339
<212> TYPE: DNA
<213> ORGANISM: Homo sapiens

<400> SEQUENCE: 66
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180
gcagacaccg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 67
<211> LENGTH: 339
<212> TYPE: DNA
<213> ORGANISM: Homo sapiens

<400> SEQUENCE: 67
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180
gcagacgccg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 68
<211> LENGTH: 339
<212> TYPE: DNA
<213> ORGANISM: Homo sapiens

<400> SEQUENCE: 68
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180
gcagcctccg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 69
<211> LENGTH: 339
<212> TYPE: DNA
<213> ORGANISM: Homo sapiens

<400> SEQUENCE: 69
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180
gcagcctacg tgaagggccg attcaccatc tccagagaca attccaagaa tacgctgtat 240
ctgcaaatga acagcctgag agtcgaggac acggccgtct attactgtgt gaaagatggt 300
gtccactggg gccagggaac cctggtcacc gtctcctca 339

<210> SEQ ID NO 70
<211> LENGTH: 339
<212> TYPE: DNA
<213> ORGANISM: Homo sapiens

<400> SEQUENCE: 70
gaggtgcagc tgttggagtc tgggggaggc ttggtacagc ctggggggtc cctgagactc 60
tcctgtgcag cctctggatt cagttttagc agctatgccc tcagttgggt ccgccaggct 120
ccagggaagg ggctggagtg ggtctcaagt attggtgaga atgatggtac cacagactac 180

```
gcagccaccg tgaagggccg attcaccatc tccagagaca attccaagaa tacgctgtat    240

ctgcaaatga acagcctgag agtcgaggac acggccgtct attactgtgt gaaagatggt    300

gtccactggg gccagggaac cctggtcacc gtctcctca                           339


<210> SEQ ID NO 71
<211> LENGTH: 127
<212> TYPE: PRT
<213> ORGANISM: Homo sapiens

<400> SEQUENCE: 71

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125


<210> SEQ ID NO 72
<211> LENGTH: 127
<212> TYPE: PRT
<213> ORGANISM: Homo sapiens

<400> SEQUENCE: 72

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125


<210> SEQ ID NO 73
<211> LENGTH: 127
<212> TYPE: PRT
<213> ORGANISM: Homo sapiens

<400> SEQUENCE: 73
```

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala His Ile Ser Tyr Asp Gly Ser Asn Arg Tyr Tyr Ala Glu Ser Val
    50                  55                  60

Lys Gly Arg Phe Thr Ile Ser Arg Glu Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Leu Ser Ser Tyr
            100                 105                 110

Asp Phe Asp Ile Trp Gly Gln Gly Thr Met Val Thr Val Ser Ser
        115                 120                 125


<210> SEQ ID NO 74
<211> LENGTH: 127
<212> TYPE: PRT
<213> ORGANISM: Homo sapiens

<400> SEQUENCE: 74

Gln Val Thr Leu Lys Glu Ser Gly Gly Gly Val Val Gln Pro Gly Arg
1               5                   10                  15

Ser Leu Lys Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Arg Asp Pro Ala Trp Gly Leu Arg Leu Gly Glu Leu Ser Ser Tyr
            100                 105                 110

Asp Phe Glu Ile Trp Gly Gln Gly Thr Met Val Thr Val Ser Ser
        115                 120                 125


<210> SEQ ID NO 75
<211> LENGTH: 127
<212> TYPE: PRT
<213> ORGANISM: Homo sapiens

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Ser
65                  70                  75                  80
```

-continued

```
Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Leu Ser Ser Tyr
            100                 105                 110

Asp Phe Glu Ile Trp Gly Gln Gly Thr Met Val Thr Val Ser Ser
        115                 120                 125


<210> SEQ ID NO 76
<211> LENGTH: 127
<212> TYPE: PRT
<213> ORGANISM: Homo sapiens

<400> SEQUENCE: 76

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Leu Ser Ser Tyr
            100                 105                 110

Lys Phe Glu Ile Trp Gly Gln Gly Thr Met Val Thr Val Ser Ser
        115                 120                 125


<210> SEQ ID NO 77
<211> LENGTH: 127
<212> TYPE: PRT
<213> ORGANISM: Homo sapiens

<400> SEQUENCE: 77

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Gln Ser Ser Tyr
            100                 105                 110

Ala Phe Asp Ile Trp Gly Gln Gly Thr Met Val Thr Val Ser Ser
        115                 120                 125


<210> SEQ ID NO 78
<211> LENGTH: 127
<212> TYPE: PRT
<213> ORGANISM: Homo sapiens
```

<400> SEQUENCE: 78

Gln Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Met His Trp Val Arg Gln Ala Pro Gly Lys Gly Leu Glu Trp Val
35 40 45

Ser Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Thr Glu Asp Thr Ala Val Tyr Tyr Cys
85 90 95

Ala Lys Asp Pro Ala Trp Gly Leu Arg Leu Gly Glu Gln Ser Ser Tyr
100 105 110

Ala Phe Glu Ile Trp Gly Gln Gly Thr Met Val Thr Val Ser Ser
115 120 125

<210> SEQ ID NO 79
<211> LENGTH: 127
<212> TYPE: PRT
<213> ORGANISM: Homo sapiens

<400> SEQUENCE: 79

Glu Val Gln Leu Leu Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Ala Lys Asp Pro Ala Trp Gly Leu Arg Leu Gly Glu Gln Ser Ser Tyr
100 105 110

Ala Phe Glu Ile Arg Gly Gln Gly Thr Thr Val Thr Val Ser Ser
115 120 125

<210> SEQ ID NO 80
<211> LENGTH: 127
<212> TYPE: PRT
<213> ORGANISM: Homo sapiens

<400> SEQUENCE: 80

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Gly Tyr
20 25 30

Gly Met His Trp Val Arg Gln Ala Pro Gly Lys Gly Leu Glu Trp Val
35 40 45

Ala Tyr Ile Ser Tyr Asp Gly Ser Asn Arg Tyr Tyr Ala Asp Ser Val
50 55 60

Lys Gly Arg Phe Thr Ile Ser Arg Asp Asn Ser Lys Lys Thr Leu Ser

```
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125


<210> SEQ ID NO 81
<211> LENGTH: 127
<212> TYPE: PRT
<213> ORGANISM: Homo sapiens

<400> SEQUENCE: 81

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Leu His Trp Val Arg Gln Ala Pro Gly Lys Gly Leu Glu Trp Val
        35                  40                  45

Ala Tyr Ile Ser Tyr Asp Glu Ser Asn Lys Tyr Tyr Ala Pro Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125


<210> SEQ ID NO 82
<211> LENGTH: 127
<212> TYPE: PRT
<213> ORGANISM: Homo sapiens

<400> SEQUENCE: 82

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Lys Ser Asn Lys Tyr Tyr Ala Asp Lys Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125


<210> SEQ ID NO 83
<211> LENGTH: 127
<212> TYPE: PRT
```

<213> ORGANISM: Homo sapiens

<400> SEQUENCE: 83

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Leu His Trp Val Arg Gln Ala Pro Gly Lys Gly Leu Glu Trp Val
35 40 45

Ala Tyr Ile Ser Tyr Asp Ala Ser Asn Lys Tyr Tyr Ala Asp Asn Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Pro Ala Trp Gly Leu Arg Leu Gly Glu Ser Ser Ser Tyr
100 105 110

Asp Phe Asp Ile Trp Gly Gln Gly Thr Met Val Thr Val Ser Ser
115 120 125

<210> SEQ ID NO 84
<211> LENGTH: 127
<212> TYPE: PRT
<213> ORGANISM: Homo sapiens

<400> SEQUENCE: 84

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Val His Trp Val Arg Gln Ala Pro Gly Lys Gly Leu Glu Trp Val
35 40 45

Ala Tyr Ile Ser Tyr Asp Ala Ser Asn Lys Tyr Tyr Ala Asp Asn Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Pro Ala Trp Gly Leu Arg Leu Gly Glu Ser Ser Ser Tyr
100 105 110

Asp Phe Asp Ile Trp Gly Gln Gly Thr Met Val Thr Val Ser Ser
115 120 125

<210> SEQ ID NO 85
<211> LENGTH: 127
<212> TYPE: PRT
<213> ORGANISM: Homo sapiens

<400> SEQUENCE: 85

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Leu His Trp Val Arg Gln Ala Pro Gly Lys Gly Leu Glu Trp Val
35 40 45

Ala Tyr Ile Ser Tyr Asp Lys Ser Asn Lys Tyr Tyr Ala Asp Lys Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Pro Ala Trp Gly Leu Arg Leu Gly Glu Ser Ser Ser Tyr
100 105 110

Asp Phe Asp Ile Trp Gly Gln Gly Thr Met Val Thr Val Ser Ser
115 120 125

<210> SEQ ID NO 86
<211> LENGTH: 127
<212> TYPE: PRT
<213> ORGANISM: Homo sapiens

<400> SEQUENCE: 86

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Ala His Trp Val Arg Gln Ala Pro Gly Lys Gly Leu Glu Trp Val
35 40 45

Ala Tyr Ile Ser Tyr Asp Lys Ser Asn Lys Tyr Tyr Ala Asp Lys Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Pro Ala Trp Gly Leu Arg Leu Gly Glu Ser Ser Ser Tyr
100 105 110

Asp Phe Asp Ile Trp Gly Gln Gly Thr Met Val Thr Val Ser Ser
115 120 125

<210> SEQ ID NO 87
<211> LENGTH: 127
<212> TYPE: PRT
<213> ORGANISM: Homo sapiens

<400> SEQUENCE: 87

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Met His Trp Val Arg Gln Ala Pro Gly Lys Gly Leu Glu Trp Val
35 40 45

Ala Tyr Ile Ser Tyr Asp Ala Ser Asn Lys Tyr Tyr Ala Asp Asn Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Pro Ala Trp Gly Leu Arg Leu Gly Glu Ser Ser Ser Tyr
100 105 110

Asp Phe Asp Ile Trp Gly Gln Gly Thr Met Val Thr Val Ser Ser
115 120 125

<210> SEQ ID NO 88

<211> LENGTH: 127
<212> TYPE: PRT
<213> ORGANISM: Homo sapiens

<400> SEQUENCE: 88

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Gln His Trp Val Arg Gln Ala Pro Gly Lys Gly Leu Glu Trp Val
        35                  40                  45

Ala Tyr Ile Ser Tyr Asp Ala Ser Asn Lys Tyr Tyr Ala Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 89
<211> LENGTH: 127
<212> TYPE: PRT
<213> ORGANISM: Homo sapiens

<400> SEQUENCE: 89

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Phe His Trp Val Arg Gln Ala Pro Gly Lys Gly Leu Glu Trp Val
        35                  40                  45

Ala Tyr Ile Ser Tyr Asp Ala Ser Asn Lys Tyr Tyr Ala Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 90
<211> LENGTH: 127
<212> TYPE: PRT
<213> ORGANISM: Homo sapiens

<400> SEQUENCE: 90

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

```
Ala Ile Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Glu Ile Trp Gly Gln Gly Thr Met Val Thr Val Ser Ser
        115                 120                 125
```

<210> SEQ ID NO 91
<211> LENGTH: 127
<212> TYPE: PRT
<213> ORGANISM: Homo sapiens

<400> SEQUENCE: 91

```
Gln Val Gln Leu Val Glu Ser Gly Gly Gly Val Val Gln Pro Gly Arg
1               5                   10                  15

Ser Leu Lys Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Lys Leu Ser Ser Tyr
            100                 105                 110

Asp Phe Glu Ile Trp Gly Gln Gly Thr Met Val Thr Val Ser Ser
        115                 120                 125
```

<210> SEQ ID NO 92
<211> LENGTH: 127
<212> TYPE: PRT
<213> ORGANISM: Homo sapiens

<400> SEQUENCE: 92

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Thr His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Ala Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125
```

<210> SEQ ID NO 93
<211> LENGTH: 127
<212> TYPE: PRT
<213> ORGANISM: Homo sapiens

<400> SEQUENCE: 93

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Thr His Trp Val Arg Gln Ala Pro Gly Lys Gly Leu Glu Trp Val
        35                  40                  45

Ala Tyr Ile Ser Tyr Asp Glu Ser Asn Lys Tyr Tyr Ala Ser Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125
```

<210> SEQ ID NO 94
<211> LENGTH: 127
<212> TYPE: PRT
<213> ORGANISM: Homo sapiens

<400> SEQUENCE: 94

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Glu Ser Asn Lys Tyr Tyr Ala Arg Leu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125
```

<210> SEQ ID NO 95
<211> LENGTH: 127
<212> TYPE: PRT
<213> ORGANISM: Homo sapiens

<400> SEQUENCE: 95

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Leu His Trp Val Arg Gln Ala Pro Gly Lys Gly Leu Glu Trp Val
```

```
        35                  40                  45

Ala Tyr Ile Ser Tyr Asp Leu Ser Asn Lys Tyr Tyr Ala Arg Gly Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125


<210> SEQ ID NO 96
<211> LENGTH: 123
<212> TYPE: PRT
<213> ORGANISM: Homo sapiens

<400> SEQUENCE: 96

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Met Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Leu Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120


<210> SEQ ID NO 97
<211> LENGTH: 123
<212> TYPE: PRT
<213> ORGANISM: Homo sapiens

<400> SEQUENCE: 97

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Ser Tyr Asp Gly Ser Asn Lys Tyr Tyr Ala Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Val Gly Ala Arg Val Pro Asp Ala Phe Asp Ile
            100                 105                 110

Trp Gly Gln Gly Thr Met Val Thr Val Ser Ser
```

115 120

<210> SEQ ID NO 98
<211> LENGTH: 123
<212> TYPE: PRT
<213> ORGANISM: Homo sapiens

<400> SEQUENCE: 98

Glu Val Gln Leu Val Glu Ser Gly Gly Gly Val Val Gln Pro Gly Arg
1 5 10 15

Ser Leu Arg Leu Ser Cys Ala Ala Ser Gly Phe Pro Leu Ile Ser Tyr
20 25 30

Gly Met Asn Trp Val Arg Gln Ala Pro Gly Lys Gly Leu Glu Trp Val
35 40 45

Ala Phe Ile Ser Tyr Asp Gly Ser Asn Arg Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Arg Ile Val Gly Ala Arg Val Pro Asp Ala Phe Asp Ile
100 105 110

Trp Gly Gln Gly Thr Met Val Thr Val Ser Ser
115 120

<210> SEQ ID NO 99
<211> LENGTH: 123
<212> TYPE: PRT
<213> ORGANISM: Homo sapiens

<400> SEQUENCE: 99

Glu Val Gln Leu Val Glu Ser Gly Gly Gly Ala Val Gln Pro Gly Arg
1 5 10 15

Ser Leu Arg Leu Ser Cys Ala Ala Ser Gly Phe Pro Leu Ile Ser Tyr
20 25 30

Gly Met Asn Trp Val Arg Gln Ala Pro Gly Lys Gly Leu Asp Trp Val
35 40 45

Ala Phe Ile Thr Tyr Asp Gly Ser Asn Arg Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Pro Glu Asp Thr Ala Val Tyr Tyr Cys
85 90 95

Ala Lys Asp Arg Ile Val Gly Ala Arg Val Pro Asp Ala Tyr Asp Ile
100 105 110

Trp Gly Gln Gly Thr Met Val Thr Val Ser Ser
115 120

<210> SEQ ID NO 100
<211> LENGTH: 123
<212> TYPE: PRT
<213> ORGANISM: Homo sapiens

<400> SEQUENCE: 100

Gln Val Gln Leu Val Glu Ser Gly Gly Gly Val Val Gln Pro Gly Arg
1 5 10 15

Ser Leu Arg Leu Ser Cys Ala Ala Ser Gly Phe Pro Leu Ile Ser Tyr
20 25 30

```
Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 101
<211> LENGTH: 123
<212> TYPE: PRT
<213> ORGANISM: Homo sapiens

<400> SEQUENCE: 101

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 102
<211> LENGTH: 123
<212> TYPE: PRT
<213> ORGANISM: Homo sapiens

<400> SEQUENCE: 102

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asp Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110
```

Trp Gly Gln Gly Thr Met Val Thr Val Ser Ser
115 120

<210> SEQ ID NO 103
<211> LENGTH: 123
<212> TYPE: PRT
<213> ORGANISM: Homo sapiens

<400> SEQUENCE: 103

Glu Val Gln Leu Val Glu Ser Gly Gly Gly Val Val Gln Pro Gly Arg
1 5 10 15

Ser Leu Arg Leu Ser Cys Ala Ala Ser Gly Phe Pro Leu Ile Ser Tyr
20 25 30

Gly Met Asn Trp Val Arg Gln Ala Pro Gly Lys Gly Leu Asp Trp Val
35 40 45

Ala Phe Ile Thr Tyr Asp Gly Ser Asn Arg Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Pro Glu Asp Thr Ala Val Tyr Tyr Cys
85 90 95

Ala Lys Asp Arg Ile Val Gly Ala Arg Val Pro Asp Ala Tyr Asp Ile
100 105 110

Trp Gly Gln Gly Thr Leu Val Thr Val Ser Ser
115 120

<210> SEQ ID NO 104
<211> LENGTH: 123
<212> TYPE: PRT
<213> ORGANISM: Homo sapiens

<400> SEQUENCE: 104

Gln Val Gln Leu Val Glu Ser Gly Gly Gly Val Val Gln Pro Gly Arg
1 5 10 15

Ser Leu Arg Leu Ser Cys Ala Ala Ser Gly Phe Pro Leu Ile Ser Tyr
20 25 30

Gly Met Asn Trp Val Arg Gln Ala Pro Gly Lys Gly Leu Glu Trp Val
35 40 45

Ala Phe Ile Ser Tyr Asp Gly Ser Asn Arg Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Pro Glu Asp Thr Ala Val Tyr Tyr Cys
85 90 95

Ala Lys Asp Arg Ile Val Gly Ala Arg Val Pro Asp Ala Tyr Asp Ile
100 105 110

Trp Gly Gln Gly Thr Met Val Thr Val Ser Ser
115 120

<210> SEQ ID NO 105
<211> LENGTH: 123
<212> TYPE: PRT
<213> ORGANISM: Homo sapiens

<400> SEQUENCE: 105

Gln Val Gln Leu Val Glu Ser Gly Gly Gly Val Val Gln Pro Gly Arg
1 5 10 15

-continued

```
Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 106
<211> LENGTH: 123
<212> TYPE: PRT
<213> ORGANISM: Homo sapiens

<400> SEQUENCE: 106

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 107
<211> LENGTH: 123
<212> TYPE: PRT
<213> ORGANISM: Homo sapiens

<400> SEQUENCE: 107

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95
```

```
Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 108
<211> LENGTH: 123
<212> TYPE: PRT
<213> ORGANISM: Homo sapiens

<400> SEQUENCE: 108

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 109
<211> LENGTH: 123
<212> TYPE: PRT
<213> ORGANISM: Homo sapiens

<400> SEQUENCE: 109

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 110
<211> LENGTH: 123
<212> TYPE: PRT
<213> ORGANISM: Homo sapiens

<400> SEQUENCE: 110

Glu Val Gln Leu Val Glu Ser Gly Gly Gly Leu Val Gln Pro Gly Gly
```

-continued

```
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 111
<211> LENGTH: 123
<212> TYPE: PRT
<213> ORGANISM: Homo sapiens

<400> SEQUENCE: 111

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 112
<211> LENGTH: 123
<212> TYPE: PRT
<213> ORGANISM: Homo sapiens

<400> SEQUENCE: 112

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
```

```
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 113
<211> LENGTH: 123
<212> TYPE: PRT
<213> ORGANISM: Homo sapiens

<400> SEQUENCE: 113

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Asp Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120


<210> SEQ ID NO 114
<211> LENGTH: 123
<212> TYPE: PRT
<213> ORGANISM: Homo sapiens

<400> SEQUENCE: 114

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Met Thr Tyr Asp Gly Ser Asn Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120


<210> SEQ ID NO 115
<211> LENGTH: 123
<212> TYPE: PRT
<213> ORGANISM: Homo sapiens

<400> SEQUENCE: 115
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Gln Thr Tyr Asp Gly Ser Asn Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120


<210> SEQ ID NO 116
<211> LENGTH: 123
<212> TYPE: PRT
<213> ORGANISM: Homo sapiens

<400> SEQUENCE: 116

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Gln Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120


<210> SEQ ID NO 117
<211> LENGTH: 123
<212> TYPE: PRT
<213> ORGANISM: Homo sapiens

<400> SEQUENCE: 117

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Gln Thr Tyr Asp Ala Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120
```

<210> SEQ ID NO 118
<211> LENGTH: 123
<212> TYPE: PRT
<213> ORGANISM: Homo sapiens

<400> SEQUENCE: 118

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Gln Thr Tyr Asp Ala Ser Asn Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120
```

<210> SEQ ID NO 119
<211> LENGTH: 123
<212> TYPE: PRT
<213> ORGANISM: Homo sapiens

<400> SEQUENCE: 119

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met Asn Trp Val Arg Gln Ala Pro Gly Lys Gly Leu Glu Trp Val
        35                  40                  45

Ala Phe Ile Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Val Gly Ala Arg Val Pro Asp Ala Tyr Asp Ile
            100                 105                 110

Trp Gly Gln Gly Thr Met Val Thr Val Ser Ser
        115                 120
```

<210> SEQ ID NO 120
<211> LENGTH: 123
<212> TYPE: PRT
<213> ORGANISM: Homo sapiens

<400> SEQUENCE: 120

Gln Val Gln Leu Val Glu Ser Gly Gly Gly Val Val Gln Pro Gly Arg
1               5                   10                  15

Ser Leu Arg Leu Ser Cys Val Ala Ser Gly Phe Pro Phe Ile Ser Tyr
            20                  25                  30

Gly Met His Trp Val Arg Gln Ala Pro Gly Lys Gly Arg Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Glu Arg Ile Phe Gly Val Leu Thr Pro Asp Asp Phe Asp Ile
            100                 105                 110

Trp Gly Gln Gly Thr Thr Val Thr Val Ser Ser
        115                 120

<210> SEQ ID NO 121
<211> LENGTH: 123
<212> TYPE: PRT
<213> ORGANISM: Homo sapiens

<400> SEQUENCE: 121

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Phe Ile Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Glu Arg Ile Phe Gly Val Leu Thr Pro Asp Asp Phe Asp Ile
            100                 105                 110

Trp Gly Gln Gly Thr Thr Val Thr Val Ser Ser
        115                 120

<210> SEQ ID NO 122
<211> LENGTH: 123
<212> TYPE: PRT
<213> ORGANISM: Homo sapiens

<400> SEQUENCE: 122

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Pro Phe Ile Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ala Asn Arg Tyr Tyr Ala Asp Ser Val
    50                  55                  60

```
Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Glu Arg Ile Phe Gly Val Leu Thr Pro Asp Asp Phe Glu Ile
            100                 105                 110

Trp Gly Gln Gly Thr Thr Val Thr Val Ser Ser
        115                 120


<210> SEQ ID NO 123
<211> LENGTH: 123
<212> TYPE: PRT
<213> ORGANISM: Homo sapiens

<400> SEQUENCE: 123

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Glu Arg Ile Phe Gly Ala Leu Thr Pro Asp Asp Phe Asp Ile
            100                 105                 110

Trp Gly Gln Gly Thr Thr Val Thr Val Ser Ser
        115                 120


<210> SEQ ID NO 124
<211> LENGTH: 116
<212> TYPE: PRT
<213> ORGANISM: Homo sapiens

<400> SEQUENCE: 124

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Trp Val
        35                  40                  45

Ala Ile Ile Ser Tyr Asp Gly Asn Thr Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Gly Leu Trp Pro Ser Asp Val Trp Gly Gln Gly Thr Thr Val
            100                 105                 110

Thr Val Ser Ser
        115


<210> SEQ ID NO 125
<211> LENGTH: 116
```

<212> TYPE: PRT
<213> ORGANISM: Homo sapiens

<400> SEQUENCE: 125

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Asn Asn Tyr
20 25 30

Gly Met His Trp Val Arg Gln Ala Pro Gly Lys Gly Leu Glu Trp Val
35 40 45

Ala Ile Ile Ser Tyr Asp Gly Asn Ser Lys Tyr Tyr Thr Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Ala Lys Gly Leu Trp Pro Ser Asp Val Trp Gly Gln Gly Thr Thr Val
100 105 110

Thr Val Ser Ser
115

<210> SEQ ID NO 126
<211> LENGTH: 119
<212> TYPE: PRT
<213> ORGANISM: Homo sapiens

<400> SEQUENCE: 126

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Asn Ser
20 25 30

Gly Tyr Tyr Trp Ser Trp Val Arg Gln His Pro Gly Lys Asp Leu Glu
35 40 45

Trp Ile Gly Phe Ile Tyr Tyr Asn Gly Ser Ile His Tyr Asn Pro Ser
50 55 60

Leu Lys Ser Arg Val Ile Ile Ser Val Asp Thr Ser Lys Asn Gln Phe
65 70 75 80

Ser Leu Lys Met Asn Ser Val Thr Ala Ala Asp Thr Ala Val Tyr Tyr
85 90 95

Cys Ala Arg Asp Gly Asp Asp Tyr Gly Asp Tyr Leu Arg Gly Gln Gly
100 105 110

Thr Leu Val Thr Val Ser Ser
115

<210> SEQ ID NO 127
<211> LENGTH: 119
<212> TYPE: PRT
<213> ORGANISM: Homo sapiens

<400> SEQUENCE: 127

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Asn Ser
20 25 30

Gly Tyr Tyr Trp Ser Trp Ile Arg Gln His Pro Gly Lys Gly Leu Glu
35 40 45

Trp Ile Gly Phe Ile Tyr Tyr Asn Gly Ser Ile His Tyr Asn Pro Ser

```
    50                  55                  60

Leu Lys Ser Arg Val Ile Ile Ser Val Asp Thr Ser Lys Asn Gln Phe
65                  70                  75                  80

Ser Leu Lys Met Ser Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115


<210> SEQ ID NO 128
<211> LENGTH: 119
<212> TYPE: PRT
<213> ORGANISM: Homo sapiens

<400> SEQUENCE: 128

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Gly Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Ile Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115


<210> SEQ ID NO 129
<211> LENGTH: 119
<212> TYPE: PRT
<213> ORGANISM: Homo sapiens

<400> SEQUENCE: 129

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Ile Arg Gln His Pro Gly Lys Gly Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Ile Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115
```

<210> SEQ ID NO 130
<211> LENGTH: 119
<212> TYPE: PRT
<213> ORGANISM: Homo sapiens

<400> SEQUENCE: 130

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Gly Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Met Ser Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115
```

<210> SEQ ID NO 131
<211> LENGTH: 119
<212> TYPE: PRT
<213> ORGANISM: Homo sapiens

<400> SEQUENCE: 131

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Gly Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115
```

<210> SEQ ID NO 132
<211> LENGTH: 119
<212> TYPE: PRT
<213> ORGANISM: Homo sapiens

<400> SEQUENCE: 132

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Gly Leu Glu
        35                  40                  45
```

```
Trp Ile Gly Phe Ile Tyr Tyr Asn Gly Ser Ile His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115


<210> SEQ ID NO 133
<211> LENGTH: 119
<212> TYPE: PRT
<213> ORGANISM: Homo sapiens

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115


<210> SEQ ID NO 134
<211> LENGTH: 119
<212> TYPE: PRT
<213> ORGANISM: Homo sapiens

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Leu Ile Val Gly Glu Arg Gly Tyr Trp Gly Gln Gly
            100                 105                 110

Thr Leu Val Thr Val Ser Ser
        115
```

<210> SEQ ID NO 135
<211> LENGTH: 119
<212> TYPE: PRT
<213> ORGANISM: Homo sapiens

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Gly Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115

<210> SEQ ID NO 136
<211> LENGTH: 119
<212> TYPE: PRT
<213> ORGANISM: Homo sapiens

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Gln Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115

<210> SEQ ID NO 137
<211> LENGTH: 119
<212> TYPE: PRT
<213> ORGANISM: Homo sapiens

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

-continued

```
Trp Met Tyr Trp Val Arg Gln Ala Pro Gly Lys Gly Leu Glu Trp Val
        35                  40                  45

Ala Asn Ile Asn His Pro Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115


<210> SEQ ID NO 138
<211> LENGTH: 119
<212> TYPE: PRT
<213> ORGANISM: Homo sapiens

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110

Thr Leu Val Thr Val Ser Ser
        115


<210> SEQ ID NO 139
<211> LENGTH: 119
<212> TYPE: PRT
<213> ORGANISM: Homo sapiens

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Asn Ile Asn His Ile Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Ile Val Gly Glu Arg Gly Tyr Trp Gly Gln Gly
            100                 105                 110
```

-continued

Thr Leu Val Thr Val Ser Ser
115

<210> SEQ ID NO 140
<211> LENGTH: 119
<212> TYPE: PRT
<213> ORGANISM: Homo sapiens

<400> SEQUENCE: 140

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Tyr Trp Val Arg Gln Ala Pro Gly Lys Gly Leu Glu Trp Val
35 40 45

Ala Asn Ile Asn His Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Thr Leu Ile Val Gly Glu Arg Gly Tyr Trp Gly Gln Gly
100 105 110

Thr Leu Val Thr Val Ser Ser
115

<210> SEQ ID NO 141
<211> LENGTH: 122
<212> TYPE: PRT
<213> ORGANISM: Homo sapiens

<400> SEQUENCE: 141

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Pro Ile Pro Ala Thr Ala Ile Pro Asp Ala Phe Asp Ile Trp
100 105 110

Gly Gln Gly Thr Met Val Thr Val Ser Ser
115 120

<210> SEQ ID NO 142
<211> LENGTH: 119
<212> TYPE: PRT
<213> ORGANISM: Homo sapiens

<400> SEQUENCE: 142

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly His 20 25 30

Tyr Trp Ser Trp Ile Arg Gln Pro Pro Gly Lys Gly Leu Glu Trp Ile
35 40 45

Gly Asp Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Val
85 90 95

Arg Asp Tyr Gly Asp Ser Arg Ser Leu Phe Asp Tyr Trp Gly Gln Gly
100 105 110

Thr Leu Val Thr Val Ser Ser
115

<210> SEQ ID NO 143
<211> LENGTH: 125
<212> TYPE: PRT
<213> ORGANISM: Homo sapiens

<400> SEQUENCE: 143

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Met Ser Tyr Asp Gly Ser Asn Lys Tyr Tyr Val Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Asp Tyr Asp Phe Trp Ser Gly Tyr Pro Asp Tyr Asp Met
100 105 110

Asp Val Trp Gly Gln Gly Thr Thr Val Thr Val Ser Ser
115 120 125

<210> SEQ ID NO 144
<211> LENGTH: 126
<212> TYPE: PRT
<213> ORGANISM: Homo sapiens

<400> SEQUENCE: 144

Glu Val Gln Leu Val Glu Ser Gly Gly Gly Leu Val Lys Pro Gly Gly
1 5 10 15

Ser Leu Arg Leu Ser Cys Ala Ala Ser Gly Phe Asn Leu Ile Ser Tyr
20 25 30

Gly Met Tyr Trp Val Arg Gln Ala Pro Gly Lys Gly Leu Glu Trp Val
35 40 45

Ala Val Ile Ser Tyr Asp Gly Ser Asn Lys Asn Tyr Ala Asp Ser Val
50 55 60

Lys Gly Arg Phe Thr Ile Ser Arg Asp Asn Ser Lys Asn Thr Leu Phe
65 70 75 80

Leu Gln Met Asn Ser Leu Arg Val Glu Asp Thr Ala Val Tyr Tyr Cys
85 90 95

Ala Lys Gly Gly Asn Ala Leu Tyr Ser Ser Gly Trp Pro Asp Asp Gly

```
            100                 105                 110

Phe Asp Ile Arg Gly Gln Gly Thr Met Val Thr Val Ser Ser
        115                 120                 125


<210> SEQ ID NO 145
<211> LENGTH: 117
<212> TYPE: PRT
<213> ORGANISM: Homo sapiens

<400> SEQUENCE: 145

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Ala Arg Gln Ala Pro Gly Lys Gly Leu Glu Trp Val
        35                  40                  45

Ala Val Ile Ser Tyr Asp Gly Asn Ser Lys Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Asp Asp Thr Ala Val Tyr Tyr Cys
                85                  90                  95

Ala Lys Gly Leu Trp Pro Pro Met Asp Val Arg Gly Gln Gly Thr Thr
            100                 105                 110

Val Thr Val Ser Ser
        115


<210> SEQ ID NO 146
<211> LENGTH: 124
<212> TYPE: PRT
<213> ORGANISM: Homo sapiens

<400> SEQUENCE: 146

Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Thr Trp Val Arg Gln Val Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ala Leu Tyr His Asn Gly Met Asp
            100                 105                 110

Met Gly Gly Gln Gly Thr Thr Val Thr Val Ser Ser
        115                 120


<210> SEQ ID NO 147
<211> LENGTH: 120
<212> TYPE: PRT
<213> ORGANISM: Homo sapiens

<400> SEQUENCE: 147

Lys Cys Ser Trp Trp Ser Leu Gly Glu Val Lys Lys Pro Gly Ala Ser
1               5                   10                  15
```

Val Lys Val Ser Cys Lys Ala Ser Gly Tyr Thr Phe Thr Ser Tyr Asp
20 25 30

Ile Asn Trp Val Arg Gln Ala Thr Gly Gln Gly Leu Glu Trp Met Gly
35 40 45

Trp Met Asn Pro Asn Ser Gly Asn Thr Gly Tyr Ala Gln Lys Phe Gln
50 55 60

Gly Arg Val Thr Met Thr Arg Asn Thr Ser Ile Ser Thr Ala Tyr Met
65 70 75 80

Glu Leu Ser Ser Leu Arg Ser Glu Asp Thr Ala Val Tyr Tyr Cys Ala
85 90 95

Arg Gly Asn Gly Pro Gly Ile Thr Gly Thr Thr Asp Tyr Trp Gly Gln
100 105 110

Gly Thr Leu Val Thr Val Ser Ser
115 120

<210> SEQ ID NO 148
<211> LENGTH: 119
<212> TYPE: PRT
<213> ORGANISM: Homo sapiens

<400> SEQUENCE: 148

Glu Val Gln Leu Val Glu Ser Gly Gly Gly Val Val Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Asn Trp Asn Gly Asp Arg Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Gly Arg Glu Asn Val Ile Val Pro Ala Ala Thr Tyr Trp Gly Gln Gly
100 105 110

Thr Leu Val Thr Val Ser Ser
115

<210> SEQ ID NO 149
<211> LENGTH: 381
<212> TYPE: DNA
<213> ORGANISM: Homo sapiens

<400> SEQUENCE: 149
gaggtgcagc tggtggagtc tgggggaggc gtggtccagc ctgggaggtc cctgagactc 60
tcctgtgcag cctctggatt ctccttcagt ggctatggca tgcactgggt ccgccaggct 120
ccaggcaagg gactggagtg ggtggcatat atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaagatccg 300
gcctggggat tacgtttggg ggagtcatcg tcctatgatt ttgatatctg gggccaaggg 360
acaatggtca ctgtctcttc a 381

<210> SEQ ID NO 150
<211> LENGTH: 381

<212> TYPE: DNA
<213> ORGANISM: Homo sapiens

<400> SEQUENCE: 150
gaggtgcagc tggtggagtc tgggggaggc gtggtccagc ctgggaggtc cctgagactc 60
tcctgtgcag cctctggatt ctccttcagt ggctatggca tgcactgggt ccgccaggct 120
ccaggcaagg gactggagtg ggtggcatat atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaagatccg 300
gcctggggat tacgtttggg ggagtcatcg tcctatgatt ttgatatctg gggccaaggg 360
acaatggtca ctgtctcttc a 381

<210> SEQ ID NO 151
<211> LENGTH: 381
<212> TYPE: DNA
<213> ORGANISM: Homo sapiens

<400> SEQUENCE: 151
gaggtgcagc tggtggagtc tgggggaggc gtggtccagc ctgggaggtc cctgagactc 60
tcctgtgcag cctctggatt cagcttcagt ggctatggca tgcactgggt ccgccaggct 120
ccaggcaagg ggctggagtg ggtggcacat atatcatatg atggaagtaa tagatactat 180
gcagaatccg tgaagggccg attcaccatc tccagagaga attccaagaa cacgctgtct 240
ctgcaaatga acagcctgag agctgaggac acggctgtgt attactgtgc gaaagatccg 300
gcctggggat tacgtttggg ggagttatcg tcctatgatt ttgacatttg gggccaaggg 360
acaatggtca ctgtctcttc a 381

<210> SEQ ID NO 152
<211> LENGTH: 381
<212> TYPE: DNA
<213> ORGANISM: Homo sapiens

<400> SEQUENCE: 152
caggtcacct tgaaggagtc tgggggaggc gtggtccagc ctgggaggtc cctgaaactc 60
tcctgtgcag cctctggatt ctccttcagt ggctatggca tgcactgggt ccgccaggct 120
ccaggcaagg ggctggagtg ggtggcagtt atatcatatg atggaagtaa tagatactat 180
gcagactccg tgaagggccg attcaccatc tccagagaca attccaagaa cacgctgtct 240
ctgcaaatga acagcctgag agctgaggac acggctgtgt attactgtgc gagagatccg 300
gcctggggat tacgtttggg ggagttatcg tcctatgatt ttgaaatctg gggccaaggg 360
acaatggtca ccgtctcctc a 381

<210> SEQ ID NO 153
<211> LENGTH: 381
<212> TYPE: DNA
<213> ORGANISM: Homo sapiens

<400> SEQUENCE: 153
caggtgcagc tggtggagtc tgggggaggc gtggtccagc ctgggaggtc cctgagactc 60
tcctgtgcag cctctggatt ctccttcagt ggctatggca tgcactgggt ccgccaggct 120
ccaggcaagg ggctggagtg ggtggcagtt atatcatatg atggaagtaa tagatactat 180
gcagactccg tgaagggccg attcaccatc tccagagaca attccaagaa cacactgtct 240

-continued

```
ctgcaaatga acagcctgag agctgaggac acggctgtgt attactgtgc gaaagatccg    300

gcctggggat tacgtttggg ggagttatcg tcctatgatt ttgaaatttg gggccaaggg    360

acaatggtca ccgtctcttc a                                              381


<210> SEQ ID NO 154
<211> LENGTH: 381
<212> TYPE: DNA
<213> ORGANISM: Homo sapiens

<400> SEQUENCE: 154

gaagtgcagc tggtggagtc tgggggaggc gtggtccagc ctgggaggtc cctgagactc     60

tcctgtgcag cctctggatt ctccttcagt ggctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctatat    240

ctgcaaatga acagcctgag agctgaggac acggctgtgt attactgtgc gaaagatccg    300

gcctggggat tacgtttggg ggaactatcg tcctataaat ttgaaatctg gggccaaggg    360

acaatggtca ccgtctcttc a                                              381


<210> SEQ ID NO 155
<211> LENGTH: 381
<212> TYPE: DNA
<213> ORGANISM: Homo sapiens

<400> SEQUENCE: 155

gaggtgcagc tggtggagtc tgggggaggc gtggtccagc ctgggaggtc cctgagactc     60

tcctgtgcag cctctggatt ctccttcagt ggctatggca tgcactgggt ccgccaggct    120

ccaggcaagg ggctggagtg ggtggcactt atatcatatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gaaagatccg    300

gcctggggat tacgtttggg ggagcaatcg tcctatgctt ttgatatctg gggccaaggg    360

acaatggtca ccgtctcctc a                                              381


<210> SEQ ID NO 156
<211> LENGTH: 381
<212> TYPE: DNA
<213> ORGANISM: Homo sapiens

<400> SEQUENCE: 156

caggtgcagc tggtggagtc tgggggaggc gtggtccagc ctgggaggtc cctgagactc     60

tcctgtgcag cctctggatt ctccttcagt ggctatggca tgcactgggt ccgccaggct    120

ccaggcaagg ggctggagtg ggtgtcagtt atatcatatg atggaagtaa taaatactat    180

gcagactccg tgaagggccg attcaccatc tccagagaca attccaagaa cacgctgtat    240

ctgcaaatga acagcctgag aactgaggac acggctgtgt attactgtgc gaaagatccg    300

gcctggggat tacgtttggg ggagcaatcg tcctatgctt ttgaaatctg gggccaaggt    360

acaatggtca ccgtctcctc a                                              381


<210> SEQ ID NO 157
<211> LENGTH: 381
<212> TYPE: DNA
<213> ORGANISM: Homo sapiens

<400> SEQUENCE: 157
```

```
gaggtgcagc tgttggagtc tgggggaggc gtggtccagc ctgggaggtc cctgagactc     60

tcctgtgcag cctctggatt ctccttcagt ggctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctgtat    240

ctgcaaatga acagcctgag agttgaggac acggctgtgt attactgtgc gaaagatccg    300

gcctggggat tacgtttggg ggagcaatcg tcctatgctt ttgaaatccg gggccagggg    360

acaacggtca ccgtctcttc a                                              381
```

```
<210> SEQ ID NO 158
<211> LENGTH: 381
<212> TYPE: DNA
<213> ORGANISM: Homo sapiens

<400> SEQUENCE: 158

gaggtgcagc tggtggagtc tgggggaggc gtggtccagc ctgggaggtc cctgagactc     60

tcctgtgcag cctctggatt cacctttagt ggctatggca tgcactgggt ccgccaggct    120

ccaggcaagg ggctggagtg ggtggcatat atatcatatg atggaagtaa tagatactat    180

gcagactccg tgaagggccg attcaccatc tccagagaca attccaagaa gacgctgtct    240

ctgcaaatga acagcctgag agctgaggac acggctgtgt attactgtgc gaaagatccg    300

gcctggggat tacgtttggg ggagtcatcg tcatatgatt ttgatatctg gggccaaggg    360

acaatggtca ccgtctcctc a                                              381
```

```
<210> SEQ ID NO 159
<211> LENGTH: 381
<212> TYPE: DNA
<213> ORGANISM: Homo sapiens

<400> SEQUENCE: 159

gaggtgcagc tggtggagtc tgggggaggc gtggtccagc ctgggaggtc cctgagactc     60

tcctgtgcag cctctggatt ctccttcagt ggctatggcc tccactgggt ccgccaggct    120

ccaggcaagg gactggagtg ggtggcatat atatcatatg acgagagtaa taaatactat    180

gcacccagcg tgaagggccg attcaccatc tccagagaca attccaagaa cacgctgtat    240

ctgcaaatga acagcctgag agctgaggac acggctgtgt attactgtgc gaaagatccg    300

gcctggggat tacgtttggg ggagtcatcg tcctatgatt ttgatatctg gggccaaggg    360

acaatggtca ccgtctcctc a                                              381
```

```
<210> SEQ ID NO 160
<211> LENGTH: 381
<212> TYPE: DNA
<213> ORGANISM: Homo sapiens

<400> SEQUENCE: 160

gaggtgcagc tggtggagtc tgggggaggc gtggtccagc ctgggaggtc cctgagactc     60

tcctgtgcag cctctggatt ctccttcagt ggctatggca tgcactgggt ccgccaggct    120

ccaggcaagg gactggagtg ggtggcatat atatcatatg ataagagtaa taaatactat    180

gcagacaagg tgaagggccg attcaccatc tccagagaca attccaagaa cacgctgtat    240

ctgcaaatga acagcctgag agctgaggac acggctgtgt attactgtgc gaaagatccg    300

gcctggggat tacgtttggg ggagtcatcg tcctatgatt ttgatatctg gggccaaggg    360
```

acaatggtca ctgtctcttc a 381

<210> SEQ ID NO 161
<211> LENGTH: 381
<212> TYPE: DNA
<213> ORGANISM: Homo sapiens

<400> SEQUENCE: 161
gaggtgcagc tggtggagtc tgggggaggc gtggtccagc ctgggaggtc cctgagactc 60
tcctgtgcag cctctggatt ctccttcagt ggctatggcc tccactgggt ccgccaggct 120
ccaggcaagg gactggagtg ggtggcatat atatcatatg atgcgagtaa taaatactat 180
gcagacaacg tgaagggccg attcaccatc tccagagaca attccaagaa cacgctgtat 240
ctgcaaatga acagcctgag agctgaggac acggctgtgt attactgtgc gaaagatccg 300
gcctggggat tacgtttggg ggagtcatcg tcctatgatt ttgatatctg gggccaaggg 360
acaatggtca ctgtctcttc a 381

<210> SEQ ID NO 162
<211> LENGTH: 381
<212> TYPE: DNA
<213> ORGANISM: Homo sapiens

<400> SEQUENCE: 162
gaggtgcagc tggtggagtc tgggggaggc gtggtccagc ctgggaggtc cctgagactc 60
tcctgtgcag cctctggatt ctccttcagt ggctatggcg tgcactgggt ccgccaggct 120
ccaggcaagg gactggagtg ggtggcatat atatcatatg atgcgagtaa taaatactat 180
gcagacaacg tgaagggccg attcaccatc tccagagaca attccaagaa cacgctgtat 240
ctgcaaatga acagcctgag agctgaggac acggctgtgt attactgtgc gaaagatccg 300
gcctggggat tacgtttggg ggagtcatcg tcctatgatt ttgatatctg gggccaaggg 360
acaatggtca ctgtctcttc a 381

<210> SEQ ID NO 163
<211> LENGTH: 381
<212> TYPE: DNA
<213> ORGANISM: Homo sapiens

<400> SEQUENCE: 163
gaggtgcagc tggtggagtc tgggggaggc gtggtccagc ctgggaggtc cctgagactc 60
tcctgtgcag cctctggatt ctccttcagt ggctatggcc tccactgggt ccgccaggct 120
ccaggcaagg gactggagtg ggtggcatat atatcatatg ataagagtaa taaatactat 180
gcagacaagg tgaagggccg attcaccatc tccagagaca attccaagaa cacgctgtat 240
ctgcaaatga acagcctgag agctgaggac acggctgtgt attactgtgc gaaagatccg 300
gcctggggat tacgtttggg ggagtcatcg tcctatgatt ttgatatctg gggccaaggg 360
acaatggtca ctgtctcttc a 381

<210> SEQ ID NO 164
<211> LENGTH: 381
<212> TYPE: DNA
<213> ORGANISM: Homo sapiens

<400> SEQUENCE: 164
gaggtgcagc tggtggagtc tgggggaggc gtggtccagc ctgggaggtc cctgagactc 60
tcctgtgcag cctctggatt ctccttcagt ggctatggcg cgcactgggt ccgccaggct 120

```
ccaggcaagg gactggagtg ggtggcatat atatcatatg ataagagtaa taaatactat    180

gcagacaagg tgaagggccg attcaccatc tccagagaca attccaagaa cacgctgtat    240

ctgcaaatga acagcctgag agctgaggac acggctgtgt attactgtgc gaaagatccg    300

gcctggggat tacgtttggg ggagtcatcg tcctatgatt ttgatatctg gggccaaggg    360

acaatggtca ctgtctcttc a                                              381
```

<210> SEQ ID NO 165
<211> LENGTH: 381
<212> TYPE: DNA
<213> ORGANISM: Homo sapiens

<400> SEQUENCE: 165

```
gaggtgcagc tggtggagtc tgggggaggc gtggtccagc ctgggaggtc cctgagactc    60

tcctgtgcag cctctggatt ctccttcagt ggctatggca tgcactgggt ccgccaggct   120

ccaggcaagg gactggagtg ggtggcatat atatcatatg atgcgagtaa taaatactat   180

gcagacaacg tgaagggccg attcaccatc tccagagaca attccaagaa cacgctgtat   240

ctgcaaatga acagcctgag agctgaggac acggctgtgt attactgtgc gaaagatccg   300

gcctggggat tacgtttggg ggagtcatcg tcctatgatt ttgatatctg gggccaaggg   360

acaatggtca ctgtctcttc a                                             381
```

<210> SEQ ID NO 166
<211> LENGTH: 381
<212> TYPE: DNA
<213> ORGANISM: Homo sapiens

<400> SEQUENCE: 166

```
gaggtgcagc tggtggagtc tgggggaggc gtggtccagc ctgggaggtc cctgagactc    60

tcctgtgcag cctctggatt ctccttcagt ggctatggcc agcactgggt ccgccaggct   120

ccaggcaagg gactggagtg ggtggcatat atatcatatg atgcgagtaa taaatactat   180

gcagacaacg tgaagggccg attcaccatc tccagagaca attccaagaa cacgctgtat   240

ctgcaaatga acagcctgag agctgaggac acggctgtgt attactgtgc gaaagatccg   300

gcctggggat tacgtttggg ggagtcatcg tcctatgatt ttgatatctg gggccaaggg   360

acaatggtca ctgtctcttc a                                             381
```

<210> SEQ ID NO 167
<211> LENGTH: 381
<212> TYPE: DNA
<213> ORGANISM: Homo sapiens

<400> SEQUENCE: 167

```
gaggtgcagc tggtggagtc tgggggaggc gtggtccagc ctgggaggtc cctgagactc    60

tcctgtgcag cctctggatt ctccttcagt ggctatggct ccactgggt ccgccaggct    120

ccaggcaagg gactggagtg ggtggcatat atatcatatg atgcgagtaa taaatactat   180

gcagacaacg tgaagggccg attcaccatc tccagagaca attccaagaa cacgctgtat   240

ctgcaaatga acagcctgag agctgaggac acggctgtgt attactgtgc gaaagatccg   300

gcctggggat tacgtttggg ggagtcatcg tcctatgatt ttgatatctg gggccaaggg   360

acaatggtca ctgtctcttc a                                             381
```

<210> SEQ ID NO 168

<211> LENGTH: 381
<212> TYPE: DNA
<213> ORGANISM: Homo sapiens

<400> SEQUENCE: 168
gaggtgcagc tggtggagtc tgggggaggc gtggtccagc ctgggaggtc cctgagactc 60
tcctgtgcag cctctggatt cagcttcagt ggctatggca tgcactgggt ccgccaggct 120
ccaggcaagg ggctggagtg ggtggcaatt atatcatatg atggaagtaa tagatactat 180
gcagactccg tgaagggccg attcaccatc tccagagaca attccaagaa cacgctgtct 240
ctgcaaatga acagcctgag agctgaggac acggctgtgt attactgtgc gaaagatccg 300
gcctggggat tacgtttggg ggagtcatcg tcctatgatt ttgaaatttg gggccaaggg 360
acaatggtca ccgtctcctc a 381

<210> SEQ ID NO 169
<211> LENGTH: 381
<212> TYPE: DNA
<213> ORGANISM: Homo sapiens

<400> SEQUENCE: 169
caggtgcagc tggtggagtc tgggggaggc gtggtccagc ctgggaggtc cctgaaactc 60
tcctgtgcag cctctggatt ctccttcagt ggctatggca tgcactgggt ccgccaggct 120
ccaggcaagg ggctggagtg ggtggcagtt atatcatatg atggaagtaa tagatactat 180
gcagactccg tgaagggccg attcaccatc tccagagaca attccaagaa cacgctgtct 240
ctacaaatga acagcctgag agctgaggac acggctgtgt attactgtgc gaaagatccg 300
gcctggggat tacgtttggg gaaattatcg tcctatgatt ttgaaatctg gggccaaggg 360
acaatggtca ctgtctcttc a 381

<210> SEQ ID NO 170
<211> LENGTH: 381
<212> TYPE: DNA
<213> ORGANISM: Homo sapiens

<400> SEQUENCE: 170
gaggtgcagc tggtggagtc tgggggaggc gtggtccagc ctgggaggtc cctgagactc 60
tcctgtgcag cctctggatt ctccttcagt ggctatggca cgcactgggt ccgccaggct 120
ccaggcaagg gactggagtg ggtggcatat atatcatatg acgggagtaa taaatactat 180
gcagccccgg tgaagggccg attcaccatc tccagagaca attccaagaa cacgctgtat 240
ctgcaaatga acagcctgag agctgaggac acggctgtgt attactgtgc gaaagacgcg 300
gcctggggat tacgtttggg ggagtcatcg tcctatgatt ttgatatctg gggccaaggg 360
acaatggtca ctgtctcttc a 381

<210> SEQ ID NO 171
<211> LENGTH: 381
<212> TYPE: DNA
<213> ORGANISM: Homo sapiens

<400> SEQUENCE: 171
gaggtgcagc tggtggagtc tgggggaggc gtggtccagc ctgggaggtc cctgagactc 60
tcctgtgcag cctctggatt ctccttcagt ggctatggca cgcactgggt ccgccaggct 120
ccaggcaagg gactggagtg ggtggcatat atatcatatg acgagagtaa taaatactat 180
gcatccagcg tgaagggccg attcaccatc tccagagaca attccaagaa cacgctgtat 240
ctgcaaatga acagcctgag agctgaggac acggctgtgt attactgtgc gaaagaccgg   300
gcctggggat tacgtttggg ggagtcatcg tcctatgatt ttgatatctg gggccaaggg   360
acaatggtca ctgtctcttc a                                             381

<210> SEQ ID NO 172
<211> LENGTH: 381
<212> TYPE: DNA
<213> ORGANISM: Homo sapiens

<400> SEQUENCE: 172
gaggtgcagc tggtggagtc tgggggaggc gtggtccagc ctgggaggtc cctgagactc   60
tcctgtgcag cctctggatt ctccttcagt ggctatggca tgcactgggt ccgccaggct   120
ccaggcaagg gactggagtg ggtggcatat atatcatatg acgagagtaa taaatactat   180
gcaaggctgg tgaagggccg attcaccatc tccagagaca attccaagaa cacgctgtat   240
ctgcaaatga acagcctgag agctgaggac acggctgtgt attactgtgc gaaagacacg   300
gcctggggat tacgtttggg ggagtcatcg tcctatgatt ttgatatctg gggccaaggg   360
acaatggtca ctgtctcttc a                                             381

<210> SEQ ID NO 173
<211> LENGTH: 381
<212> TYPE: DNA
<213> ORGANISM: Homo sapiens

<400> SEQUENCE: 173
gaggtgcagc tggtggagtc tgggggaggc gtggtccagc ctgggaggtc cctgagactc   60
tcctgtgcag cctctggatt ctccttcagt ggctatggcc tccactgggt ccgccaggct   120
ccaggcaagg gactggagtg ggtggcatat atatcatatg acctgagtaa taaatactat   180 gcaaggggg tgaagggccg attcaccatc tccagagaca attccaagaa cacgctgtat   240
ctgcaaatga acagcctgag agctgaggac acggctgtgt attactgtgc gaaagacgtg   300
gcctggggat tacgtttggg ggagtcatcg tcctatgatt ttgatatctg gggccaaggg   360
acaatggtca ctgtctcctc a                                             381

<210> SEQ ID NO 174
<211> LENGTH: 369
<212> TYPE: DNA
<213> ORGANISM: Homo sapiens

<400> SEQUENCE: 174
gaggtgcagc tggtggagtc tgggggaggc gtggtccagc ctgggaggtc cctgagactc   60
tcctgtgcag cctctggatt ccccttaatt agctatggca tgcactgggt ccgccaggct   120
ccaggcaagg ggctggagtg ggtggcattt atgacatatg atggaagtaa tagatactat   180
gcagactccg tgaagggccg attcaccatc tccagagaca attccaagaa cacgctgtat   240
ctgcaaatga acagcctgag agatgaggac acggctctat attactgtgc gagagatcgt   300
atagtgggag gtagggtccc tgatgctttt gatatctggg gccaagggac aatggtcacc   360
gtctcttca                                                           369

<210> SEQ ID NO 175
<211> LENGTH: 369
<212> TYPE: DNA
<213> ORGANISM: Homo sapiens

<400> SEQUENCE: 175
gaggtgcagc tggtggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggactg ggtggcattt atatcatatg atggaagtaa taaatattat 180
gcagactccg tgaagggccg attcaccatc tccaaagaca attccaagaa cacgctgtat 240
ctgcaaatga acagcctgag agctgaggac acggctgtgt attactgtgc gaaagatcgt 300
atagtgggag ccagggtccc tgatgctttt gatatctggg gccaagggac aatggtcacc 360
gtctcctca 369

<210> SEQ ID NO 176
<211> LENGTH: 369
<212> TYPE: DNA
<213> ORGANISM: Homo sapiens

<400> SEQUENCE: 176
gaggtgcagc tggtggagtc tgggggaggc gtggtccagc ctgggaggtc cctgagactc 60
tcctgtgcag cctctggatt cccccctcatt agctatggca tgaactgggt ccgccaggct 120
ccaggcaagg ggctggagtg ggtggcattt atatcatatg atggaagtaa tagatactat 180
gcagactccg tgaagggccg attcaccatc tccagagaca attccaagaa cacgctgtat 240
ctgcaaatga acagcctgag agctgaggac acggctgtat attactgtgc gaaagatcgt 300
atagtgggag ctagggtccc tgatgctttt gatatctggg gccaagggac aatggtcacc 360
gtctcctca 369

<210> SEQ ID NO 177
<211> LENGTH: 369
<212> TYPE: DNA
<213> ORGANISM: Homo sapiens

<400> SEQUENCE: 177
gaggtgcagc tggtggagtc tgggggaggc gcggtccagc ctgggaggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatattat 180
gcagactctg tgaagggccg attcaccatc tccagagaca attccaagaa cacgctttat 240
ctgcaaatga acagcctgag acctgaggac acggctgtat attactgtgc gaaagatcgt 300
attgtgggag ctagggtccc tgatgcttat gatatctggg gccaagggac aatggtcacc 360
gtctcctca 369

<210> SEQ ID NO 178
<211> LENGTH: 369
<212> TYPE: DNA
<213> ORGANISM: Homo sapiens

<400> SEQUENCE: 178
caggtgcagc tggtggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgctttat 240
ctgcaaatga acagcctgag acctgaggac acggctgtat attactgtgc gaaagatcgt 300
attgtgggag ctagggtccc tgatgcttat gatatctggg gccaagggac aatggtcacc 360
gtctcctca 369

<210> SEQ ID NO 179
<211> LENGTH: 369
<212> TYPE: DNA
<213> ORGANISM: Homo sapiens

<400> SEQUENCE: 179
gaggtgcagc tgttggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgctttat 240
ctgcaaatga acagcctgag acctgaggac acggctgtat attactgtgc gaaagatcgt 300
attgtgggag ctagggtccc tgatgcttat gatatctggg gccaagggac aatggtcacc 360
gtctcctca 369

<210> SEQ ID NO 180
<211> LENGTH: 369
<212> TYPE: DNA
<213> ORGANISM: Homo sapiens

<400> SEQUENCE: 180
caggtgcagc tggtggagtc tgggggaggc ttggtacagc ctggggggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgcttcat 240
ctgcaaatgg acagcctgag acctgaggac acggctgtat attactgtgc gaaagatcgt 300
attgtgggag ctagggtccc tgatgcttat gatatctggg gccaagggac aatggtcact 360
gtctcttca 369

<210> SEQ ID NO 181
<211> LENGTH: 369
<212> TYPE: DNA
<213> ORGANISM: Homo sapiens

<400> SEQUENCE: 181
gaagtgcagc tggtggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgctttat 240
ctgcaaatga acagcctgag acctgaggac acggctgtat attactgtgc gaaagatcgt 300
attgtgggag ctagggtccc tgatgcttat gatatctggg gccagggaac cctggtcact 360
gtctcctca 369

<210> SEQ ID NO 182
<211> LENGTH: 369
<212> TYPE: DNA
<213> ORGANISM: Homo sapiens

<400> SEQUENCE: 182
caggtgcagc tggtggagtc tgggggaggc gtggtccagc ctgggaggtc cctgagactc 60

-continued

```
tcctgtgcag cctctggatt cccccttaatt agctatggca tgaattgggt ccgccaggct    120

ccaggcaagg ggctggagtg ggtggcattt atatcatatg atggaagtaa tagatactat    180

gcagactccg tgaagggccg attcaccatc tccagagaca attccaagaa cacgctgtat    240

ctgcaaatga acagcctgag acctgaggac acggctgtat attactgtgc gaaagatcgt    300

attgtgggag ctagggtccc tgatgcttat gatatctggg gccaagggac aatggtcacc    360

gtctcttca                                                            369
```

<210> SEQ ID NO 183
<211> LENGTH: 369
<212> TYPE: DNA
<213> ORGANISM: Homo sapiens

<400> SEQUENCE: 183

```
caggtgcagc tggtggagtc tgggggaggc gtggtccagc ctgggaggtc cctgagactc     60

tcctgtgcag cctctggatt ccccttaatt agctatggca tgaattgggt ccgccaggct    120

ccaggcaagg ggctggactg ggtggcattt ataacatatg atggaagtaa tagatactat    180

gcagactccg tgaagggccg attcaccatc tccagagaca attccaagaa cacgcttcat    240

ctgcaaatga acagcctgag acctgaggac acggctgtat attactgtgc gaaagatcgt    300

attgtgggag ctagggtccc tgatgcttat gatatctggg gccaagggac aatggtcact    360

gtctcctca                                                            369
```

<210> SEQ ID NO 184
<211> LENGTH: 369
<212> TYPE: DNA
<213> ORGANISM: Homo sapiens

<400> SEQUENCE: 184

```
gaggtgcagc tggtggagtc tgggggaggc gtggtccagc ctgggaggtc cctgagactc     60

tcctgtgcag cctctggatt ccccttaatt agctatggca tgaattgggt ccgccaggct    120

ccaggcaagg ggctggactg ggtggcattt ataacatatg atggaagtaa tagatactat    180

gcagactccg tgaagggccg attcaccatc tccagagaca attccaagaa cacgcttcat    240

ctgcaaatga acagcctgag acctgaggac acggctgtat attactgtgc gaaagatcgt    300

attgtgggag ctagggtccc tgatgcttat gatatctggg gccaagggac aatggtcact    360

gtctcctca                                                            369
```

<210> SEQ ID NO 185
<211> LENGTH: 369
<212> TYPE: DNA
<213> ORGANISM: Homo sapiens

<400> SEQUENCE: 185

```
gaggtgcagc tggtggagtc tgggggaggc gtggtccagc ctgggaggtc cctgagactc     60

tcctgtgcag cctctggatt ccccttaatt agctatggca tgaattgggt ccgccaggct    120

ccaggcaagg ggctggactg ggtggcattt ataacatatg atggaagtaa tagatactat    180

gcagactccg tgaagggccg attcaccatc tccagagaca attccaagaa cacgctttat    240

ctgcaaatga acagcctgag acctgaggac acggctgtat attactgtgc gaaagatcgt    300

attgtgggag ctagggtccc tgatgcttat gatatctggg gccaagggac aatggtcacc    360

gtctcctca                                                            369
```

<210> SEQ ID NO 186
<211> LENGTH: 369
<212> TYPE: DNA
<213> ORGANISM: Homo sapiens

<400> SEQUENCE: 186
caggtgcagc tggtggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgctttat 240
ctgcaaatga acagcctgag acctgaggac acggctgtat attactgtgc gaaagatcgt 300
attgtgggag ctagggtccc tgatgcttat gatatctggg gccaagggac aatggtcact 360
gtctcctca 369

<210> SEQ ID NO 187
<211> LENGTH: 369
<212> TYPE: DNA
<213> ORGANISM: Homo sapiens

<400> SEQUENCE: 187
gaggtgcagc tggtggagtc tgggggaggt gtggtacggc ctgggggtc cctgagactc 60 tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgcttcat 240
ctgcaaatga acagcctgag acctgaggac acggctgtat attactgtgc gaaagatcgt 300
attgtgggag ctagggtccc tgatgcttat gatatctggg gccaagggac aatggtcact 360
gtctcctca 369

<210> SEQ ID NO 188
<211> LENGTH: 369
<212> TYPE: DNA
<213> ORGANISM: Homo sapiens

<400> SEQUENCE: 188
gaagtgcagc tggtggagtc tgggggaggc ttggtccagc ctgggggtc cctgagactc 60 tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgcttcat 240
ctgcaaatga acagcctgag acctgaggac acggctgtat attactgtgc gaaagatcgt 300
attgtgggag ctagggtccc tgatgcttat gatatctggg gccaagggac aatggtcacc 360
gtctcctca 369

<210> SEQ ID NO 189
<211> LENGTH: 369
<212> TYPE: DNA
<213> ORGANISM: Homo sapiens

<400> SEQUENCE: 189
gaggtgcagc tgttggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatactat 180

-continued gcagactccg tgaagggccg attcaccatc tccagagaca attccaagaa cacgcttcat 240
ctgcaaatga acagcctgag acctgaggac acggctgtat attactgtgc gaaagatcgt 300
attgtgggag ctagggtccc tgatgcttat gatatctggg gccaagggac aatggtcacc 360
gtctcctca 369

<210> SEQ ID NO 190
<211> LENGTH: 369
<212> TYPE: DNA
<213> ORGANISM: Homo sapiens

<400> SEQUENCE: 190
gaggtgcagc tgttggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgctttat 240
ctgcaaatga acagcctgaa acctgaggac acggctgtat attactgtgc gaaagatcgt 300
attgtgggag ctagggtccc tgatgcttat gatatctggg gccaagggac aatggtcacc 360
gtctcctca 369

<210> SEQ ID NO 191
<211> LENGTH: 369
<212> TYPE: DNA
<213> ORGANISM: Homo sapiens

<400> SEQUENCE: 191
gaggtgcagc tggtggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggactg ggtggcattt ataacatatg atggaagtaa tagatactat 180
gcagactccg tgaagggccg attcaccatc tccagagaca attccaagaa cacgctttat 240
ctgcaaatga acagcctgaa acctgaggac acggctgtat attactgtgc gaaagatcgt 300
attgtgggag ctagggtccc tgatgcttat gatatctggg gccaagggac aatggtcacc 360
gtctcctca 369

<210> SEQ ID NO 192
<211> LENGTH: 369
<212> TYPE: DNA
<213> ORGANISM: Homo sapiens

<400> SEQUENCE: 192
caggtgcagc tggtggagtc tgggggaggc gtggtccagc ctgggaggtc cctgagactc 60
tcctgtgcag cctctggatt ccccttaatt agctatggca tgcactgggt ccgccaggct 120
ccaggcaagg ggctggagtg ggtggcattt atgacatatg atggaagtaa tagatactat 180
gcagacgccg tgaagggccg attcaccatc tccagagaca attccaagaa cacgctgtat 240
ctgcaaatga acagcctgag agctgaggac acggctgtgt attactgtgc gagagatcgt 300
atagtgggag gtagggtccc tgatgctttt gatatctggg gccaagggac aatggtcacc 360
gtctcttca 369

<210> SEQ ID NO 193
<211> LENGTH: 369
<212> TYPE: DNA
<213> ORGANISM: Homo sapiens

<400> SEQUENCE: 193
caggtgcagc tggtggagtc tgggggaggc gtggtccagc ctgggaggtc cctgagactc 60
tcctgtgcag cctctggatt ccccttaatt agctatggca tgcactgggt ccgccaggct 120
ccaggcaagg ggctggagtg ggtggcattt cagacatatg atggcagtaa tagatactat 180
gcagacgccg tgaagggccg attcaccatc tccagagaca attccaagaa cacgctgtat 240
ctgcaaatga acagcctgag agctgaggac acggctgtgt attactgtgc gagagatcgt 300
atagtgggag gtagggtccc tgatgctttt gatatctggg gccaagggac aatggtcacc 360
gtctcttca 369

<210> SEQ ID NO 194
<211> LENGTH: 369
<212> TYPE: DNA
<213> ORGANISM: Homo sapiens

<400> SEQUENCE: 194
caggtgcagc tggtggagtc tgggggaggc gtggtccagc ctgggaggtc cctgagactc 60
tcctgtgcag cctctggatt ccccttaatt agctatggca tgcactgggt ccgccaggct 120
ccaggcaagg ggctggagtg ggtggcattt cagacatatg atggcagtaa tagatactat 180
gcagactccg tgaagggccg attcaccatc tccagagaca attccaagaa cacgctgtat 240
ctgcaaatga acagcctgag agctgaggac acggctgtgt attactgtgc gagagatcgt 300
atagtgggag gtagggtccc tgatgctttt gatatctggg gccaagggac aatggtcacc 360
gtctcttca 369

<210> SEQ ID NO 195
<211> LENGTH: 369
<212> TYPE: DNA
<213> ORGANISM: Homo sapiens

<400> SEQUENCE: 195
caggtgcagc tggtggagtc tgggggaggc gtggtccagc ctgggaggtc cctgagactc 60
tcctgtgcag cctctggatt ccccttaatt agctatggca tgcactgggt ccgccaggct 120
ccaggcaagg ggctggagtg ggtggcattt cagacatatg atgccagtaa tagatactat 180
gcagacgccg tgaagggccg attcaccatc tccagagaca attccaagaa cacgctgtat 240
ctgcaaatga acagcctgag agctgaggac acggctgtgt attactgtgc gagagatcgt 300
atagtgggag gtagggtccc tgatgctttt gatatctggg gccaagggac aatggtcacc 360
gtctcttca 369

<210> SEQ ID NO 196
<211> LENGTH: 369
<212> TYPE: DNA
<213> ORGANISM: Homo sapiens

<400> SEQUENCE: 196
caggtgcagc tggtggagtc tgggggaggc gtggtccagc ctgggaggtc cctgagactc 60
tcctgtgcag cctctggatt ccccttaatt agctatggca tgaattgggt ccgccaggct 120
ccaggcaagg ggctggagtg ggtggcattt ataacatatg atggaagtaa tagatactat 180
gcagactccg tgaagggccg attcaccatc tccagagaca attccaagaa cacgctttat 240
ctgcaaatga acagcctgag agctgaggac acggctgtat attactgtgc gaaagatcgt 300
attgtgggag ctagggtccc tgatgcttat gatatctggg gccaagggac aatggtcact 360
gtctcctca 369

<210> SEQ ID NO 197
<211> LENGTH: 368
<212> TYPE: DNA
<213> ORGANISM: Homo sapiens

<400> SEQUENCE: 197
aggtgcagct ggtggagtct gggggaggcg tggtccagcc tgggaggtcc ctgagactct 60
cctgtgcagc ctctggattc cccttaatta gctatggcat gaattgggtc cgccaggctc 120
caggcaaggg gctggagtgg gtggcattta taacatatga tggaagtaat agatactatg 180
cagactccgt gaagggccga ttcaccatct ccagagacaa ttccaagaac acgctttatc 240
tgcaaatgaa cagcctgaga gctgaggaca cggctgtata ttactgtgcg aaagatcgta 300
ttgtgggagc tagggtccct gatgcttatg atatctgggg ccaagggaca atggtcactg 360
tctcctca 368

<210> SEQ ID NO 198
<211> LENGTH: 369
<212> TYPE: DNA
<213> ORGANISM: Homo sapiens

<400> SEQUENCE: 198
caggtgcagc tggtggagtc tgggggaggc gtggtccagc ctgggaggtc cttgagactc 60
tcctgtgtag cctctggatt ccccttcatt agctatggca tgcactgggt ccgccaggct 120
ccaggcaagg ggcgggagtg ggtggcagtt atatcatatg atggaagtaa tagatactat 180
gcagactccg tgaagggccg attcaccatc tccagagaca attccaagaa cacgctgtat 240
ctgcaaatga acagcctgag acctgaggac acggctgtgt attattgtgc gaaagagagg 300
atttttggag tgcttacccc tgatgatttt gatatctggg gccaagggac aacggtcacc 360
gtctcctca 369

<210> SEQ ID NO 199
<211> LENGTH: 369
<212> TYPE: DNA
<213> ORGANISM: Homo sapiens

<400> SEQUENCE: 199
caggtgcagc tggtggagtc tgggggaggc gtggtccagc ctgggaggtc cctgagactc 60
tcctgtgcag cctctggatt ccccttcatt agctatggca tgcactgggt ccgccaggct 120
ccaggcaagg ggctggagtg ggtggcagtt atatcatatg atggaagtaa tagatactat 180
gcagactccg tgaagggccg attcaccatc tccagagaca attccaagaa cacgctgtat 240
ctgcaaatga acagcctgag acctgaggac acggctgtgt attactgtgc gaaagagagg 300
atttttggag tgcttacccc tgatgatttt gatatctggg gccaagggac aacggtcact 360
gtctcctca 369

<210> SEQ ID NO 200
<211> LENGTH: 369
<212> TYPE: DNA
<213> ORGANISM: Homo sapiens

<400> SEQUENCE: 200
gaggtgcagc tgttggagtc tgggggaggc gtggtccagc ctgggaggtc cctgagactc 60
tcctgtgcag cctctggatt ccccttcatt agctatggca tgcactgggt ccgccaggct 120
ccaggcaagg ggctggagtg ggtggcagtt atatcatatg atggagctaa tagatactat 180
gcagactccg tgaagggccg attcaccatc tccagagaca attccaagaa cacgctgtat 240
ctgcaaatga acagcctgag acctgaggac acggctgtgt attattgtgc gaaagagagg 300
atttttggcg tgcttacccc tgatgatttt gaaatctggg gccaagggac aacggtcacc 360
gtctcctca 369

<210> SEQ ID NO 201
<211> LENGTH: 369
<212> TYPE: DNA
<213> ORGANISM: Homo sapiens

<400> SEQUENCE: 201
gaggtgcagc tggtggagtc tgggggaggc gtggtccagc ctgggaggtc cctgagactc 60
tcctgtgcag cctctggatt caccttcact agctatggca tgcactgggt ccgccaggct 120
ccaggcaagg ggctggagtg ggtggcagtt atatcatatg atggaagtaa tagatactat 180
gcagactccg tgaagggccg attcaccatc tccagagaca attccaagaa cacgctgtat 240
ctgcaaatga acagcctgag acctgaggac acggctgtgt attactgtgc gaaagagagg 300
atttttggag cgcttacccc tgatgatttt gatatctggg gccaagggac aacggtcacc 360
gtctcttca 369

<210> SEQ ID NO 202
<211> LENGTH: 348
<212> TYPE: DNA
<213> ORGANISM: Homo sapiens

<400> SEQUENCE: 202
caggtgcagc tggtggagtc tgggggaggc gtggtccagc ctgggaggtc cctgagactc 60
tcctgtgcag cctctggatt caccttcaat aactatggca tgcactgggt ccgccaggct 120
ccaggcaagg ggctggagtg ggtggcaatt atatcatatg atggaaatac taaatattat 180
acagactccg tgaagggccg attcaccatc tccagagaca attccaagaa cacgctgtat 240
ctgcaaatga atagcctgag agttgaggac acggctgtgt attactgtgc gaaaggttta 300
tggccttcgg acgtctgggg ccaagggacc acggtcactg tctcttca 348

<210> SEQ ID NO 203
<211> LENGTH: 348
<212> TYPE: DNA
<213> ORGANISM: Homo sapiens

<400> SEQUENCE: 203
gaggtgcagc tggtggagtc tgggggaggc gtggtccagc ctgggaggtc cctgagactc 60
tcctgtgcag cctctggatt caccttcaat aactatggca tgcactgggt ccgccaggct 120
ccaggcaagg ggctggagtg ggtggcaatt atatcatatg atggaaatag taaatattat 180
acagactccg tgaagggccg attcaccatc tccagagaca attccaagaa cacgctgtat 240
ctgcaaatga atagcctgag agttgaggac acggctgtgt attactgtgc gaaaggttta 300
tggccttcgg acgtctgggg ccaagggacc acggtcaccg tctcctca 348

<210> SEQ ID NO 204
<211> LENGTH: 357
<212> TYPE: DNA

<213> ORGANISM: Homo sapiens

<400> SEQUENCE: 204
caggtgcagc tacaggagtc gggcccagga ctggtgaagc cttcacagac cctgtccctc 60
acctgcactg tctctggtgg ctccatcagc aatagtggtt attactggag ctgggtccgc 120
cagcacccag ggaaggacct ggagtggatt gggttcatct attacaatgg gagcatccac 180
tacaacccgt ccctcaagag tcgagttatc atatcagtag acacgtctaa gaaccagttc 240
tccctgaaaa tgaactctgt gactgccgcg gacacggccg tgtattactg tgcgagagac 300
ggggatgact acggtgacta cttgaggggc cagggaaccc tggtcaccgt ctcctca 357

<210> SEQ ID NO 205
<211> LENGTH: 357
<212> TYPE: DNA
<213> ORGANISM: Homo sapiens

<400> SEQUENCE: 205
caggtgcagc tgcaggagtc gggcccagga ctggtgaagc cttcacagac cctgtccctc 60
acctgcactg tctctggtgg ctccatcagc aatagtggtt attactggag ctggatccgc 120
cagcacccag ggaagggcct ggagtggatt gggttcatct attacaatgg gagcatccac 180
tacaacccgt ccctcaagag tcgagttatc atatcagtag acacgtctaa gaaccagttc 240
tccctgaaaa tgagctctgt gactgccgcg gacacggccg tgtattactg tgcgagagac 300
ggggatgact acggtgacta cttgaggggc cagggaaccc tggtcaccgt ctcctca 357

<210> SEQ ID NO 206
<211> LENGTH: 357
<212> TYPE: DNA
<213> ORGANISM: Homo sapiens

<400> SEQUENCE: 206
caggtgcagc tgcaggagtc gggcccagga ctggtgaagc cttcacagac cctgtccctc 60
acctgcactg tctctggtgg ctccatcagc aatagtggtt attactggag ctgggtccgc 120
cagcacccag ggaagggcct ggagtggatt gggttcatct attacaatgg gagcatccac 180
tacaacccgt ccctcaagag tcgagttatc atatcagtag acacgtctaa gaaccagttc 240
tccctgaaac tgaactctgt gactgccgcg gacacggccg tgtattactg tgcgagagac 300
ggggatgact acggtgacta cttgaggggc cagggaaccc tggtcaccgt ctcctca 357

<210> SEQ ID NO 207
<211> LENGTH: 357
<212> TYPE: DNA
<213> ORGANISM: Homo sapiens

<400> SEQUENCE: 207
caggtgcagc tgcaggagtc gggcccagga ctggtgaagc cttcacagac cctgtccctc 60
acctgcactg tctctggtgg ctccatcagc aatagtggtt attactggag ctggatccgc 120
cagcacccag ggaagggcct ggagtggatt gggttcatct attacaatgg gagcatccac 180
tacaacccgt ccctcaagag tcgagttatc atatcagtag acacgtctaa gaaccagttc 240
tccctgaaac tgagctctgt gactgccgcg gacacggccg tgtattactg tgcgagagac 300
ggggatgact acggtgacta cttgaggggc cagggaaccc tggtcaccgt ctcctca 357

<210> SEQ ID NO 208
<211> LENGTH: 357

<212> TYPE: DNA
<213> ORGANISM: Homo sapiens

<400> SEQUENCE: 208
caggtgcagc tgcaggagtc gggcccagga ctggtgaagc cttcacagac cctgtccctc 60
acctgcactg tctctggtgg ctccatcagc aatagtggtt attactggag ctgggtccgc 120
cagcacccag ggaagggcct ggagtggatt gggttcatct attacaatgg gagcatccac 180
tacaacccgt ccctcaagag tcgagttacc atatcagtag acacgtctaa gaaccagttc 240
tccctgaaaa tgagctctgt gactgccgcg gacacggccg tgtattactg tgcgagagac 300
ggggatgact acggtgacta cttgaggggc cagggaaccc tggtcaccgt ctcctca 357

<210> SEQ ID NO 209
<211> LENGTH: 357
<212> TYPE: DNA
<213> ORGANISM: Homo sapiens

<400> SEQUENCE: 209
caggtgcagc tgcaggagtc gggcccagga ctggtgaagc cttcacagac cctgtccctc 60
acctgcactg tctctggtgg ctccatcagc aatagtggtt attactggag ctgggtccgc 120
cagcacccag ggaagggcct ggagtggatt gggttcatct attacaatgg gagcatccac 180
tacaacccgt ccctcaagag tcgagttacc atatcagtag acacgtctaa gaaccagttc 240
tccctgaaac tgaactctgt gactgccgcg gacacggccg tgtattactg tgcgagagac 300
ggggatgact acggtgacta cttgaggggc cagggaaccc tggtcaccgt ctcctca 357

<210> SEQ ID NO 210
<211> LENGTH: 357
<212> TYPE: DNA
<213> ORGANISM: Homo sapiens

<400> SEQUENCE: 210
caggtgcagc tgcaggagtc gggcccagga ctggtgaagc cttcacagac cctgtccctc 60
acctgcactg tctctggtgg ctccatcagc aatagtggtt attactggag ctgggtccgc 120
cagcacccag ggaagggcct ggagtggatt gggttcatct attacaatgg gagcatccac 180
tacaacccgt ccctcaagag tcgagttacc atatcagtag acacgtctaa gaaccagttc 240
tccctgaaac tgagctctgt gactgccgcg gacacggccg tgtattactg tgcgagagac 300
ggggatgact acggtgacta cttgaggggc cagggaaccc tggtcaccgt ctcctca 357

<210> SEQ ID NO 211
<211> LENGTH: 357
<212> TYPE: DNA
<213> ORGANISM: Homo sapiens

<400> SEQUENCE: 211
gaggtgcagc tggtggagtc tgggggaggc ttggtccagc ctggggggtc cctgagactc 60
tcctgtgcag cctctggatt cacctttagt agctattgga tgtactgggt ccgccaggct 120
ccagggaagg ggctggagtg ggtggccaac ataaatcacg atggaagtga gaaatactat 180
gtggactctg tgaagggccg attcaccatc tccagagaca acgccaagaa ctcactgtat 240
ctgcaaatga acagcctgag agccgaggac acggctgtgt attactgcgc gagagattcc 300
cttatagtgg gagagagggg ctactggggc cagggaaccc tggtcaccgt ctcctca 357

<210> SEQ ID NO 212

<211> LENGTH: 357
<212> TYPE: DNA
<213> ORGANISM: Homo sapiens

<400> SEQUENCE: 212
gaggtgcagc tggtggagtc tgggggaggc ttggtccagc ctggggggtc cctgagactc 60
tcctgtgcag cctctggatt cacctttagt agctattgga tgtactgggt ccgccaggct 120
ccagggaagg ggctggagtg ggtggccaac ataaatcacg atggaagtga gaaatactat 180
gtggactctg tgaagggccg attcaccatc tccagagaca acgccaagaa ctcactgtat 240
ctgcaaatga acagcctgag agccgaggac acggctgtgt attactgcgc gagagataac 300
cttatagtgg gagagagggg ctactggggc cagggaaccc tggtcaccgt ctcctca 357

<210> SEQ ID NO 213
<211> LENGTH: 325
<212> TYPE: DNA
<213> ORGANISM: Homo sapiens

<400> SEQUENCE: 213
gaggtgcagc tggtggagtc tgggggaggc ttggtccagc ctggggggtc cctgagactc 60
tcctgtgcag cctctggatt cacctttagt agctattgga tgtactgggt ccgccaggct 120
ccagggaagg ggctggagtg ggtggccaac ataaatcacg gggaagtga gaaatactat 180 gtggactctg tgaagggccg attcaccatc tccagagaca acgccaagaa ctcactgtat 240
ctgcaaatga acagcctgag agccgaggac acggctgtgt attactgcgc gagagattcc 300
cttatagtgg gagagagggg ctact 325

<210> SEQ ID NO 214
<211> LENGTH: 389
<212> TYPE: DNA
<213> ORGANISM: Homo sapiens

<400> SEQUENCE: 214
ggggccaggg aaccctggtc accgtctcct cagaggtgca gctggtggag tctgggggag 60
gcttggtcca gcctgggggg tccctgagac tctcctgtgc agcctctgga ttcaccttta 120
gtagctattg gatgtactgg gtccgccagg ctccagggaa ggggctggag tgggtggcca 180
acataaatca ccagggaagt gagaaatact atgtggactc tgtgaagggc cgattcacca 240
tctccagaga caacgccaag aactcactgt atctgcaaat gaacagcctg agagccgagg 300
acacggctgt gtattactgc gcgagagatt cccttatagt gggagagagg ggctactggg 360
gccagggaac cctggtcacc gtctcctca 389

<210> SEQ ID NO 215
<211> LENGTH: 357
<212> TYPE: DNA
<213> ORGANISM: Homo sapiens

<400> SEQUENCE: 215
gaggtgcagc tggtggagtc tgggggaggc ttggtccagc ctggggggtc cctgagactc 60
tcctgtgcag cctctggatt cacctttagt agctattgga tgtactgggt ccgccaggct 120
ccagggaagg ggctggagtg ggtggccaac ataaatcacc ccggaagtga gaaatactat 180
gtggactctg tgaagggccg attcaccatc tccagagaca acgccaagaa ctcactgtat 240
ctgcaaatga acagcctgag agccgaggac acggctgtgt attactgcgc gagagattcc 300
cttatagtgg gagagagggg ctactggggc cagggaaccc tggtcaccgt ctcctca 357

<210> SEQ ID NO 216
<211> LENGTH: 357
<212> TYPE: DNA
<213> ORGANISM: Homo sapiens

<400> SEQUENCE: 216
gaggtgcagc tggtggagtc tgggggaggc ttggtccagc ctggggggtc cctgagactc 60
tcctgtgcag cctctggatt cacctttagt agctattgga tgtactgggt ccgccaggct 120
ccagggaagg ggctggagtg ggtggccaac ataaatcacg agggaagtga gaaatactat 180
gtggactctg tgaagggccg attcaccatc tccagagaca acgccaagaa ctcactgtat 240
ctgcaaatga acagcctgag agccgaggac acggctgtgt attactgcgc gagagattcc 300
cttatagtgg gagagagggg ctactggggc cagggaaccc tggtcaccgt ctcctca 357

<210> SEQ ID NO 217
<211> LENGTH: 357
<212> TYPE: DNA
<213> ORGANISM: Homo sapiens

<400> SEQUENCE: 217
gaggtgcagc tggtggagtc tgggggaggc ttggtccagc ctggggggtc cctgagactc 60
tcctgtgcag cctctggatt cacctttagt agctattgga tgtactgggt ccgccaggct 120
ccagggaagg ggctggagtg ggtggccaac ataaatcaca tcggaagtga gaaatactat 180
gtggactctg tgaagggccg attcaccatc tccagagaca acgccaagaa ctcactgtat 240
ctgcaaatga acagcctgag agccgaggac acggctgtgt attactgcgc gagagattcc 300
cttatagtgg gagagagggg ctactggggc cagggaaccc tggtcaccgt ctcctca 357

<210> SEQ ID NO 218
<211> LENGTH: 357
<212> TYPE: DNA
<213> ORGANISM: Homo sapiens

<400> SEQUENCE: 218
gaggtgcagc tggtggagtc tgggggaggc ttggtccagc ctggggggtc cctgagactc 60
tcctgtgcag cctctggatt cacctttagt agctattgga tgtactgggt ccgccaggct 120
ccagggaagg ggctggagtg ggtggccaac ataaatcacg atggaagtga gaaatactat 180
gtggactctg tgaagggccg attcaccatc tccagagaca acgccaagaa ctcactgtat 240
ctgcaaatga acagcctgag agccgaggac acggctgtgt attactgcgc gagagatacc 300
cttatagtgg gagagagggg ctactggggc cagggaaccc tggtcaccgt ctcctca 357

<210> SEQ ID NO 219
<211> LENGTH: 366
<212> TYPE: DNA
<213> ORGANISM: Homo sapiens

<400> SEQUENCE: 219
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcgag aggccccata 300
ccagccactg ctatacccga tgcttttgat atctggggcc aagggacaat ggtcactgtc 360
tcctca 366

<210> SEQ ID NO 220
<211> LENGTH: 357
<212> TYPE: DNA
<213> ORGANISM: Homo sapiens

<400> SEQUENCE: 220
gaggtgcagc tacagcagtg gggcgcagga ctgttgaagc cttcggagac cctgtccctc 60
acctgcgctg tctatggtgg gtccttcagt ggtcactact ggagctggat ccgccagccc 120
ccagggaagg ggctggagtg gattggggac ataaatcata gtggaagcac caactacaac 180
ccgtccctca agagtcgagt caccatatca gtagacacgt ccaagaatca gttctccctg 240
aagctgagct ctgtgaccgc cgcggacacg gctgtgtatt actgtgtgag agactacggt 300
gactcccgta gcctttttga ctactggggc cagggaaccc tggtcaccgt ctcttca 357

<210> SEQ ID NO 221
<211> LENGTH: 375
<212> TYPE: DNA
<213> ORGANISM: Homo sapiens

<400> SEQUENCE: 221
caggtgcagc tggtggagtc tgggggaggc ttggtacagc ctggggggtc cctgagactc 60
tcctgtgcag cctctggatt caccttcagt agctatggca tgcactgggt ccgccaggct 120
ccaggcaagg ggctggagtg ggtggcattt atgtcatatg atggcagtaa taaatactat 180
gtagactccg tgaagggccg attcaccatc tccagagaca attccaagaa tacgctgtat 240
ctgcaaatga acagcctgag agctgaggac acggctgtgt attactgtgc gaaaggcgat 300
tacgattttt ggagtggtta ccccgactac gatatggacg tctggggcca agggaccacg 360
gtcaccgtct cctca 375

<210> SEQ ID NO 222
<211> LENGTH: 378
<212> TYPE: DNA
<213> ORGANISM: Homo sapiens

<400> SEQUENCE: 222
gaggtgcagc tggtggagtc tgggggaggc ttggtcaagc ctggagggtc cctgagactc 60
tcctgtgcag cctctggatt caacttgatt agctatggca tgtactgggt ccgccaggct 120
ccaggcaagg ggctggagtg ggtggcagtt atatcatatg atggaagtaa taaaaactat 180
gcagactccg tgaagggccg attcaccatc tccagagaca attccaagaa tacgctgttt 240
ctgcaaatga acagcctgag agttgaggac acggctgtgt attactgtgc gaaagggggg 300
aatgccttgt atagcagtgg ctggcccgat gatggttttg atatcagggg ccaagggaca 360
atggtcactg tctcctca 378

<210> SEQ ID NO 223
<211> LENGTH: 351
<212> TYPE: DNA
<213> ORGANISM: Homo sapiens

<400> SEQUENCE: 223
caggtgcagc tggtggagtc tgggggaggc gtggtccagc ctgggaggtc cctgagactc 60
tcctgtgcag cctctggatt caccttcagt aactttggca tgcactgggc ccgccaggct 120

```
ccaggcaagg gactggagtg ggtggcagta atatcatatg atggaaatag taaatactat    180

gcagacaccg tgaagggccg attcaccatc tccagagaca attccaagaa cacgctgtat    240

ctggaaatga acagcctgag agctgatgac acggctgtgt attactgtgc gaaaggccta    300

tggcccccaa tggacgtcag gggccaaggg accacggtca ccgtctcctc a             351
```

<210> SEQ ID NO 224
<211> LENGTH: 372
<212> TYPE: DNA
<213> ORGANISM: Homo sapiens

<400> SEQUENCE: 224

```
gaggtgcagc tggtggagtc tgggggaggc tcggtccagc ctgggggtc cctgagactc     60

tcctgtgcag cctctggatt cacctttagt gactattgga tgacctgggt ccgccaggtt    120

ccagggaagg ggctggagtg ggtggccaac ataaagcaag atggaagtga gaaatactat    180

gtggactctg tgaagggccg attcaccatc tccagagaca acgccaagaa ctcactatat    240

ctgcaaatga atagcctgag agccgaggac acggctgtgt attactgtgc gagagatcga    300

ggaggagcag tggccccttta tcacaacggt atggacatgg ggggccaagg gaccacggtc    360

actgtctctt ca                                                        372
```

<210> SEQ ID NO 225
<211> LENGTH: 361
<212> TYPE: DNA
<213> ORGANISM: Homo sapiens

<400> SEQUENCE: 225

```
gaagtgcagc tggtggagtc tgggggaggt gaagaagcct ggggcctcag tgaaggtctc     60

ctgcaaggct tctggataca ccttcaccag ttatgatatc aactgggtgc gacaggccac    120

tggacaaggg cttgagtgga tgggatggat gaaccctaac agtggtaaca caggctatgc    180

acagaagttc cagggcagag tcaccatgac caggaacacc tccataagca cagcctacat    240

ggagctgagc agcctgagat ctgaggacac ggccgtgtat tactgtgcga gagggaacgg    300

gcccggtata actggaacta ctgactactg gggccaggga accctggtca ctgtctcttc    360

a                                                                    361
```

<210> SEQ ID NO 226
<211> LENGTH: 357
<212> TYPE: DNA
<213> ORGANISM: Homo sapiens

<400> SEQUENCE: 226

```
gaggtgcagc tggtggagtc tgggggaggt gtggtacggc ctgggggtc cctgagactc     60

tcctgtgcag cctctggatt cacctttgat gattatggca tgagctgggt ccgccaagct    120

ccagggaagg ggctggagtg ggtctctggt attaattgga atggtgatcg taccggttat    180

gcagactctg tgaagggccg attcaccatc tccagagaca acgccaagaa ctccctgtat    240

ctgcaaatga acagtctgag agccgaggac acggccttgt attactgtgg gagagagaat    300

gttatagtac cagctgctac ctactggggc cagggaaccc tggtcaccgt ctcctca      357
```

<210> SEQ ID NO 227
<211> LENGTH: 73
<212> TYPE: DNA
<213> ORGANISM: Artificial Sequence
<220> FEATURE:

-continued

<223> OTHER INFORMATION: Primer Sequence

<400> SEQUENCE: 227
gccgctggat tgttattact cgcggcccag ccggccatgg cccaggtbca gctggtgcag 60
tctggggctg agg 73

<210> SEQ ID NO 228
<211> LENGTH: 65
<212> TYPE: DNA
<213> ORGANISM: Artificial Sequence
<220> FEATURE:
<223> OTHER INFORMATION: Primer Sequence

<400> SEQUENCE: 228
gccgctggat tgttattact cgcggcccag ccggccatgg cccagatcac cttgaaggag 60
tctgg 65

<210> SEQ ID NO 229
<211> LENGTH: 71
<212> TYPE: DNA
<213> ORGANISM: Artificial Sequence
<220> FEATURE:
<223> OTHER INFORMATION: Primer Sequence

<400> SEQUENCE: 229
gccgctggat tgttattact cgcggcccag ccggccatgg ccsaggtgca gctggtggag 60
tctgggggag g 71

<210> SEQ ID NO 230
<211> LENGTH: 65
<212> TYPE: DNA
<213> ORGANISM: Artificial Sequence
<220> FEATURE:
<223> OTHER INFORMATION: Primer Sequence

<400> SEQUENCE: 230
gccgctggat tgttattact cgcggcccag ccggccatgg cccaggtgca gctgcaggag 60
tcggg 65

<210> SEQ ID NO 231
<211> LENGTH: 65
<212> TYPE: DNA
<213> ORGANISM: Artificial Sequence
<220> FEATURE:
<223> OTHER INFORMATION: Primer Sequence

<400> SEQUENCE: 231
gccgctggat tgttattact cgcggcccag ccggccatgg cccaggtaca gctgcagcag 60
tcagg 65

<210> SEQ ID NO 232
<211> LENGTH: 54
<212> TYPE: DNA
<213> ORGANISM: Artificial Sequence
<220> FEATURE:
<223> OTHER INFORMATION: Primer Sequence

<400> SEQUENCE: 232
ccgtggtgat ggtggtgatg gctaccgcca ccctcgagtg argagacrgt gacc 54

<210> SEQ ID NO 233
<211> LENGTH: 73

<212> TYPE: DNA
<213> ORGANISM: Artificial Sequence
<220> FEATURE:
<223> OTHER INFORMATION: Primer Sequence

<400> SEQUENCE: 233
gccgctggat tgttattact cgcggcccag ccggccatgg cccaggtgca gctggtgcag 60
tctggggctg agg 73

<210> SEQ ID NO 234
<211> LENGTH: 73
<212> TYPE: DNA
<213> ORGANISM: Artificial Sequence
<220> FEATURE:
<223> OTHER INFORMATION: Primer Sequence

<400> SEQUENCE: 234
gccgctggat tgttattact cgcggcccag ccggccatgg cccaggtcca gctcgtgcag 60
tctggggctg agg 73

<210> SEQ ID NO 235
<211> LENGTH: 73
<212> TYPE: DNA
<213> ORGANISM: Artificial Sequence
<220> FEATURE:
<223> OTHER INFORMATION: Primer Sequence

<400> SEQUENCE: 235
gccgctggat tgttattact cgcggcccag ccggccatgg cccaggttca gctggtgcag 60
tctggagctg agg 73

<210> SEQ ID NO 236
<211> LENGTH: 73
<212> TYPE: DNA
<213> ORGANISM: Artificial Sequence
<220> FEATURE:
<223> OTHER INFORMATION: Primer Sequence

<400> SEQUENCE: 236
gccgctggat tgttattact cgcggcccag ccggccatgg cccaggtcca gctggtacag 60
tctggggctg agg 73

<210> SEQ ID NO 237
<211> LENGTH: 65
<212> TYPE: DNA
<213> ORGANISM: Artificial Sequence
<220> FEATURE:
<223> OTHER INFORMATION: Primer Sequence

<400> SEQUENCE: 237
gccgctggat tgttattact cgcggcccag ccggccatgg cccagrtcac cttgaaggag 60
tctgg 65

<210> SEQ ID NO 238
<211> LENGTH: 71
<212> TYPE: DNA
<213> ORGANISM: Artificial Sequence
<220> FEATURE:
<223> OTHER INFORMATION: Primer Sequence

<400> SEQUENCE: 238
gccgctggat tgttattact cgcggcccag ccggccatgg ccgaggtgca gctggtggag 60
tctgggggag g 71

<210> SEQ ID NO 239
<211> LENGTH: 71
<212> TYPE: DNA
<213> ORGANISM: Artificial Sequence
<220> FEATURE:
<223> OTHER INFORMATION: Primer Sequence

<400> SEQUENCE: 239
gccgctggat tgttattact cgcggcccag ccggccatgg ccgaagtgca gctggtggag 60
tctgggggag g 71

<210> SEQ ID NO 240
<211> LENGTH: 71
<212> TYPE: DNA
<213> ORGANISM: Artificial Sequence
<220> FEATURE:
<223> OTHER INFORMATION: Primer Sequence

<400> SEQUENCE: 240
gccgctggat tgttattact cgcggcccag ccggccatgg cccaggtgca gctggtggag 60
tctgggggag g 71

<210> SEQ ID NO 241
<211> LENGTH: 71
<212> TYPE: DNA
<213> ORGANISM: Artificial Sequence
<220> FEATURE:
<223> OTHER INFORMATION: Primer Sequence

<400> SEQUENCE: 241
gccgctggat tgttattact cgcggcccag ccggccatgg ccgaggtgca gctgttggag 60
tctgggggag g 71

<210> SEQ ID NO 242
<211> LENGTH: 71
<212> TYPE: DNA
<213> ORGANISM: Artificial Sequence
<220> FEATURE:
<223> OTHER INFORMATION: Primer Sequence

<400> SEQUENCE: 242
gccgctggat tgttattact cgcggcccag ccggccatgg ccgaggtgca gctgttggag 60
tctgggggag g 71

<210> SEQ ID NO 243
<211> LENGTH: 65
<212> TYPE: DNA
<213> ORGANISM: Artificial Sequence
<220> FEATURE:
<223> OTHER INFORMATION: Primer Sequence

<400> SEQUENCE: 243
gccgctggat tgttattact cgcggcccag ccggccatgg cccaggtgca gctgcaggag 60
tcggg 65

<210> SEQ ID NO 244
<211> LENGTH: 66
<212> TYPE: DNA
<213> ORGANISM: Artificial Sequence
<220> FEATURE:
<223> OTHER INFORMATION: Primer Sequence

<400> SEQUENCE: 244
gccgctggat tgttattact cgcggcccag ccggccatgg cccaggtgca gctacagcag 60
tggggc 66

<210> SEQ ID NO 245
<211> LENGTH: 65
<212> TYPE: DNA
<213> ORGANISM: Artificial Sequence
<220> FEATURE:
<223> OTHER INFORMATION: Primer Sequence

<400> SEQUENCE: 245
gccgctggat tgttattact cgcggcccag ccggccatgg cccaggtaca gctgcagcag 60
tcagg 65

<210> SEQ ID NO 246
<211> LENGTH: 54
<212> TYPE: DNA
<213> ORGANISM: Artificial Sequence
<220> FEATURE:
<223> OTHER INFORMATION: Primer Sequence

<400> SEQUENCE: 246
ccgtggtgat ggtggtgatg gctaccgcca ccctcgagtg argagacrgt gacc 54

<210> SEQ ID NO 247
<211> LENGTH: 24
<212> TYPE: DNA
<213> ORGANISM: Artificial Sequence
<220> FEATURE:
<223> OTHER INFORMATION: Primer Sequence

<400> SEQUENCE: 247
ggccatggcc ggctgggccg cgag 24

<210> SEQ ID NO 248
<211> LENGTH: 99
<212> TYPE: DNA
<213> ORGANISM: Artificial Sequence
<220> FEATURE:
<223> OTHER INFORMATION: Primer Sequence

<400> SEQUENCE: 248
tcatcgaggg tggcgagcga acaaaaactc atctcagaag aatctgaatc atcacacatc 60
acacgggagc tagactgttg aaagttgttt agcaaaacc 99

<210> SEQ ID NO 249
<211> LENGTH: 121
<212> TYPE: PRT
<213> ORGANISM: Homo sapiens

<400> SEQUENCE: 249

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ala Thr Ile Ser Asp Ser Gly Ser Ser Ala Asp Tyr Ala Asp Ser Val
50 55 60

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Tyr Asn Trp Asn Pro Arg Ala Leu Gly Ile Trp Gly
            100                 105                 110

Gln Gly Thr Met Val Thr Val Ser Ser
        115                 120


<210> SEQ ID NO 250
<211> LENGTH: 749
<212> TYPE: PRT
<213> ORGANISM: Homo sapiens

<400> SEQUENCE: 250

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Asp Ala Gln Lys Leu
    290                 295                 300

Leu Glu Lys Met Gly Gly Ser Ala Pro Pro Asp Ser Ser Trp Arg Gly
305                 310                 315                 320
```

-continued

```
Ser Leu Lys Val Pro Tyr Asn Val Gly Pro Gly Phe Thr Gly Asn Phe
                325                 330                 335

Ser Thr Gln Lys Val Lys Met His Ile His Ser Thr Asn Glu Val Thr
            340                 345                 350

Arg Ile Tyr Asn Val Ile Gly Thr Leu Arg Gly Ala Val Glu Pro Asp
        355                 360                 365

Arg Tyr Val Ile Leu Gly Gly His Arg Asp Ser Trp Val Phe Gly Gly
    370                 375                 380

Ile Asp Pro Gln Ser Gly Ala Ala Val Val His Glu Ile Val Arg Ser
385                 390                 395                 400

Phe Gly Thr Leu Lys Lys Glu Gly Trp Arg Pro Arg Arg Thr Ile Leu
                405                 410                 415

Phe Ala Ser Trp Asp Ala Glu Glu Phe Gly Leu Leu Gly Ser Thr Glu
            420                 425                 430

Trp Ala Glu Glu Asn Ser Arg Leu Leu Gln Glu Arg Gly Val Ala Tyr
        435                 440                 445

Ile Asn Ala Asp Ser Ser Ile Glu Gly Asn Tyr Thr Leu Arg Val Asp
    450                 455                 460

Cys Thr Pro Leu Met Tyr Ser Leu Val His Asn Leu Thr Lys Glu Leu
465                 470                 475                 480

Lys Ser Pro Asp Glu Gly Phe Glu Gly Lys Ser Leu Tyr Glu Ser Trp
                485                 490                 495

Thr Lys Lys Ser Pro Ser Pro Glu Phe Ser Gly Met Pro Arg Ile Ser
            500                 505                 510

Lys Leu Gly Ser Gly Asn Asp Phe Glu Val Phe Phe Gln Arg Leu Gly
        515                 520                 525

Ile Ala Ser Gly Arg Ala Arg Tyr Thr Lys Asn Trp Glu Thr Asn Lys
    530                 535                 540

Phe Ser Gly Tyr Pro Leu Tyr His Ser Val Tyr Glu Thr Tyr Glu Leu
545                 550                 555                 560

Val Glu Lys Phe Tyr Asp Pro Met Phe Lys Tyr His Leu Thr Val Ala
                565                 570                 575

Gln Val Arg Gly Gly Met Val Phe Glu Leu Ala Asn Ser Ile Val Leu
            580                 585                 590

Pro Phe Asp Cys Arg Asp Tyr Ala Val Val Leu Arg Lys Tyr Ala Asp
        595                 600                 605

Lys Ile Tyr Ser Ile Ser Met Lys His Pro Gln Glu Met Lys Thr Tyr
    610                 615                 620

Ser Val Ser Phe Asp Ser Leu Phe Ser Ala Val Lys Asn Phe Thr Glu
625                 630                 635                 640

Ile Ala Ser Lys Phe Ser Glu Arg Leu Gln Asp Phe Asp Lys Ser Asn
                645                 650                 655

Pro Ile Val Leu Arg Met Met Asn Asp Gln Leu Met Phe Leu Glu Arg
            660                 665                 670

Ala Phe Ile Asp Pro Leu Gly Leu Pro Asp Arg Pro Phe Tyr Arg His
        675                 680                 685

Val Ile Tyr Ala Pro Ser Ser His Asn Lys Tyr Ala Gly Glu Ser Phe
    690                 695                 700

Pro Gly Ile Tyr Asp Ala Leu Phe Asp Ile Glu Ser Lys Val Asp Pro
705                 710                 715                 720

Ser Lys Ala Trp Gly Glu Val Lys Arg Gln Ile Tyr Val Ala Ala Phe
                725                 730                 735
```

Thr Val Gln Ala Ala Ala Glu Thr Leu Ser Glu Val Ala
740 745

<210> SEQ ID NO 251
<211> LENGTH: 6
<212> TYPE: PRT
<213> ORGANISM: Artificial Sequence
<220> FEATURE:
<223> OTHER INFORMATION: Hexa HIS

<400> SEQUENCE: 251

His His His His His His
1 5

<210> SEQ ID NO 252
<211> LENGTH: 25
<212> TYPE: PRT
<213> ORGANISM: Artificial Sequence
<220> FEATURE:
<223> OTHER INFORMATION: HIS Tag

<400> SEQUENCE: 252

Leu Glu Gly Gly Gly Ser Glu Gln Lys Leu Ile Ser Glu Glu Asp Leu
1 5 10 15

Asn His His His His His His Gly Ser
20 25

<210> SEQ ID NO 253
<211> LENGTH: 150
<212> TYPE: PRT
<213> ORGANISM: Artificial Sequence
<220> FEATURE:
<223> OTHER INFORMATION: VH domain HIS tagged

<400> SEQUENCE: 253

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Met His Trp Val Arg Gln Ala Pro Gly Lys Gly Leu Glu Trp Val
35 40 45

Ala Tyr Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Pro Ala Trp Gly Leu Arg Leu Gly Glu Ser Ser Ser Tyr
100 105 110

Asp Phe Asp Ile Trp Gly Gln Gly Thr Met Val Thr Val Ser Ser Leu
115 120 125

Glu Gly Gly Gly Ser Glu Gln Lys Leu Ile Ser Glu Glu Asp Leu Asn
130 135 140

His His His His His His
145 150

<210> SEQ ID NO 254
<211> LENGTH: 136
<212> TYPE: PRT
<213> ORGANISM: Artificial Sequence
<220> FEATURE:
<223> OTHER INFORMATION: VH domain HIS tagged

<400> SEQUENCE: 254

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Ser Ser Tyr
20 25 30

Ala Met Ser Trp Val Arg Gln Ala Pro Gly Lys Gly Leu Glu Trp Val
35 40 45

Ser Ser Ile Gly Glu Asn Asp Gly Thr Thr Asp Tyr Ala Asp Ser Val
50 55 60

Lys Gly Arg Phe Thr Ile Ser Arg Asp Asn Ser Lys Ser Met Leu Tyr
65 70 75 80

Leu Gln Met Asn Ser Leu Arg Val Glu Asp Thr Ala Val Tyr Tyr Cys
85 90 95

Val Lys Asp Gly Val His Trp Gly Gln Gly Thr Leu Val Thr Val Ser
100 105 110

Ser Leu Glu Gly Gly Gly Ser Glu Gln Lys Leu Ile Ser Glu Glu Asp
115 120 125

Leu Asn His His His His His His
130 135

<210> SEQ ID NO 255
<211> LENGTH: 129
<212> TYPE: PRT
<213> ORGANISM: Artificial Sequence
<220> FEATURE:
<223> OTHER INFORMATION: VH HEL-4-HIS tagged

<400> SEQUENCE: 255

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Arg Ile Ser Asp Glu
20 25 30

Asp Met Gly Trp Val Arg Gln Ala Pro Gly Lys Gly Leu Glu Trp Val
35 40 45

Ser Ser Ile Tyr Gly Pro Ser Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ser Ala Leu Glu Pro Leu Ser Glu Pro Leu Gly Phe Trp Gly Gln
100 105 110

Gly Thr Leu Val Thr Val Ser Ser Ala Ala Ala His His His His His
115 120 125

His

<210> SEQ ID NO 256
<211> LENGTH: 293
<212> TYPE: PRT
<213> ORGANISM: Artificial Sequence
<220> FEATURE:
<223> OTHER INFORMATION: 2 VH linked via peptide linker

<400> SEQUENCE: 256

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Met His Trp Val Arg Gln Ala Pro Gly Lys Gly Leu Glu Trp Val
35 40 45

Ala Tyr Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Pro Ala Trp Gly Leu Arg Leu Gly Glu Ser Ser Ser Tyr
100 105 110

Asp Phe Asp Ile Trp Gly Gln Gly Thr Met Val Thr Val Ser Ser Gly
115 120 125

Gly Gly Gly Ser Gly Gly Gly Gly Ser Gly Gly Gly Gly Ser Gly Gly
130 135 140

Gly Gly Ser Gly Gly Gly Gly Ser Gly Gly Gly Gly Ser Glu Val Gln
145 150 155 160

Leu Val Glu Ser Gly Gly Gly Val Val Gln Pro Gly Arg Ser Leu Arg
165 170 175

Leu Ser Cys Ala Ala Ser Gly Phe Ser Phe Ser Gly Tyr Gly Met His
180 185 190

Trp Val Arg Gln Ala Pro Gly Lys Gly Leu Glu Trp Val Ala Tyr Ile
195 200 205

Ser Tyr Asp Gly Ser Asn Lys Tyr Tyr Ala Asp Ser Val Lys Gly Arg
210 215 220

Phe Thr Ile Ser Arg Asp Asn Ser Lys Asn Thr Leu Tyr Leu Gln Met
225 230 235 240

Asn Ser Leu Arg Ala Glu Asp Thr Ala Val Tyr Tyr Cys Ala Lys Asp
245 250 255

Pro Ala Trp Gly Leu Arg Leu Gly Glu Ser Ser Ser Tyr Asp Phe Asp
260 265 270

Ile Trp Gly Gln Gly Thr Met Val Thr Val Ser Ser Ala Ala Ala His
275 280 285

His His His His His
290

<210> SEQ ID NO 257
<211> LENGTH: 279
<212> TYPE: PRT
<213> ORGANISM: Artificial Sequence
<220> FEATURE:
<223> OTHER INFORMATION: 2 VH linked via a peptide linker

<400> SEQUENCE: 257

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Gly Tyr
20 25 30

Gly Met His Trp Val Arg Gln Ala Pro Gly Lys Gly Leu Glu Trp Val
35 40 45

Ala Tyr Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

-continued

```
Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Leu Glu Ser Gly Gly Gly Leu Val Gln Pro Gly Gly Ser Leu Arg
                165                 170                 175

Leu Ser Cys Ala Ala Ser Gly Phe Ser Phe Ser Ser Tyr Ala Met Ser
            180                 185                 190

Trp Val Arg Gln Ala Pro Gly Lys Gly Leu Glu Trp Val Ser Ser Ile
        195                 200                 205

Gly Glu Asn Asp Gly Thr Thr Asp Tyr Ala Asp Ser Val Lys Gly Arg
    210                 215                 220

Phe Thr Ile Ser Arg Asp Asn Ser Lys Ser Met Leu Tyr Leu Gln Met
225                 230                 235                 240

Asn Ser Leu Arg Val Glu Asp Thr Ala Val Tyr Tyr Cys Val Lys Asp
                245                 250                 255

Gly Val His Trp Gly Gln Gly Thr Leu Val Thr Val Ser Ser Ala Ala
            260                 265                 270

Ala His His His His His His
        275
```

THERAPEUTIC MOLECULES BINDING PSMA

FIELD OF THE INVENTION

The invention relates to prostate specific membrane antigen (PSMA) binding molecules, and the use of such binding molecules in the treatment of disease.

INTRODUCTION

Prostate cancer is the most commonly diagnosed non-skin-related malignancy in males in developed countries. It is estimated that one in six males will be diagnosed with prostate cancer.

Current treatments for prostate cancer include surgery, radiation, and adjuvant hormonal therapy. Although these therapies are relatively effective in the early stages of disease, the majority of patients initially diagnosed with localized prostate cancer ultimately relapse.

Whilst chemotherapy is one of the most widely used approaches in combating advanced prostate cancer, its therapeutic efficacy is usually insufficient due to lack of specificity and associated toxicity. Lack of targeted delivery to prostate cancer cells is one of the primary obstacles in achieving feasible therapeutic effect. Consequently, there remains a critical need for strategies to increase the selectivity of anti-prostate cancer agents (Barve et al., *J Control Release.* 2014 August 10; 0: 118-132).

The diagnosis of prostate cancer has greatly improved following the use of serum-based markers such as the prostate specific antigen (PSA). In addition, prostate tumour-associated antigens offer targets for tumour imaging, diagnosis, and targeted therapies. The prostate specific membrane antigen (PSMA), a prostate tumour associated marker, is such a target.

PSMA is a 750-residue type II transmembrane glycoprotein highly restricted to prostate secretory epithelial cell membranes. It is highly expressed in prostate cancer cells and in nonprostatic solid tumor neovasculature and expressed at lower levels in other tissues, including healthy prostate, kidney, liver, small intestine, and brain. PSMA expression increases with prostate disease progression and metastasis and its expression level has thus been correlated with tumour aggressiveness. Various immunohistological studies have demonstrated increased PSMA levels in virtually all cases of prostatic carcinoma compared to those levels in benign prostate epithelial cells. Intense PSMA staining is found in all stages of the disease, including prostatic intraepithelial neoplasia, late stage androgen-independent prostate cancer and secondary prostate tumours localized to lymph nodes, bone, soft tissue, and lungs. PSMA is thus widely used as a biomarker for prostate cancer cells.

PSMA has a 3-part structure: a 19-amino-acid internal portion, a 24-amino-acid transmembrane portion, and a 707-amino-acid external portion. It forms a noncovalent homodimer that possesses glutamate carboxypeptidase activity based on its ability to process the neuropeptide N-acetylaspartylglutamate and glutamate-conjugated folate derivatives. PSMA is rapidly and efficiently internalized by an endocytic pathway and rapidly recycles back to the membrane.

Antibody-based therapeutics have emerged as important components of therapies for an increasing number of human malignancies in such fields as oncology, inflammatory and infectious diseases. In most cases, the basis of the therapeutic function is the high degree of specificity and affinity the antibody-based drug has for its target antigen. Arming monoclonal antibodies (mAbs) with drugs, toxins, or radionuclides is yet another strategy by which mAbs may induce a therapeutic effect. By combining the targeting specificity of an antibody with the tumour killing power of toxic effector molecules, immunoconjugates permit sensitive discrimination between target and normal tissue thereby resulting in fewer side effects than most conventional chemotherapeutic drugs.

Due to their size and other physical properties, however, mAbs have to be administered either intravenously (iv) or subcutaneously (sc) and therefore have a high systemic exposure. Thus, their route of delivery can often be suboptimal, resulting either in antibody binding to target antigen at non-disease locations (potentially compromising the healthy function of normal, non-disease tissue) or resulting in suboptimal PK/PD characteristics. Either outcome may result in a loss of efficacy and/or a compromised safety profile by virtue of the suboptimal route of administration.

The first PSMA-specific mAb reported, murine mAb 7E11, was subsequently developed and commercialized as a diagnostic agent for tumour imaging (ProstaScint, Cytogen, Princeton, N.J.). However, this antibody recognizes an intracellular epitope of PSMA exposed upon cell death which limits its usefulness as an imaging agent for the detection of PSMA. More recently, mAbs such as J591 that recognize the extracellular portion of PSMA have been identified.

The aim of the present invention is to address the need of alternative antibody-based treatments for use in the treatment of prostate cancer.

SUMMARY OF THE INVENTION

In one aspect, the invention relates to a binding molecule capable of binding human PSMA comprising a single human variable heavy chain domain ($V_H$) antibody selected from one of the following: a single $V_H$ domain antibody comprising a CDR1 sequence comprising SEQ ID NO. 1, a CDR2 sequence comprising SEQ ID NO. 2 and a CDR3 sequence comprising SEQ ID NO. 3; a single $V_H$ domain antibody comprising a CDR1 sequence comprising SEQ ID NO. 5, a CDR2 sequence comprising SEQ ID NO. 6 and a CDR3 sequence comprising SEQ ID NO. 7; a single $V_H$ domain antibody comprising a CDR1 sequence comprising SEQ ID NO. 9, a CDR2 sequence comprising SEQ ID NO. 10 and a CDR3 sequence comprising SEQ ID NO. 11; a single $V_H$ domain antibody comprising a CDR1 sequence comprising SEQ ID NO. 13, a CDR2 sequence comprising SEQ ID NO. 14 and a CDR3 sequence comprising SEQ ID NO. 15; a single $V_H$ domain antibody comprising a CDR1 sequence comprising SEQ ID NO. 17, a CDR2 sequence comprising SEQ ID NO. 18 and a CDR3 sequence comprising SEQ ID NO. 19; a single $V_H$ domain antibody comprising a CDR1 sequence comprising SEQ ID NO. 21, a CDR2 sequence comprising SEQ ID NO. 22 and a CDR3 sequence comprising SEQ ID NO. 23; a single $V_H$ domain antibody comprising a CDR1 sequence comprising SEQ ID NO. 25, a CDR2 sequence comprising SEQ ID NO. 26 and a CDR3 sequence comprising SEQ ID NO. 27; a single $V_H$ domain antibody comprising a CDR1 sequence comprising SEQ ID NO. 29, a CDR2 sequence comprising SEQ ID NO. 30 and a CDR3 sequence comprising SEQ ID NO. 31; a single domain $V_H$ domain antibody comprising a CDR1 sequence comprising SEQ ID NO. 33, a CDR2 sequence comprising SEQ ID NO. 34 and a CDR3 sequence comprising SEQ ID NO. 35 or a single $V_H$ domain antibody comprising a CDR1 sequence comprising SEQ ID NO. 37, a CDR2 sequence comprising SEQ ID NO. 38 and a CDR3 sequence comprising SEQ ID NO. 39.

In one embodiment, said CDR1 said CDR1 sequence comprises SEQ ID NO. 25, said CDR2 sequence comprises SEQ ID NO. 26 and said CDR3 sequence comprises or consists of $V_H$ domain antibody 1.27 (SEQ ID NO. 28). In one embodiment, said single domain $V_H$ domain antibody comprises or consists of a sequence selected from SEQ ID NOs 4, 8, 12, 16, 20, 24, 28, 32, 36 or 40. In one embodiment, said single domain $V_H$ domain antibody comprises or consists of SEQ ID NO 28.

In one embodiment, said binding molecule comprises a first single human heavy chain variable immunoglobulin ($V_H$) domain antibody capable of binding human PSMA as described above and a second single $V_H$ domain antibody capable of binding human PSMA.

In one aspect, the invention relates to a pharmaceutical composition comprising a binding molecule as described above.

In one aspect, the invention relates to an immunoconjugate comprising a binding molecule as described above.

In one aspect, the invention relates to a method for treating prostate cancer or a prostatic disorder comprising administering a therapeutically-effective amount of a binding molecule, an immunoconjugate or a pharmaceutical composition as described above.

In one aspect, the invention relates to a binding molecule, an immunoconjugate or a pharmaceutical composition as described above for use as medicament.

In one aspect, the invention relates to a binding molecule, an immunoconjugate or a pharmaceutical as described above for use in the treatment of prostate cancer or a prostatic disorder.

In one aspect, the invention relates to the use of a binding molecule, an immunoconjugate or a pharmaceutical composition according as described above in the manufacture of a medicament for the treatment of prostate cancer or a prostatic disorder.

In one aspect, the invention relates an in vivo or in vitro method for reducing human PSMA activity comprising contacting human PSMA with a binding molecule as described above In one aspect, the invention relates method for determining the presence of PSMA in a test sample by an immunoassay comprising contacting said sample with a binding molecule as described above and at least one detectable label.

In one aspect, the invention relates an isolated nucleic acid molecule comprising a nucleotide sequence encoding a binding molecule as described above.

In one aspect, the invention relates an immunoconjugate comprising a binding molecule as described above.

In one aspect, the invention relates an immunoconjugate of the formula A-(L-D)n wherein A is an antigen-binding moiety comprising a first human single $V_H$ domain antibody capable of binding specifically to human PSMA as defined above, optionally comprising a second human single $V_H$ domain antibody capable of binding specifically to human PSMA and optionally comprising a third human single $V_H$ domain antibody, L is a linker, and D is an auristatin or a derivative thereof and n is 1, 2, 3, 4, 5, 6, 7, 8, 9 or 10.

DRAWINGS

The invention is further illustrated in the following non-limited drawings.

FIG. 1. Binding of purified anti-PSMA $V_H$ in FMAT Mirrorball Assay. 1a ● 1.1, • 3.1, ▲ 2.10, ▼ 2.1, 1b ● 2.1, ▲ 2.13, ▼ 2.17 ◇ 2.15, ○ 2.12 Δ 2.22 1c single domain antibodies tested as shown by symbols from top to bottom ● 1.8, • 1.10, ▲ 1.11, ▼ 1.12, 1.13, ○ 01.14, 1.16, Δ 1.17, 1.18.

Figure 2:
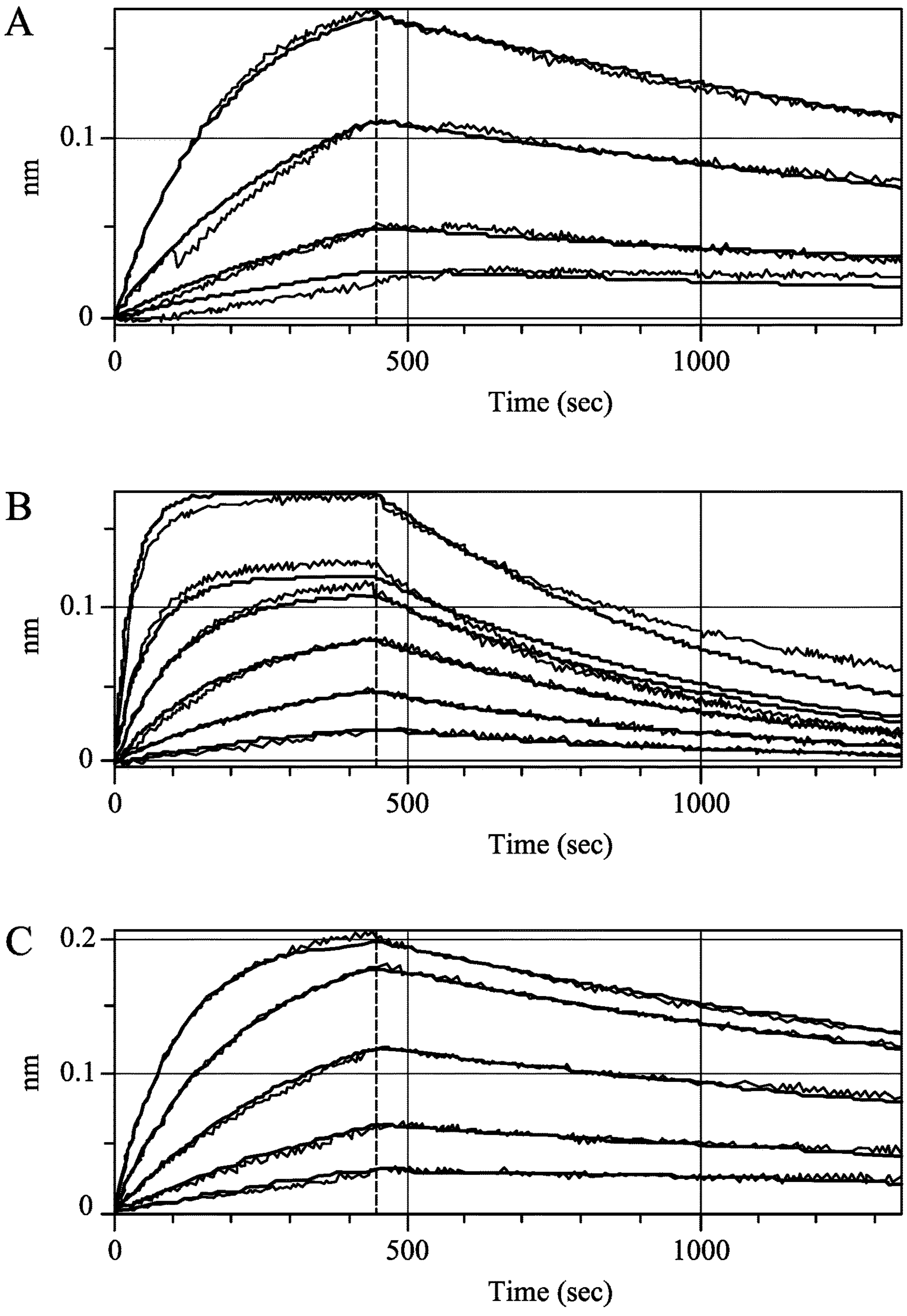

FIG. 2. Binding of purified anti-PSMA single domain antibodies to rhPSMA by Octet REDD 384, A. 2.1, B. 1.1, C. 3.1.

Figure 3:
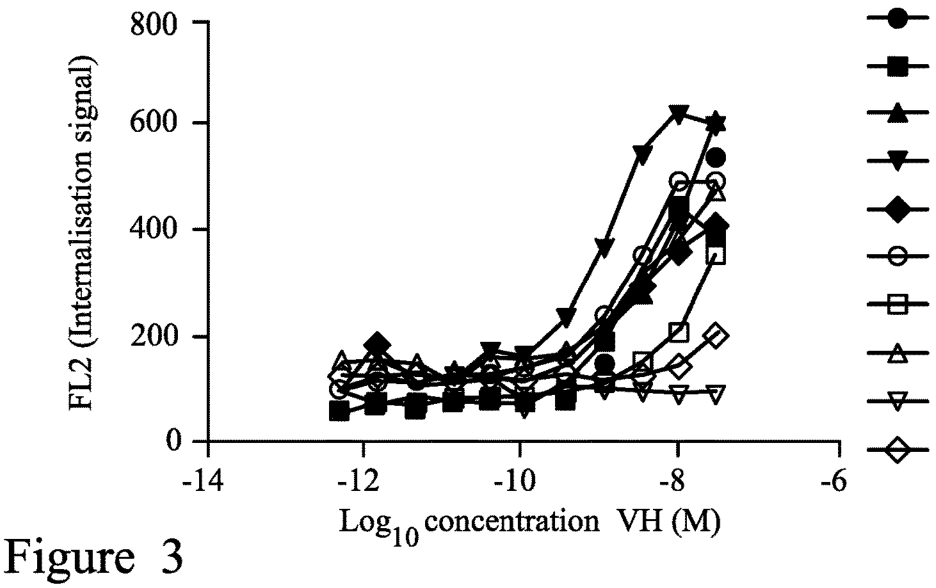

FIG. 3. pHrodo® Green internalisation of purified anti-PSMA single domain antibodies. single domain antibodies used (symbols in legend from top to bottom): 2.20, 12.1, 3.1, 3.2, 4.1, 5.1, 9.1, 14.1, 10.1, 7.1.

Figure 4:
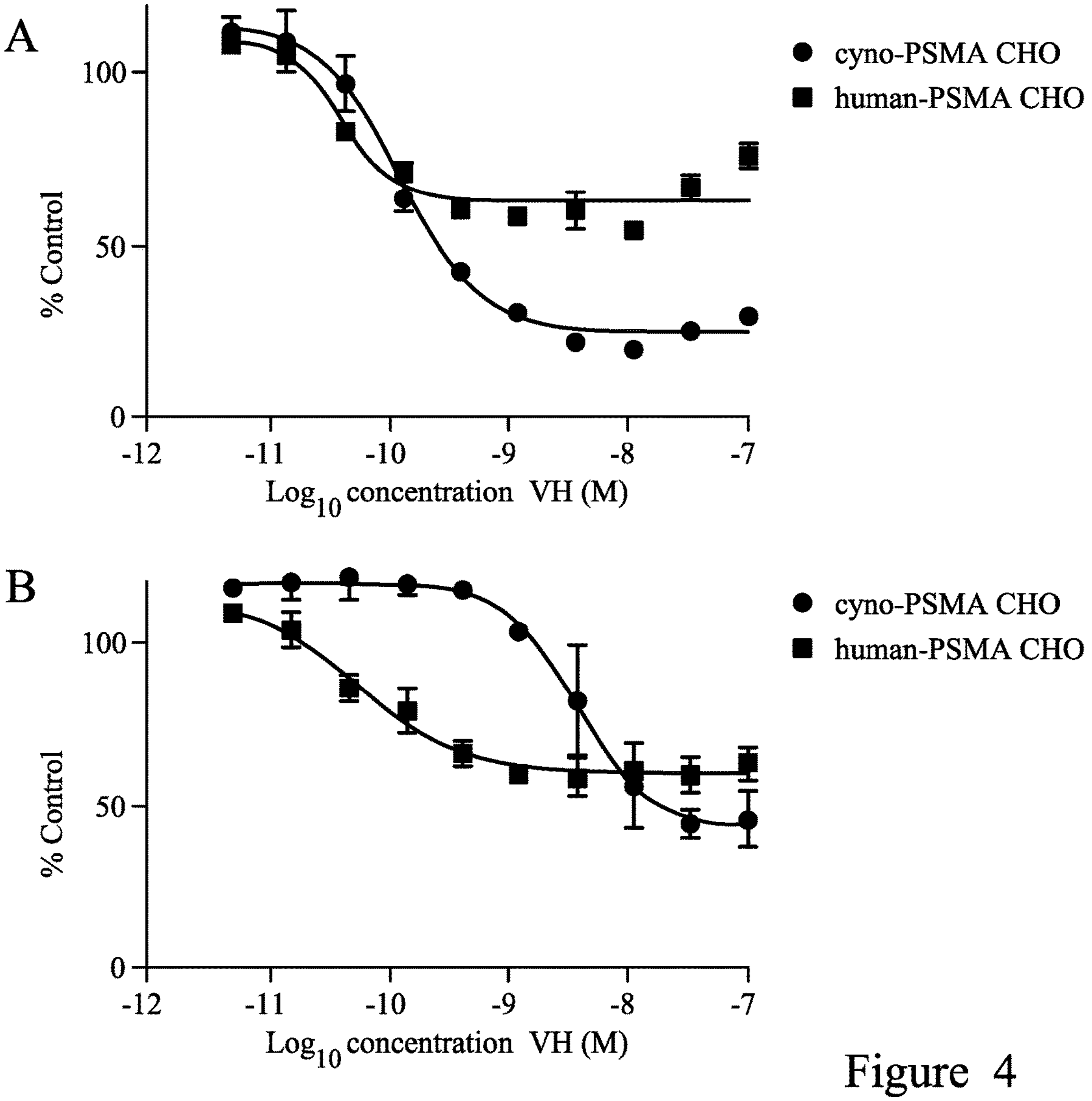

FIG. 4. Killing of cynoPSMA and human PSMA CHO with anti-PSMA single domain antibodies A. $V_H$ 2.1 B. $V_H$ 1.1.

Figure 5:
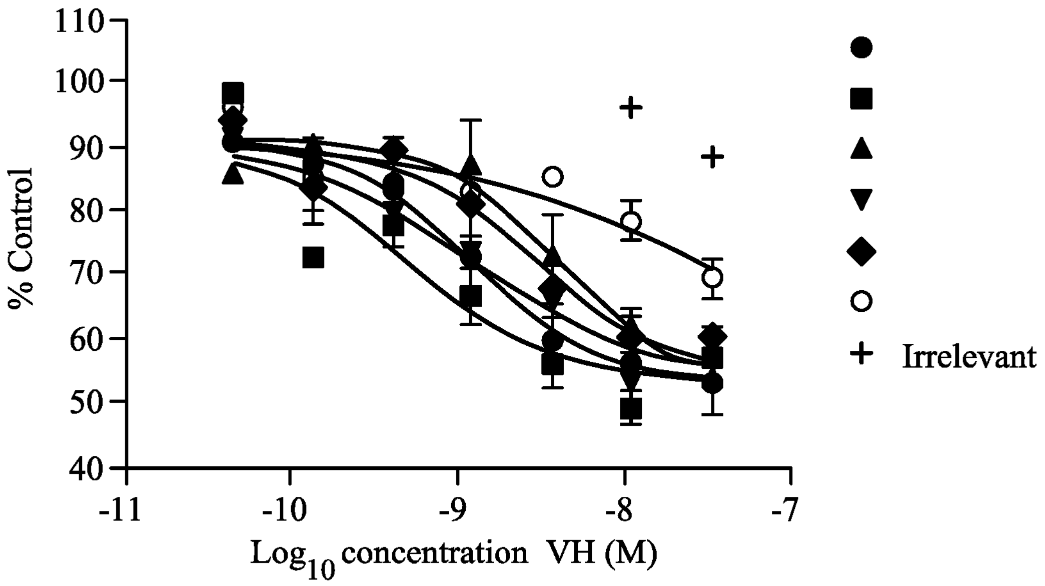

FIG. 5. Killing of LNCap with anti-PSMA single domain antibodies. sDAbs used (symbols in legend from top to bottom): $V_H$ 1.1, 2.1, 7.1, 3.1, 12.1, 4.1.

Figure 6:
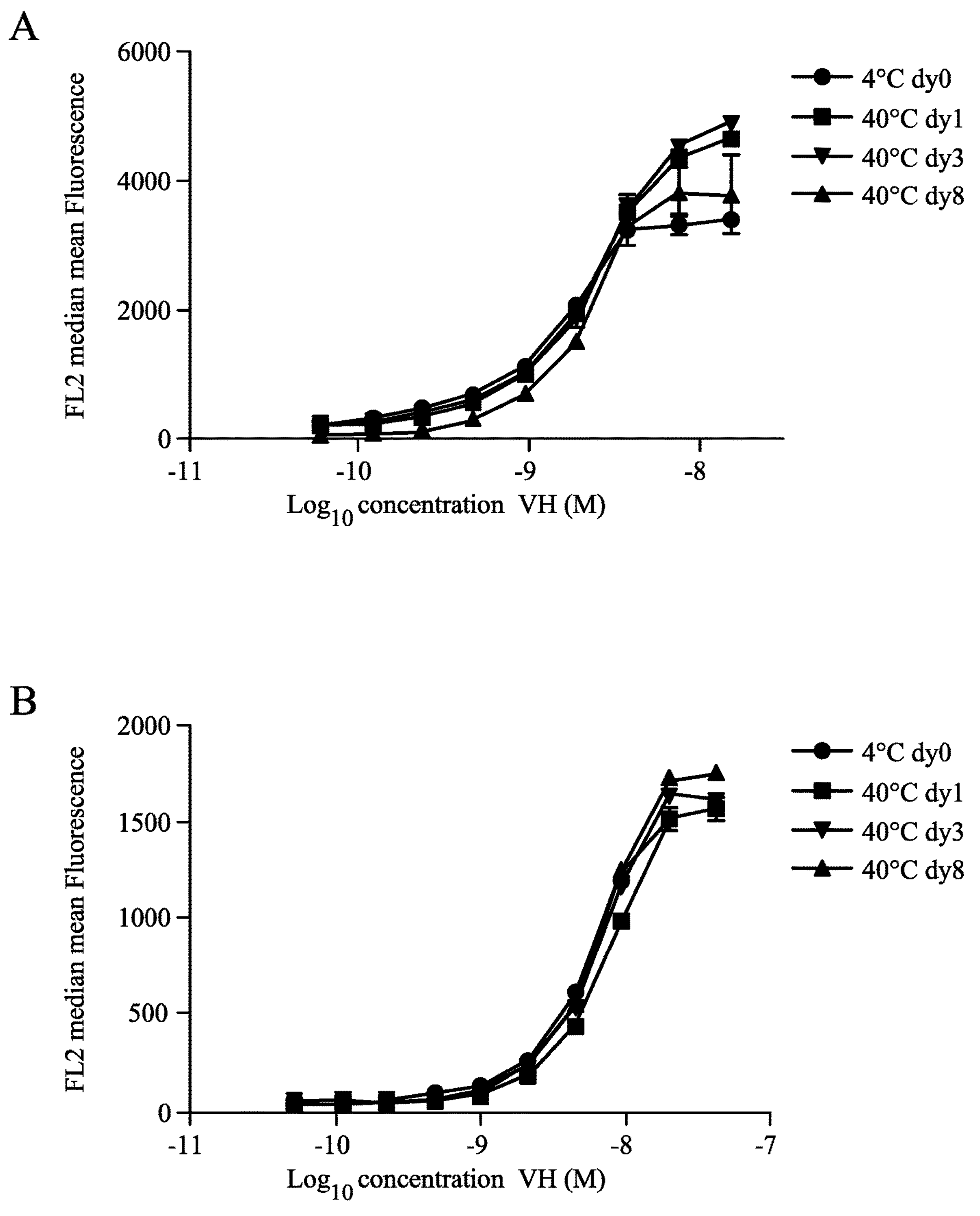

FIG. 6. Binding of anti-PSMA single domain antibodies to cynoPSMA CHO following heating to 40° C. A. $V_H$ 2.1 B. $V_H$ 1.1.

Figure 7:
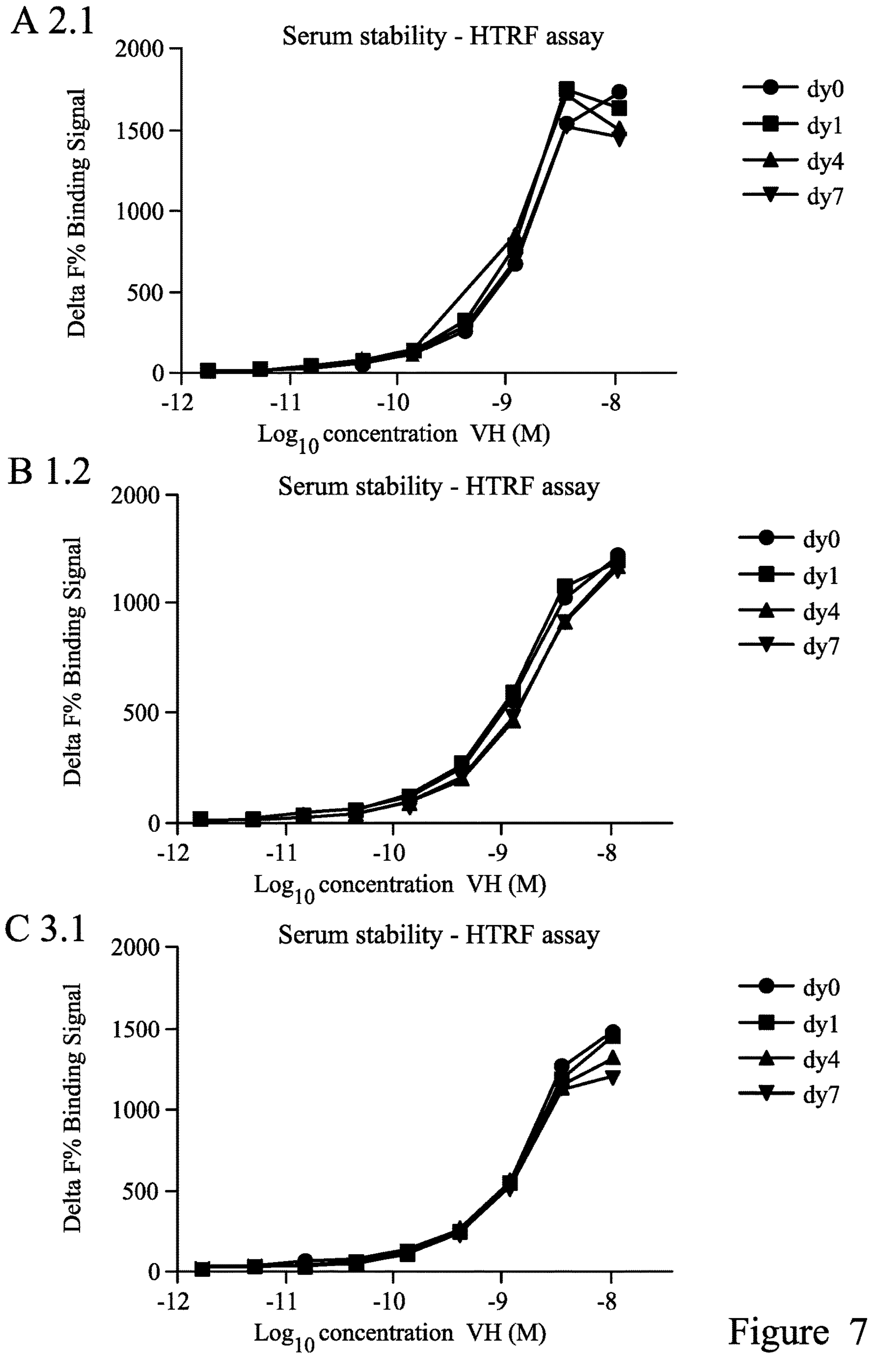

FIG. 7. Serum stability of anti-PSMA parent single domain antibodies at 37° C. A. $V_H$ 2.1 B. $V_H$ 1.1. C. $V_H$ 3.1.

Figure 8:
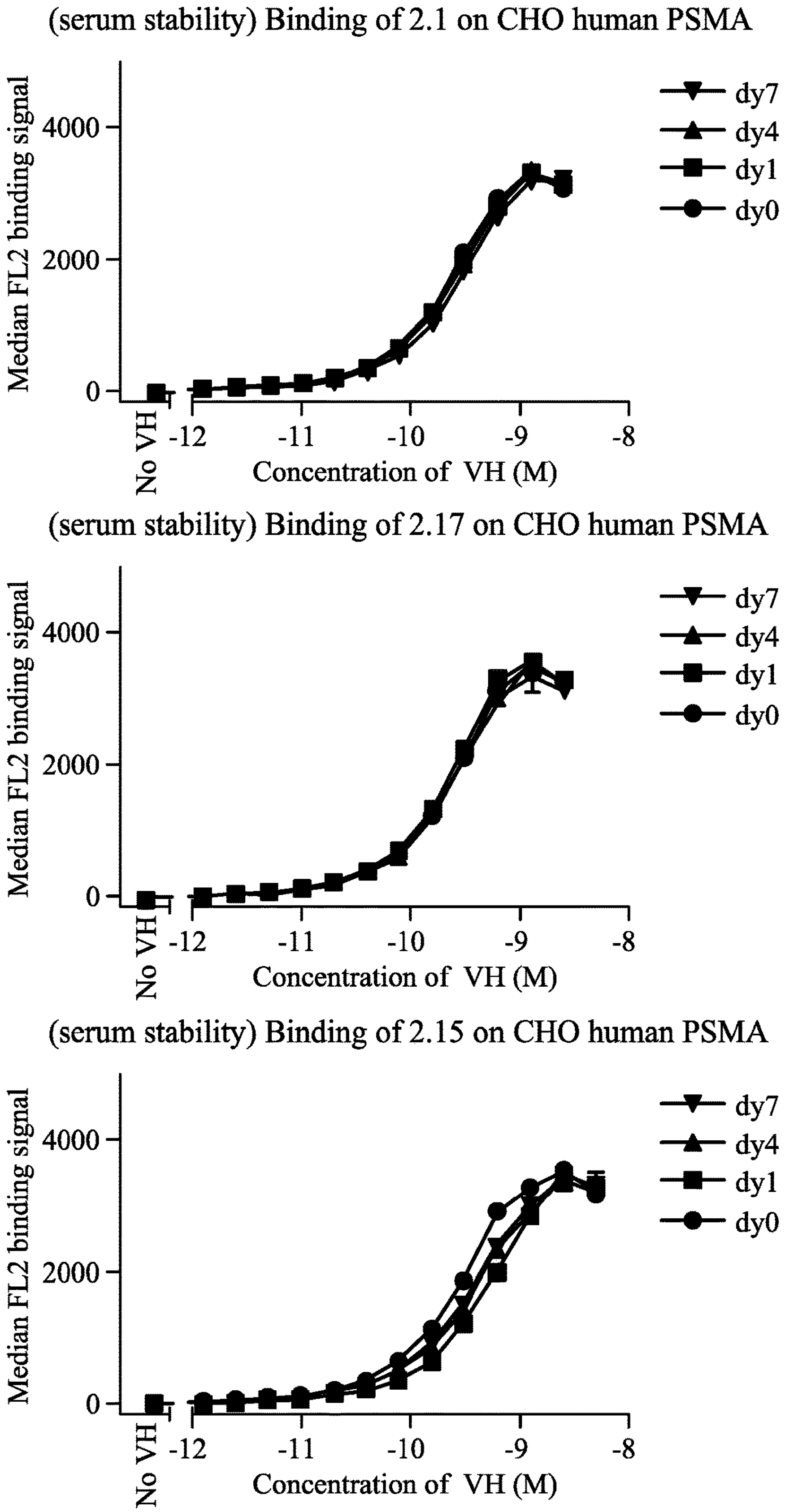
Figure 8:
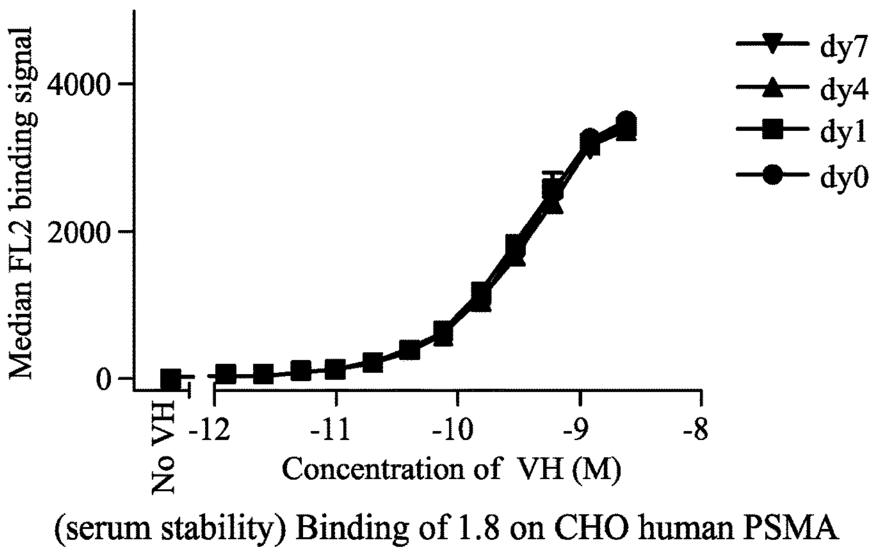
Figure 8:
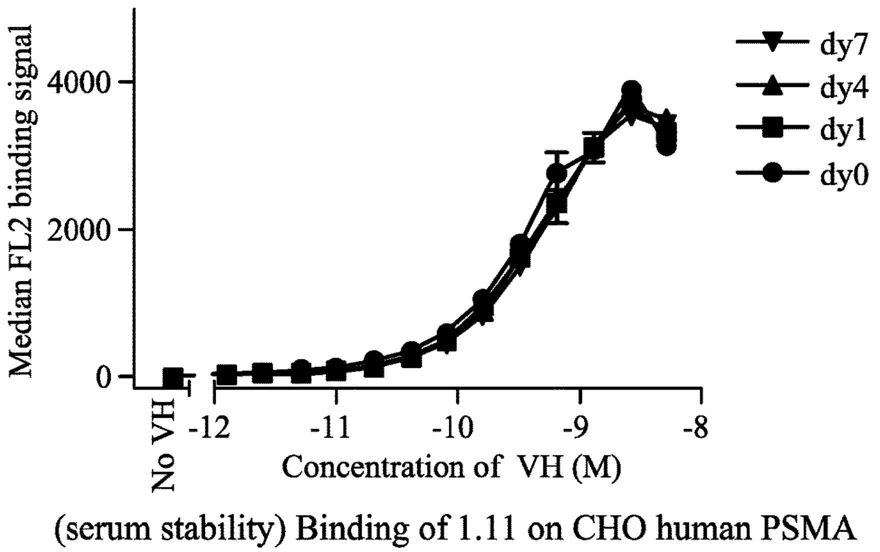
Figure 8:
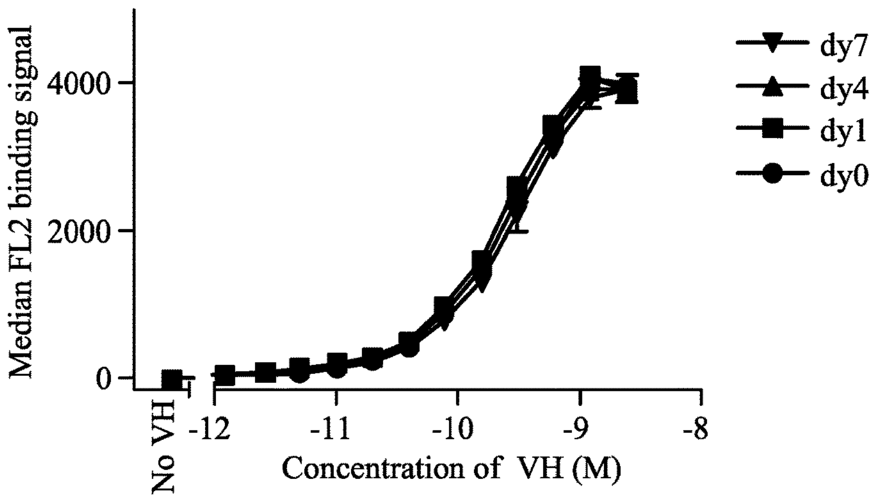
Figure 8:
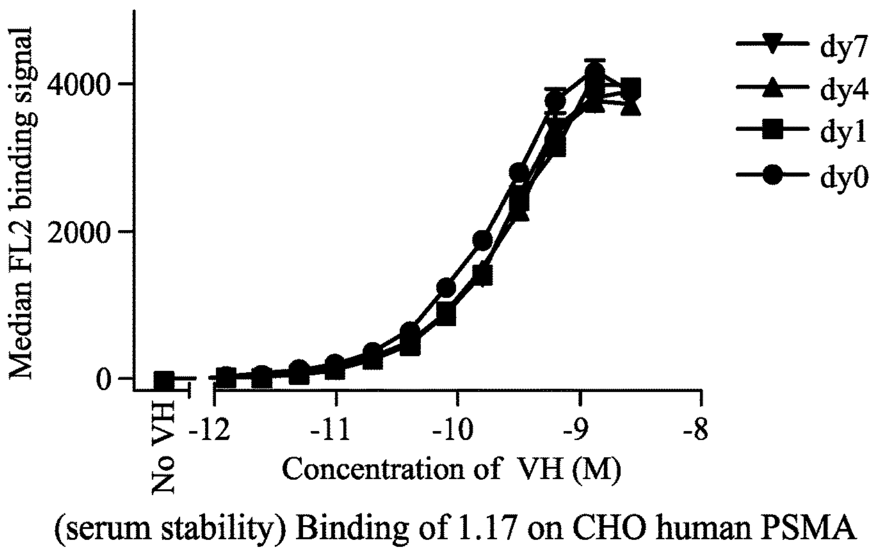
Figure 8:
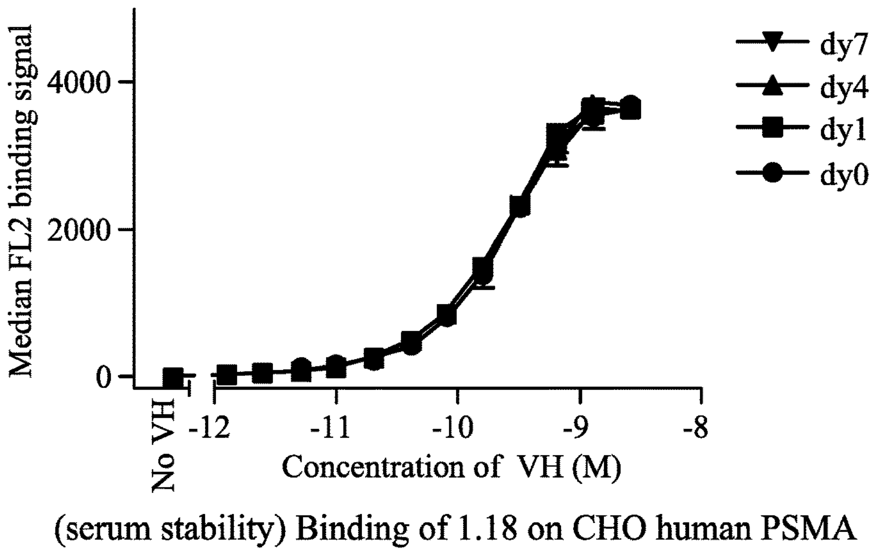
Figure 8:
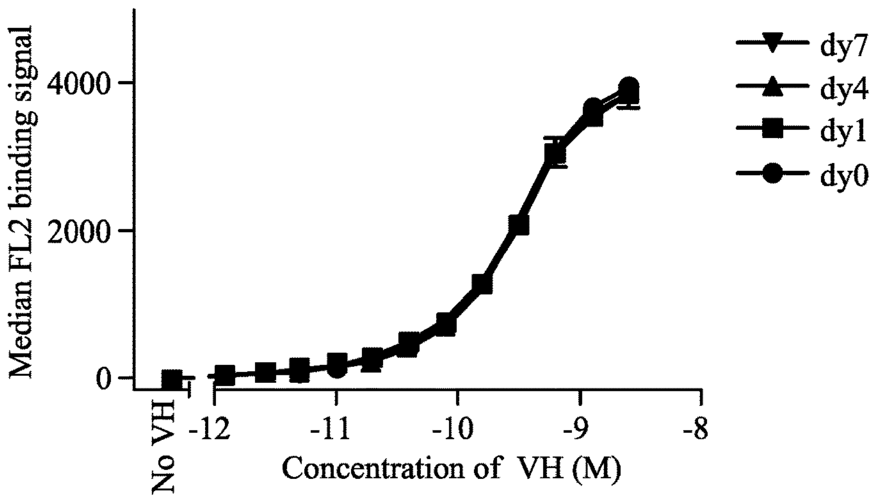

FIG. 8. Serum stability of various anti-PSMA variants single domain antibodies at 37° C.

Figure 9:
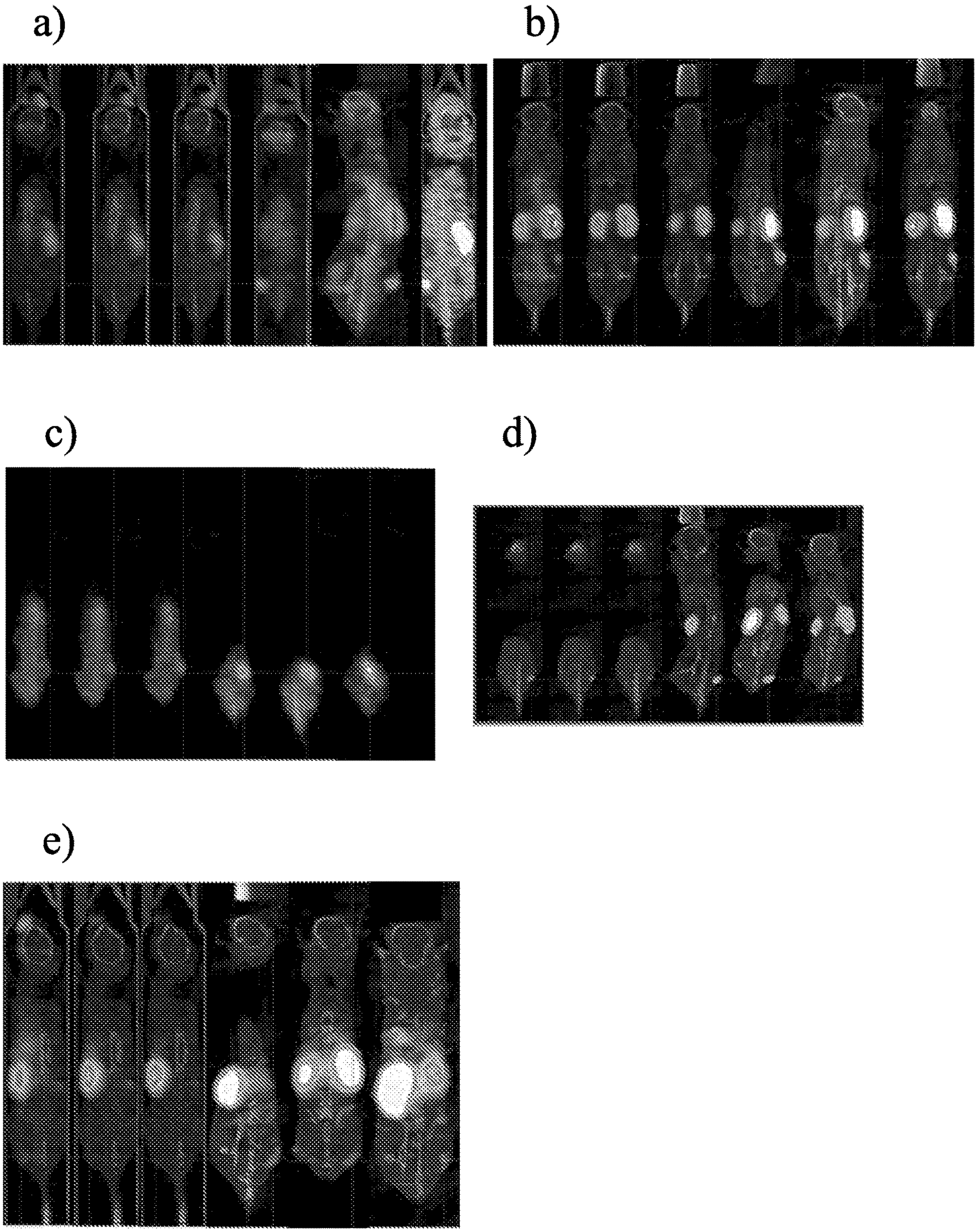

FIG. 9. in vivo imaging. Imaging 5 min to 24 h a) benchmark mAb, b) $V_H$ 2.1, c) $V_H$ 2.1-MSA, d) $V_H$ 1.1, e) negative control.

Figure 10:
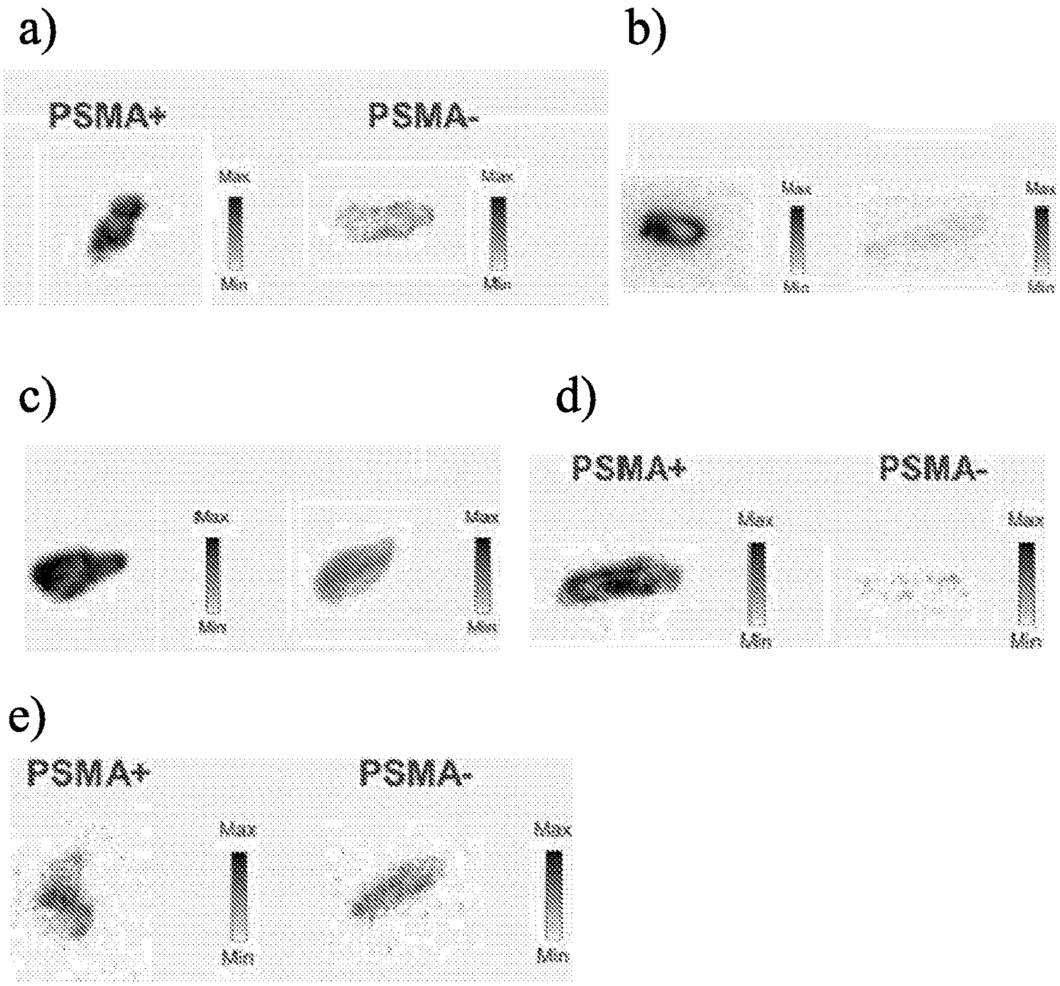

FIG. 10. in vivo imaging 24 h radiograph a) benchmark mAb, b) $V_H$ 2.1, c) $V_H$ 2.1-MSA, d) $V_H$ 1.1, e) negative control.

Figure 11:
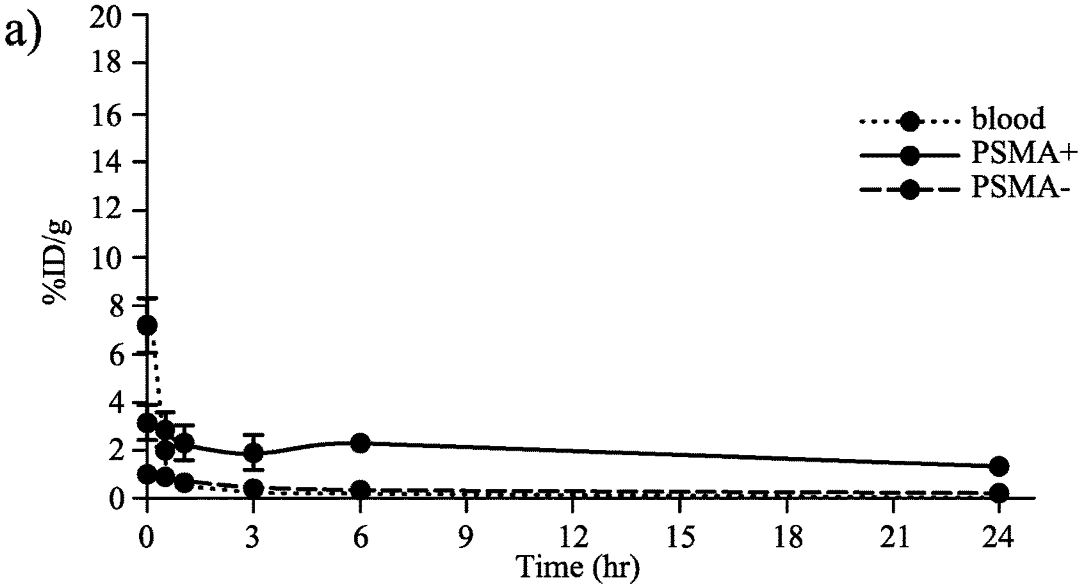
Figure 11:
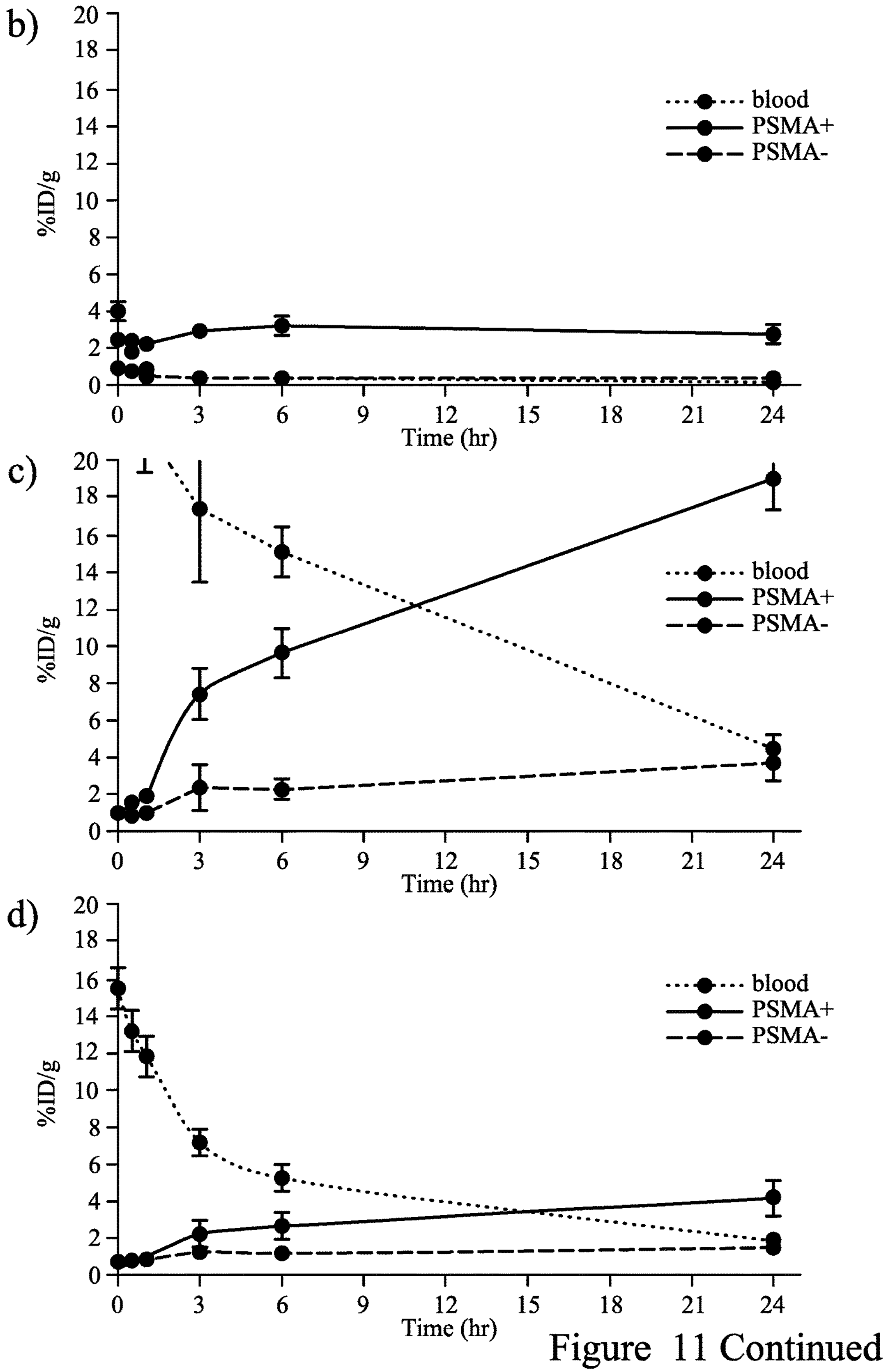
Figure 11:
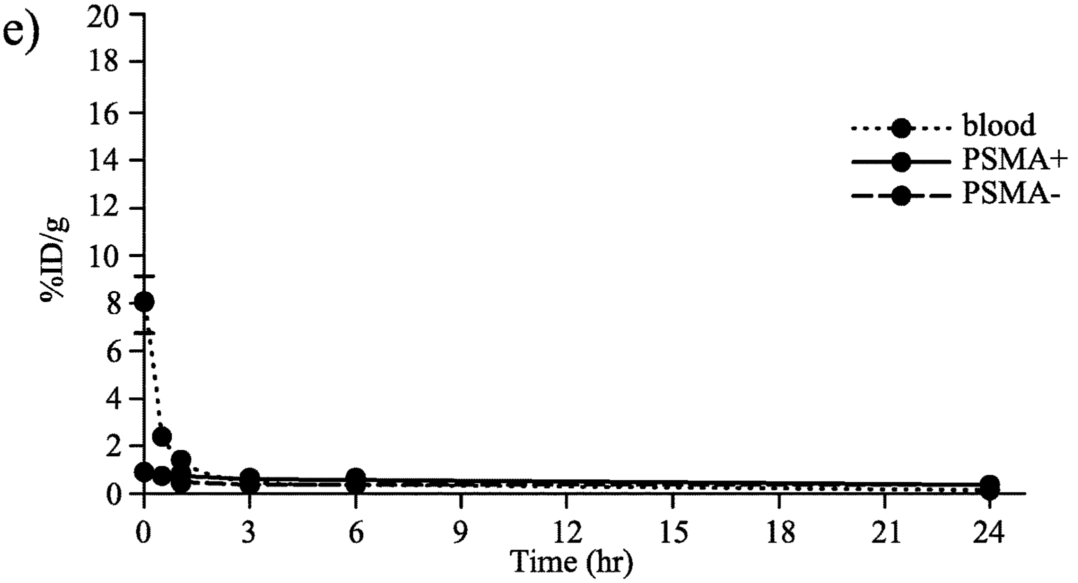

FIG. 11. Comparison of PSMA+ tumor, PSMA− tumor and blood biodistribution at 5 min to 24 h. a) $V_H$ 1.1 b) $V_H$ 2.1 c) $V_H$ 2.1 half life extended d) benchmark mAb e) HEL4 control.

Figure 12:
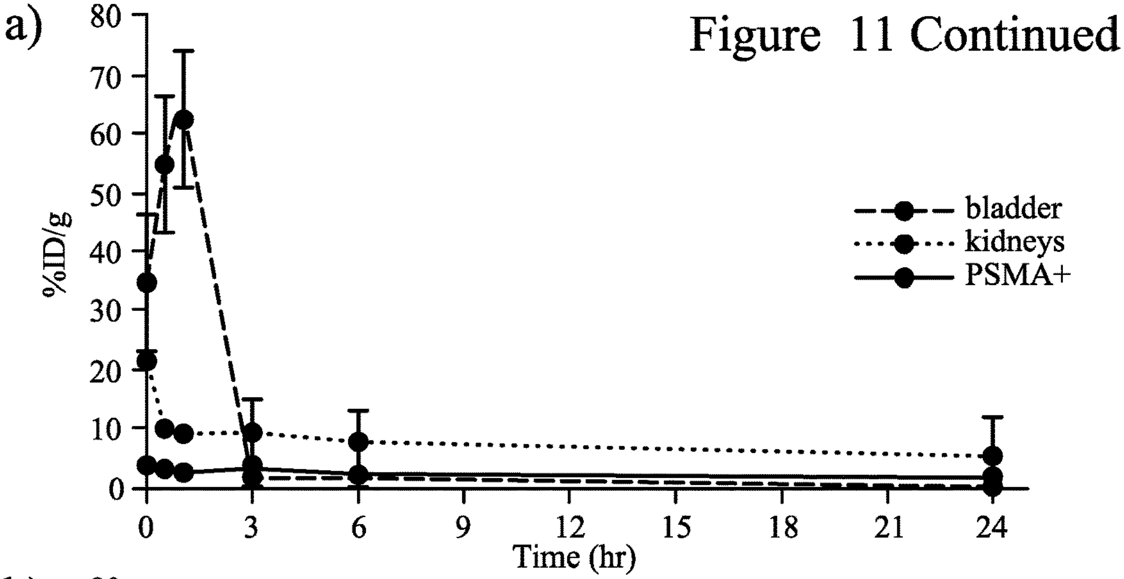
Figure 12:
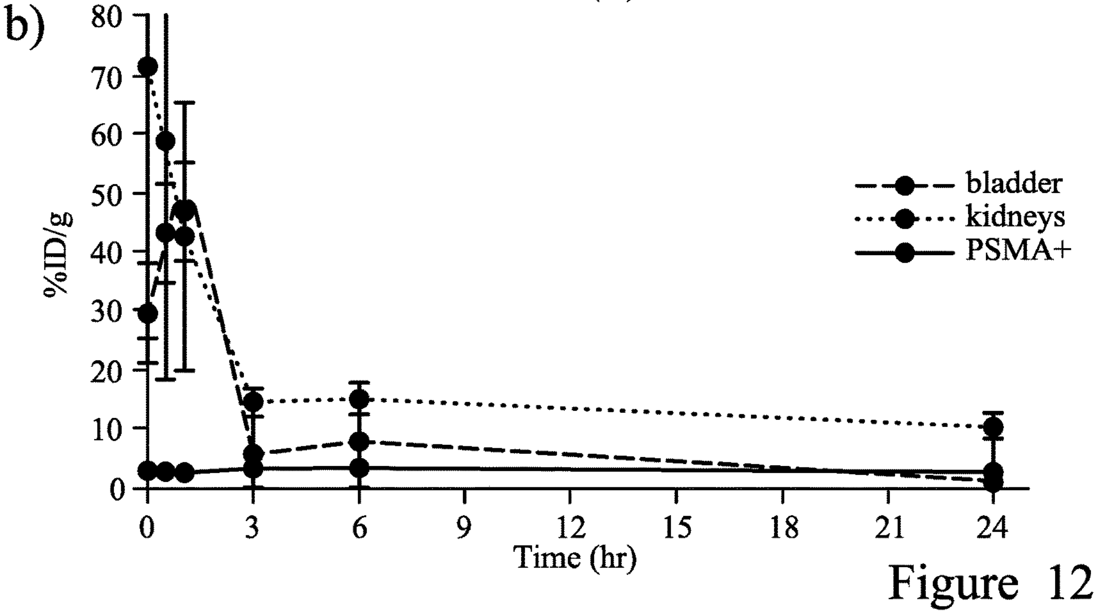
Figure 12:
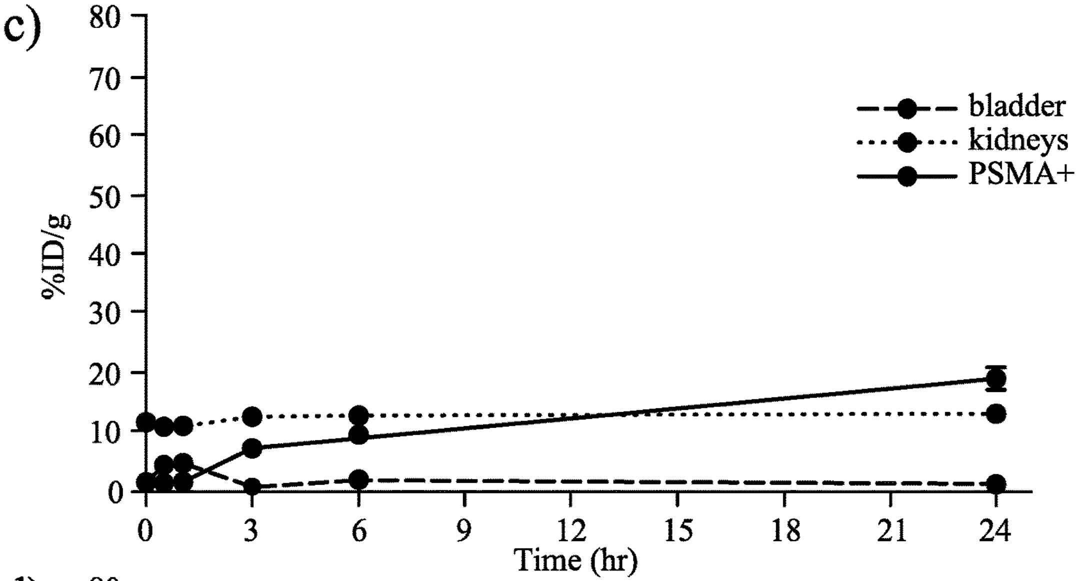
Figure 12:
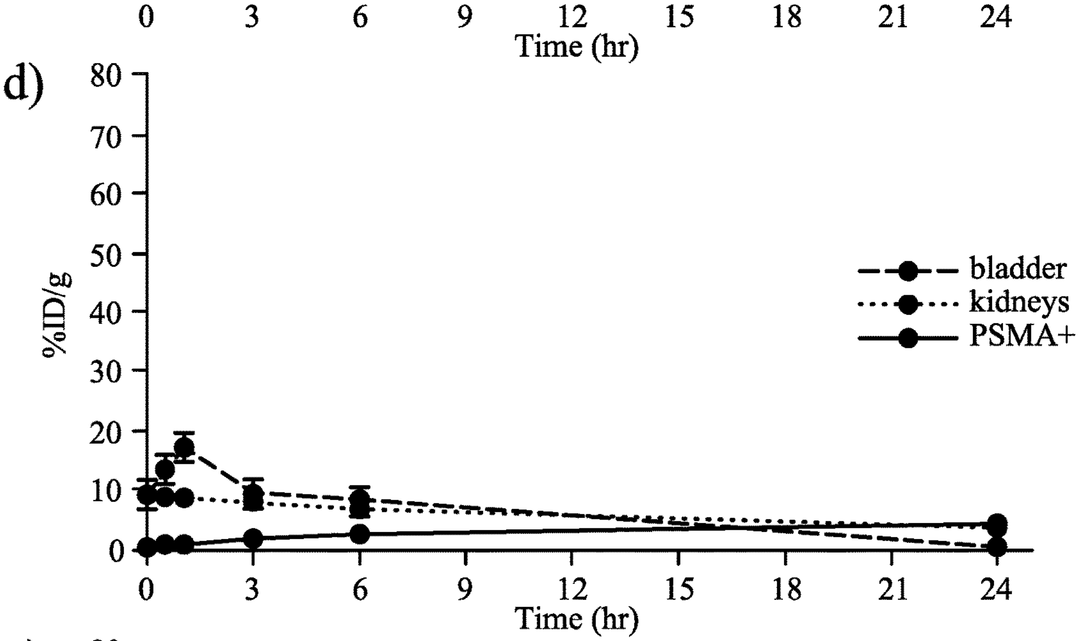
Figure 12:
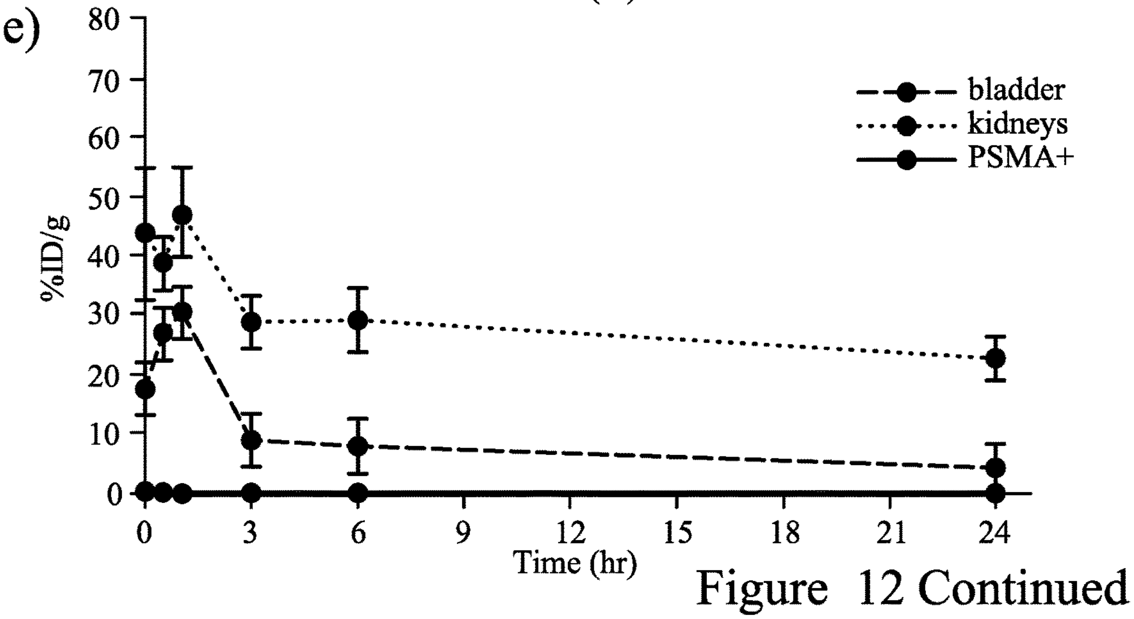

FIG. 12. Comparison of PSMA+ tumor, bladder and kidney biodistribution at 5 min to 24 h. a) $V_H$ 1.1 b) $V_H$ 2.1 c) $V_H$ 2.1 half life extended d) benchmark mAb e) HEL4 control.

Figure 13:
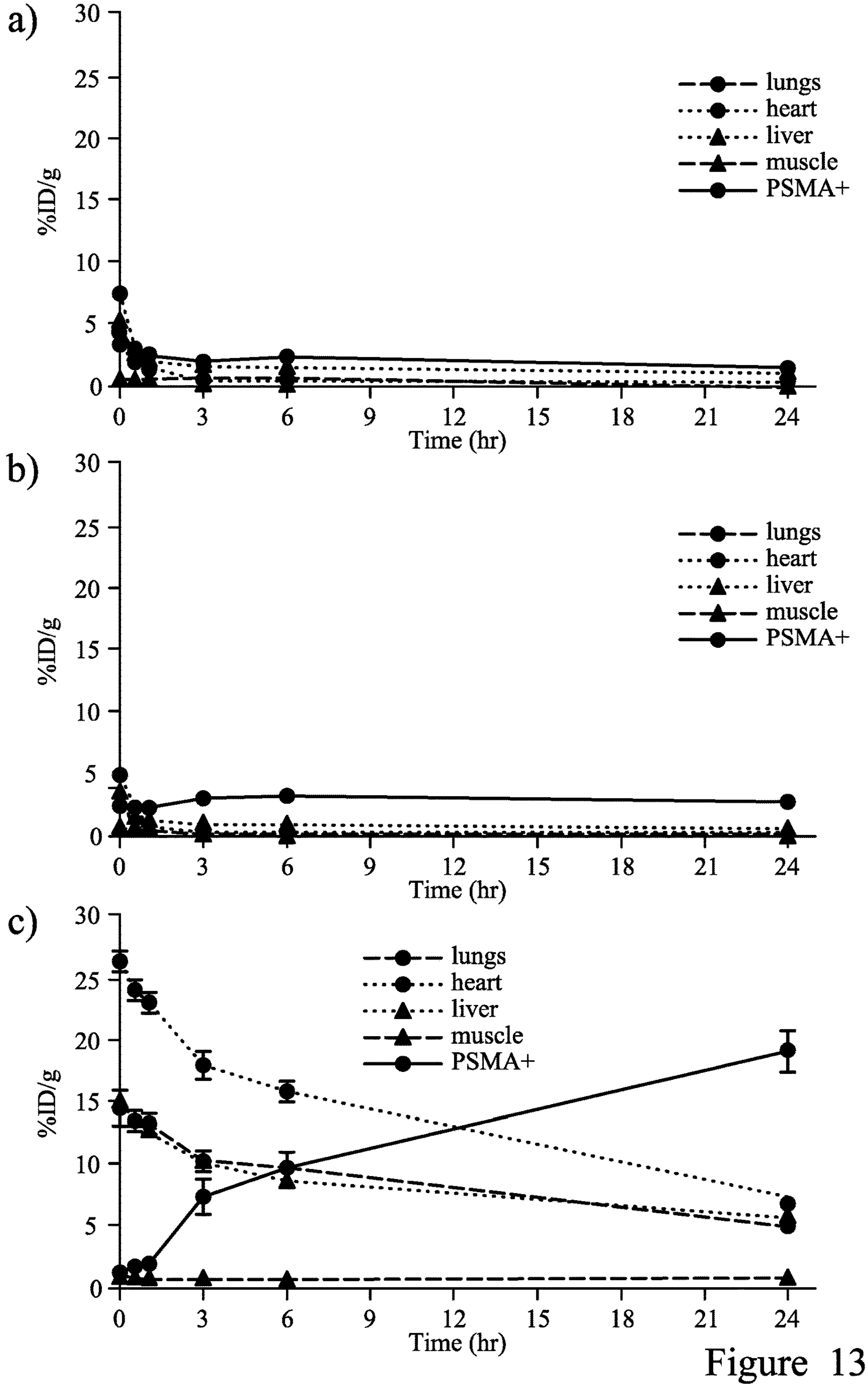
Figure 13:
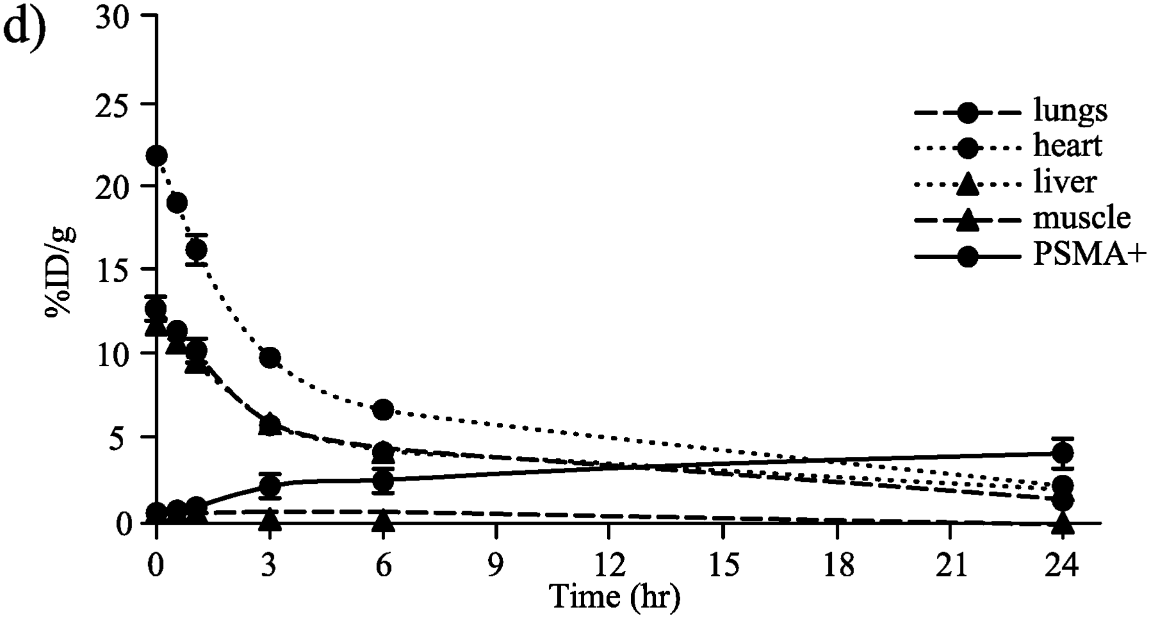
Figure 13:
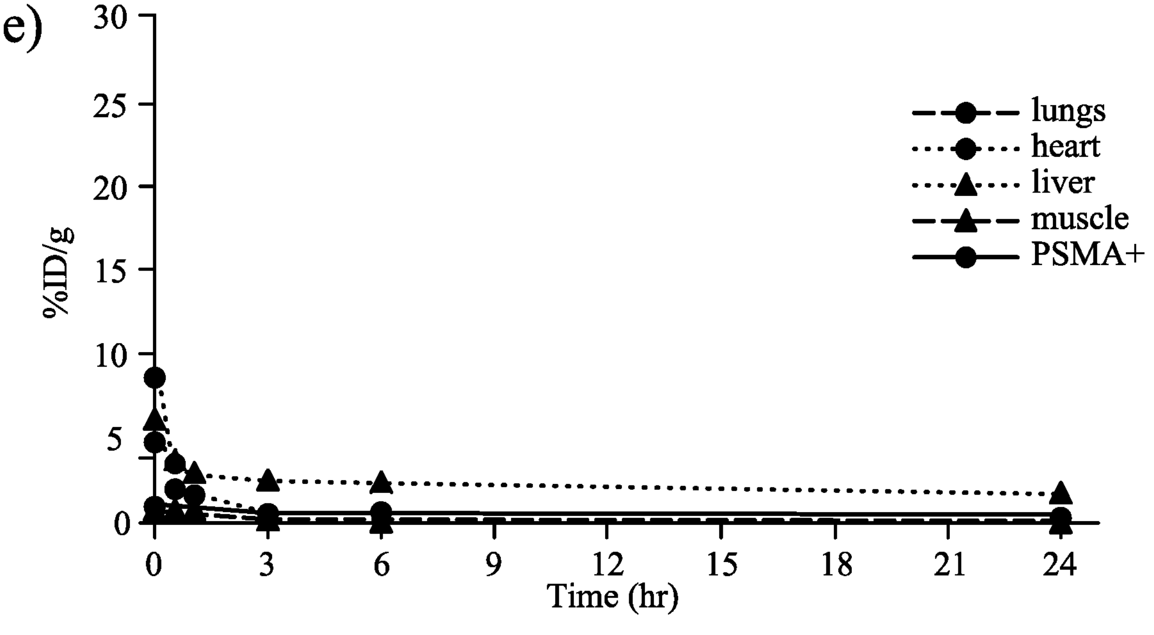

FIG. 13. Comparison of lungs, heart, liver, muscle and PSMA expressing (PSMA+) tumor biodistribution biodistribution at 5 min to 24 h. a) $V_H$ 1.1 b) $V_H$ 2.1 c) $V_H$ 2.1 half life extended d) benchmark mAb e) HEL4 control.

Figure 14:
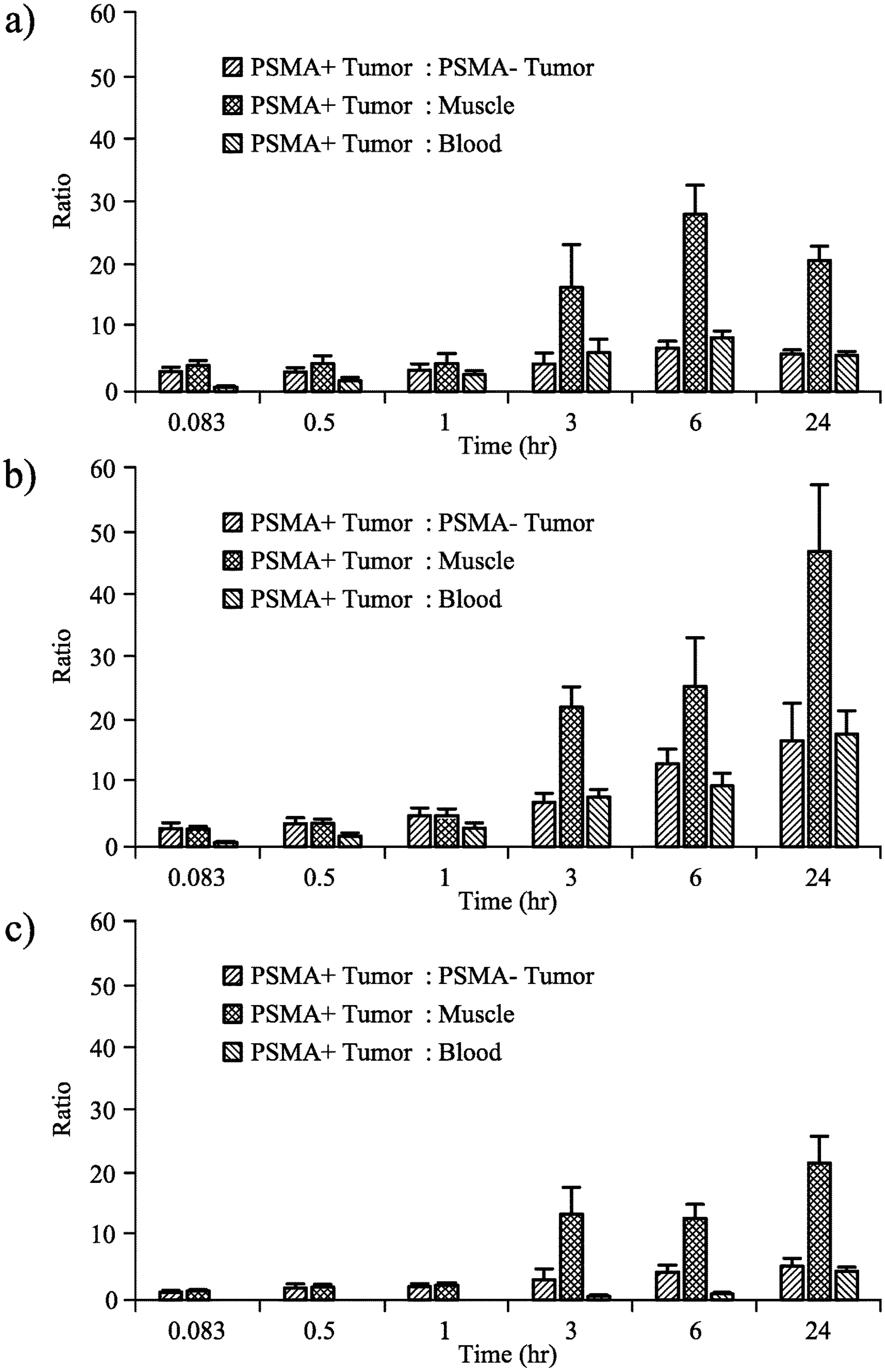
Figure 14:
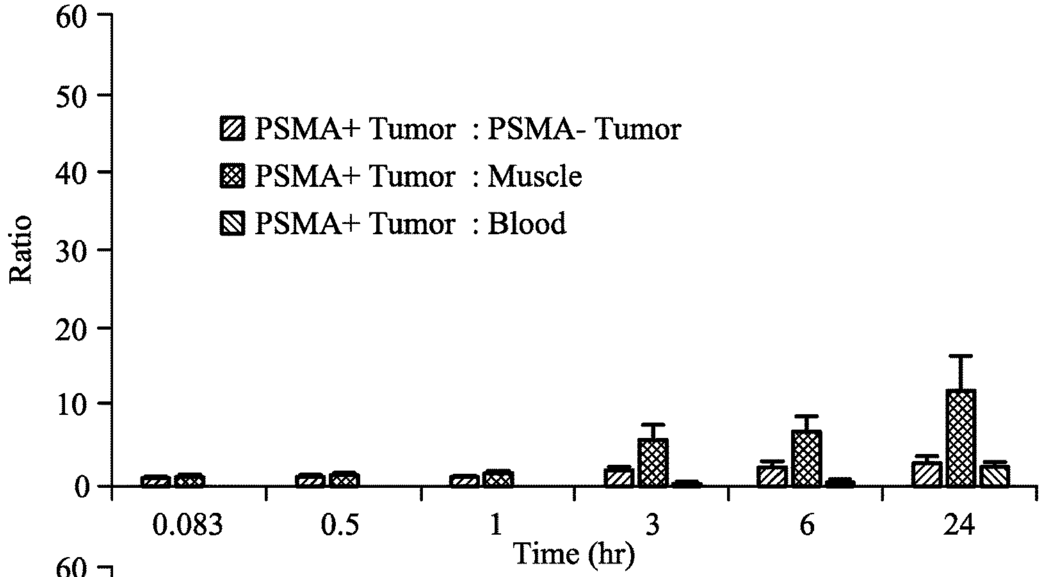
Figure 14:
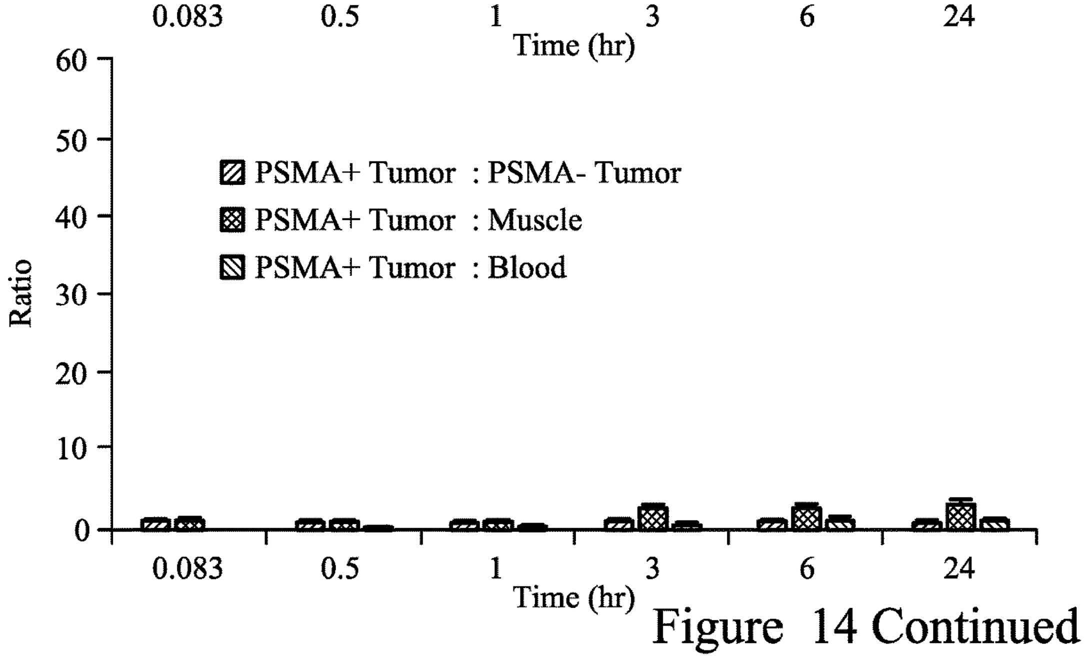

FIG. 14. Comparison of PSMA+ tumor to PSMA− tumor, blood or muscle ratios at 5 min to 24 h. a) $V_H$ 1.1 b) $V_H$ 2.1 c) $V_H$ 2.1 half life extended d) benchmark mAb e) HEL4 control.

Figure 15:
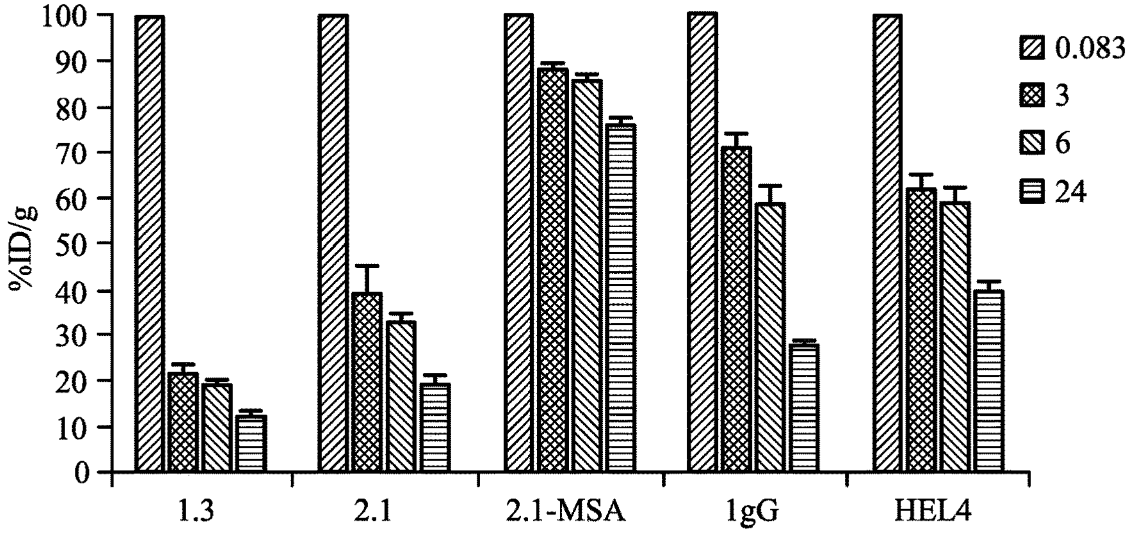

FIG. 15. Comparison of whole body activity from 5 min to 24 h.

Figure 16:
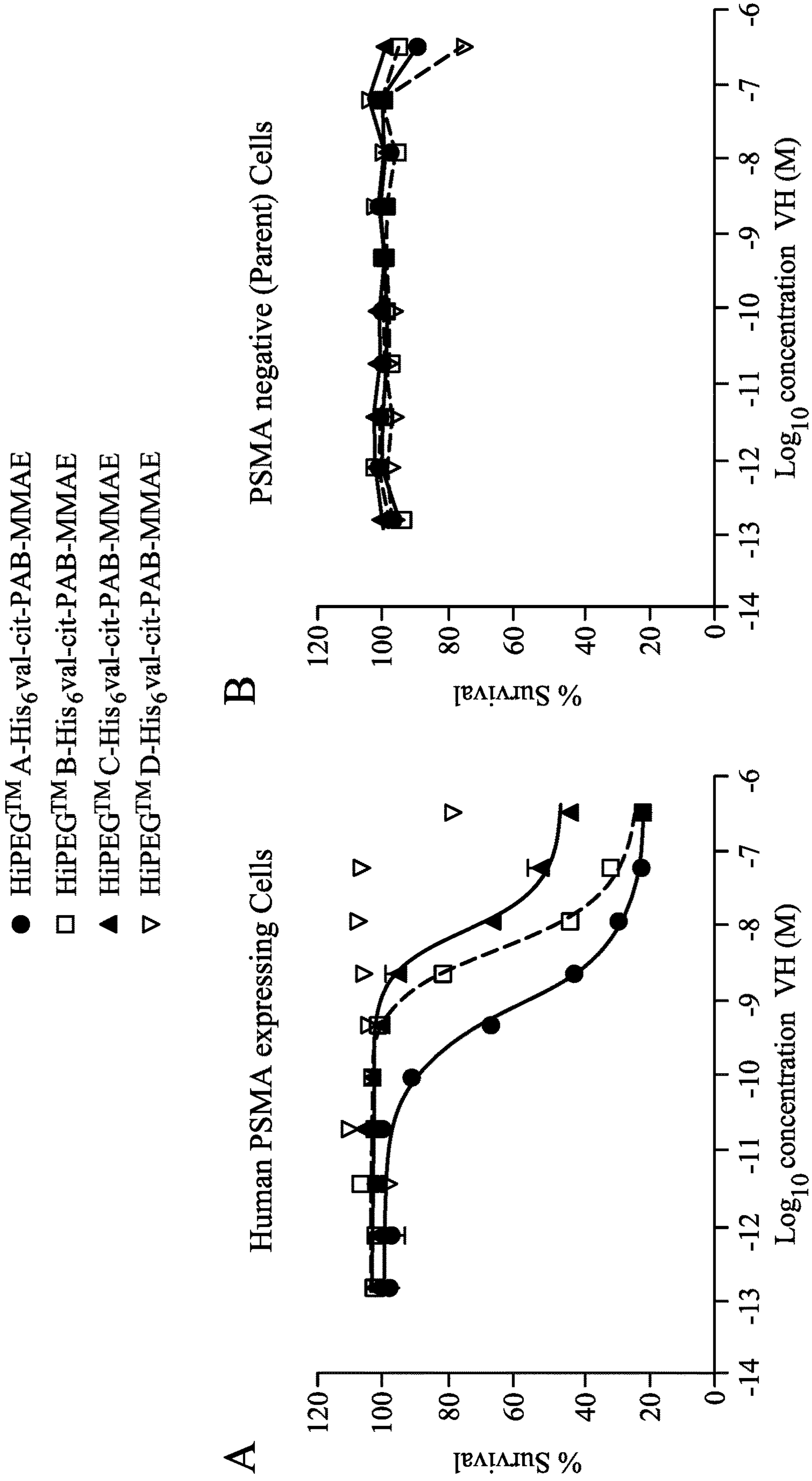
Figure 16:
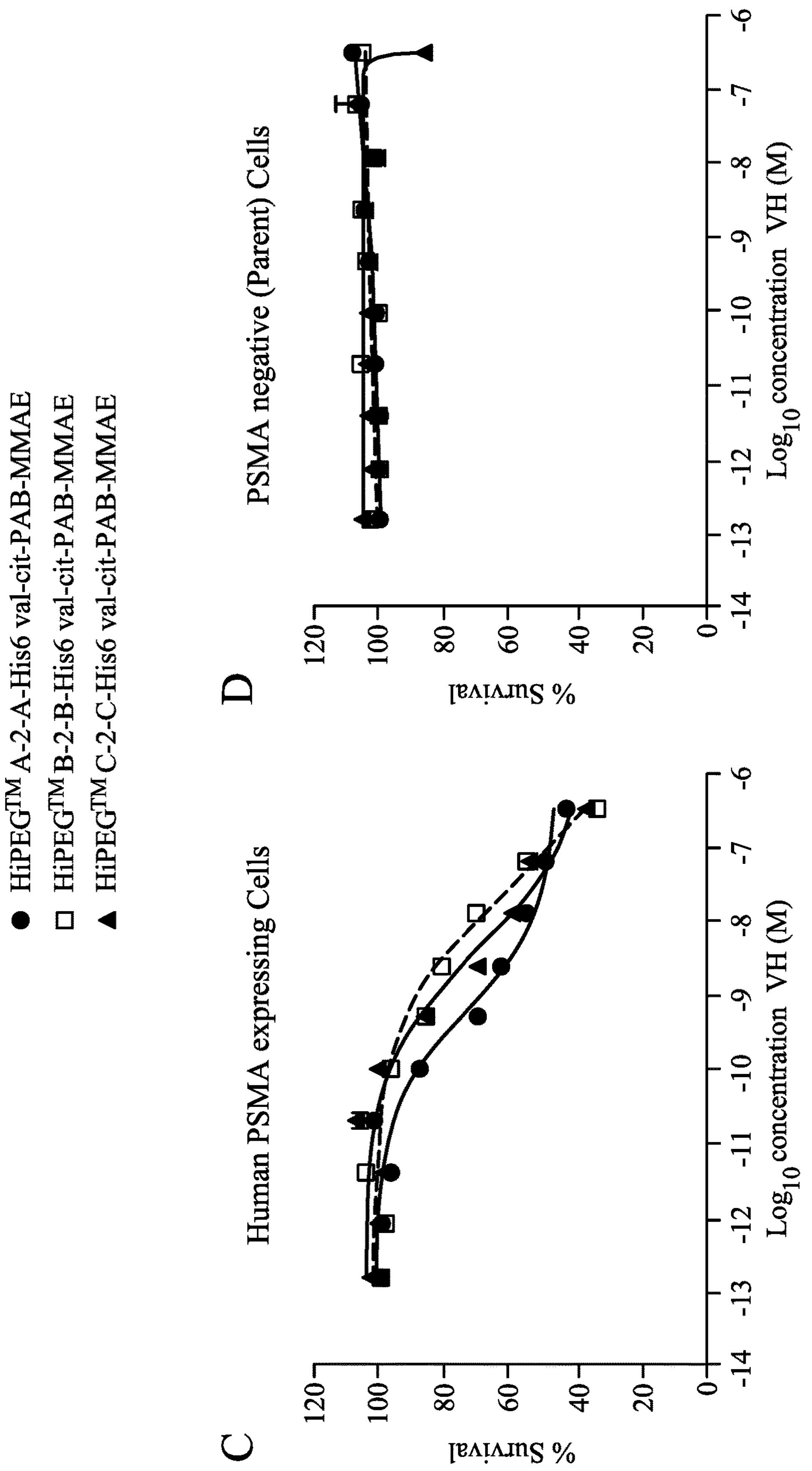
Figure 16:
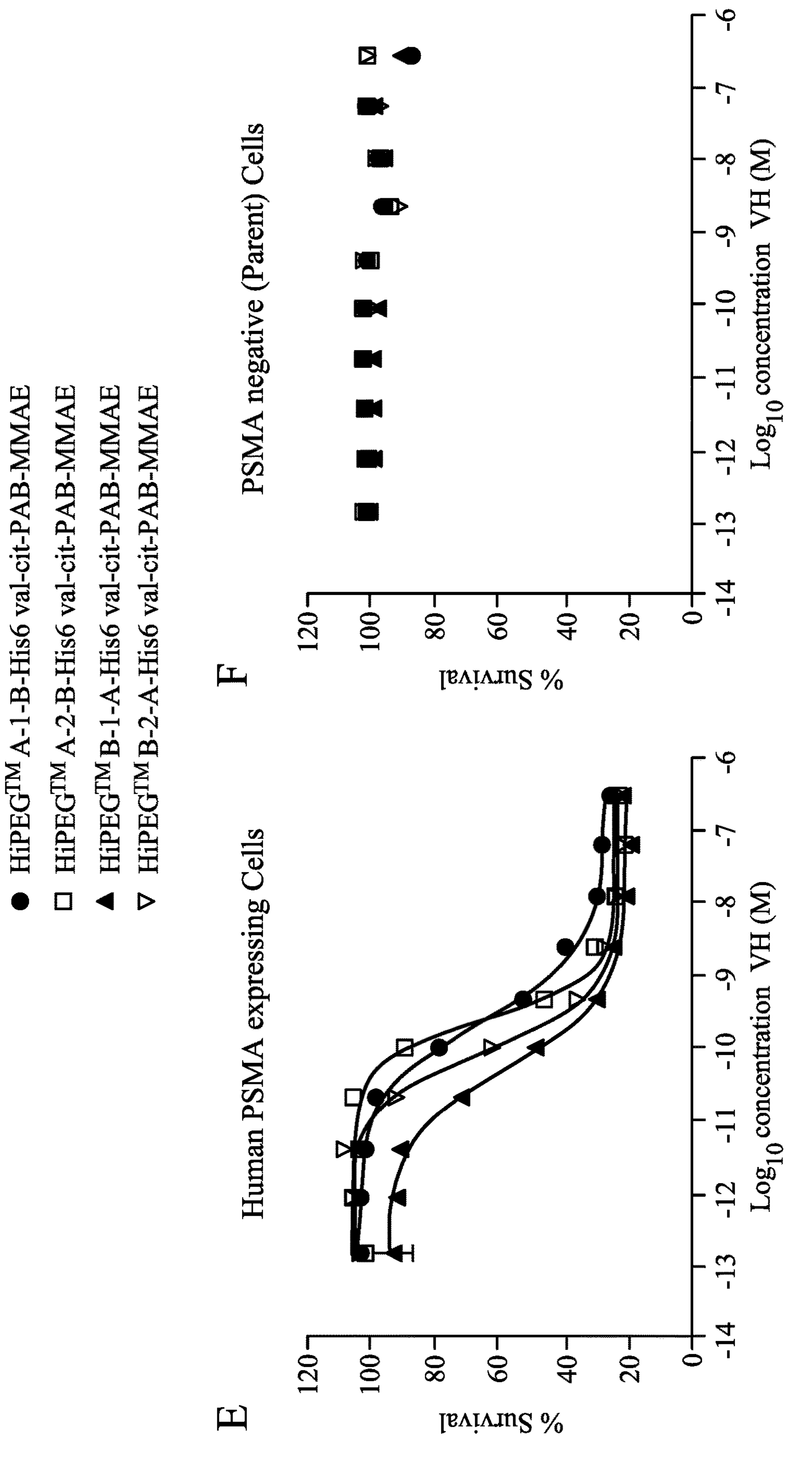

FIG. 16. shows in vitro cytotoxicity of monomeric MMAE-conjugated $V_H$ (A and B), bivalent $V_H$ (C and D) and biparatopic $V_H$ (E and F) on human cells stably expressing human PSMA protein and matched parental cells (PSMA negative) at a 48 hour incubation time point.

Figure 17:
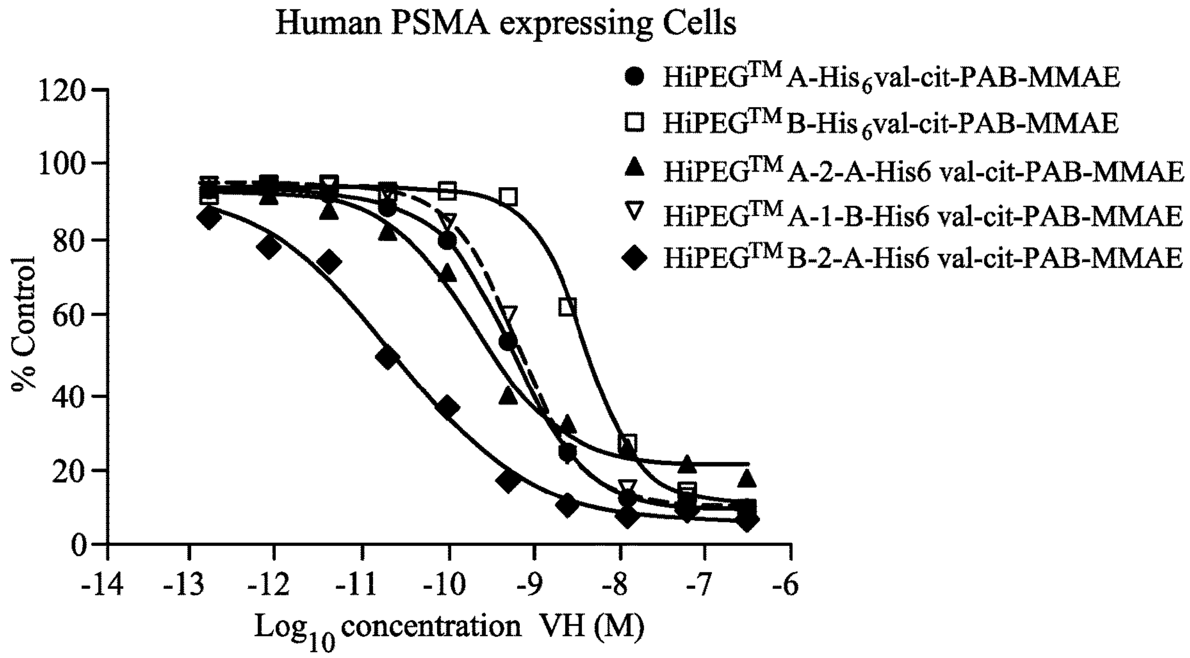

FIG. 17. shows in vitro cytotoxicity of MMAE-conjugated $V_H$ on human cells stably expressing human PSMA protein at a 72 hour incubation time point.

Figure 18:
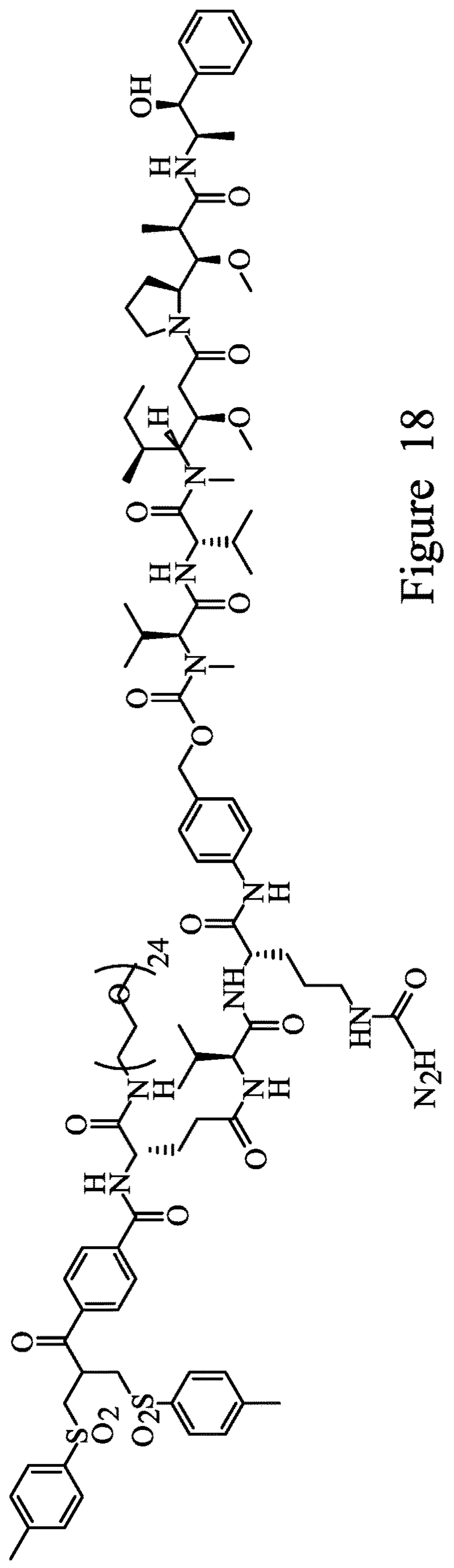

FIG. 18. shows the HiPEG™ val-cit-PAB-MMAE reagent (MW=2805 g/mol) used to prepare Humabody™ drug conjugates (HDCs).

Figure 19:
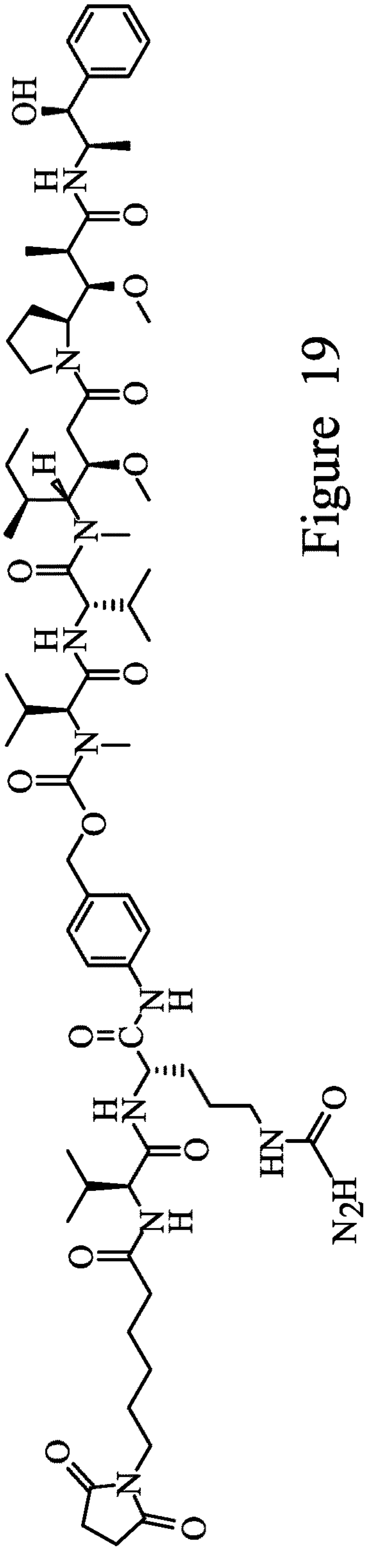

FIG. 19. shows the Maleimidocaproyl-valine-citrulline-p-aminobenzoyloxycarbonyl-monomethyl auristatin E (mc-val-cit-PAB-MMAE) conjugation reagent (MW=1317 g/mol) used to produce the Pro_006 control antibody drug conjugates (ADC).

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Sambrook et al., Molecular Cloning: A Laboratory Manual (2d ed., Cold Spring Harbor Laboratory Press, Cold Spring Harbor, N.Y. (1989)). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The invention provides isolated PSMA binding molecules, in particular those comprising at least one single $V_H$ domain antibody, that bind human PSMA, pharmaceutical compositions comprising such binding molecules, as well as isolated nucleic acids, recombinant expression vectors and isolated host cells for making such binding proteins and fragments. Also provided are methods of using the binding proteins disclosed herein to detect human PSMA, to inhibit human PSMA either in vitro or in vivo, and methods of treating disease. One aspect of the invention provides isolated human anti-human PSMA binding molecules, specifically those comprising, or consisting of, single $V_H$ domain antibodies that bind to human PSMA with high affinity a slow off rate.

The PSMA binding molecules of the invention bind to wild type human PSMA (Accession NO. Q04609). The sequence for the monomer is shown below (SEQ ID No. 250).

In one embodiment, the PSMA binding molecules of the invention bind to wild type human PSMA and/or cyno PSMA. The terms "PSMA binding molecule", "PSMA binding protein" "anti-PSMA single domain antibody" or "anti-PSMA antibody" as used herein all refer to a molecule capable of binding to the human PSMA antigen. The term "PSMA binding molecule" includes a PSMA binding protein. The binding reaction may be shown by standard methods (qualitative assays) including, for example, a binding assay, competition assay or a bioassay for determining the inhibition of PSMA binding to its receptor or any kind of binding assays, with reference to a negative control test in which an antibody of unrelated specificity. Suitable assays are shown in the examples.

An antibody or binding molecule of the invention, including a single domain antibody and multivalent or multispecific binding agent described herein, "which binds" or is "capable of binding" an antigen of interest, e.g. PSMA, is one that binds, i.e. targets, the PSMA antigen with sufficient affinity such that it is useful in therapy in targeting a cell or tissue expressing the antigen.

Binding molecules of the invention, including the single domain antibodies and multivalent or multispecific binding agents described herein, bind specifically to human PSMA. In other words, binding to the PSMA antigen is measurably different from a non-specific interaction. Preferably, the single domain antibodies of the invention bind to human PSMA and also bind to cyno PSMA. The term "specific binding" or "specifically binds to" or is "specific for" a particular polypeptide or an epitope on a particular polypeptide target as used herein can be exhibited, for example, by a molecule having a KD for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

The term "epitope" or "antigenic determinant" refers to a site on the surface of an antigen (e.g., PSMA) to which an immunoglobulin, antibody or antibody fragment, including a VH single domain antibody specifically binds. Generally, an antigen has several or many different epitopes and reacts with many different antibodies. The term specifically includes linear epitopes and conformational epitopes. Epitopes within protein antigens can be formed both from contiguous amino acids (usually a linear epitope) or non-contiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody or antibody fragment (i.e., epitope mapping) are well known in the art and include, for example, immunoblotting and immunoprecipitation assays, wherein overlapping or contiguous peptides from are tested for reactivity with a given antibody or antibody fragment. An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in different formats, using either labelled antigen or labelled antibody.

The invention provides isolated PSMA binding molecules that bind human PSMA, pharmaceutical compositions and formulations comprising such binding molecule, as well as isolated nucleic acids encoding such binding molecules, recombinant expression vectors and host cells comprising such nucleic acids for making such binding molecules. Also provided by the invention are methods of using the binding molecules disclosed herein to detect human PSMA, to inhibit human PSMA either in vitro or in vivo, and methods of treating disease. One preferred aspect of the invention provides isolated human anti-human PSMA binding molecules, specifically those comprising, or consisting of, at least one single human $V_H$ domain antibody that binds to human PSMA with high affinity, a slow off rate.

In one aspect, the invention relates to an isolated single variable domain antibody, an isolated variable single domain or an isolated immunoglobulin single variable domain wherein said isolated single domain antibody, isolated variable single domain or isolated immunoglobulin single variable domain binds to human PSMA. Binding molecules comprising at least one single domain antibody, variable single domain or immunoglobulin single variable domain are also within the scope of the invention. Fragments of the single domain antibody, variable single domain or immunoglobulin single variable domain that bind to human PSMA are also within the scope of the invention.

The terms "single domain antibody, variable single domain or immunoglobulin single variable domain (ISV)" are all well known in the art and describe the single variable fragment of an antibody that binds to a target antigen. These terms are used interchangeably herein. Single heavy chain variable domain antibodies ($V_H$) do not comprise an immunoglobulin light chain. As explained below, preferred embodiments of the various aspects of the invention relate to single heavy chain variable domain antibodies/immunoglobulin heavy chain single variable domains which bind a PSMA antigen in the absence of light chain. Human heavy chain single variable ($V_H$) domain antibodies are particularly preferred. Human heavy chain single variable $V_H$ are commonly abbreviated as $V_H$ domains. Single $V_H$ domains antibodies are also termed Humabody® herein. Humabody® is a registered trademark of Crescendo Biologics Ltd.

Thus, in some preferred embodiments, the isolated binding agents/molecules of the invention comprise or consist of at least one single domain antibody wherein said domain is preferably a human heavy chain variable domain. Thus, in one aspect, the binding agents of the invention comprise or consist of at least one human immunoglobulin single variable heavy chain domain; they are devoid of $V_L$ domains.

Each single $V_H$ domain antibody comprises three CDRs and four FRs, arranged from amino-terminus to carboxy-terminus in the following order: FR1-CDR1-FR2-CDR2-FR3-CDR3-FR4.

Thus, in one embodiment of the invention, the domain is a human variable heavy chain ($V_H$) domain with the following formula FR1-CDR1-FR2-CDR2-FR3-CDR3-FR4. In one embodiment of the invention, the binding molecule includes an antigen binding fragment thereof.

The term "isolated" single domain antibody refers to a single domain antibody that is substantially free of other single domain antibodies, antibodies or antibody fragments having different antigenic specificities. Moreover, an isolated single domain antibody may be substantially free of other cellular material and/or chemicals.

"Homology" generally refers to the percentage of amino acid residues in the candidate sequence that are identical with the residues of the polypeptide with which it is compared, after aligning the sequences and in some embodiments after introducing gaps, if necessary, to achieve the maximum percent homology, and not considering any conservative substitutions as part of the sequence identity. Thus, the percentage homology between two amino acid sequences is equivalent to the percentage identity between the two sequences. Neither N- or C-terminal extensions, tags or insertions shall be construed as reducing identity or homology. Methods and computer programs for the alignment are well known.

The term "antibody", broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. In a full-length antibody, each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

An antibody fragment is a portion of an antibody, for example as $F(ab')_2$, Fab, Fv, sFv and the like. Functional fragments of a full length antibody retain the target specificity of a full length antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs. scFv fragments (~25 kDa) consist of the two variable domains, $V_H$ and $V_L$. Naturally, $V_H$ and $V_L$ domain are non-covalently associated via hydrophobic interaction and tend to dissociate. However, stable fragments can be engineered by linking the domains with a hydrophilic flexible linker to create a single chain Fv (scFv). The smallest antigen binding fragment is the single variable fragment, namely the $V_H$ or $V_L$ domain. Binding to a light chain/heavy chain partner respectively is not required for target binding. Such fragments are used in single domain antibodies. A single domain antibody (~12 to 15 kDa) therefore has either the $V_H$ or $V_L$ domain.

In certain embodiments, the isolated binding molecules of the invention comprise or consist of at least one single domain antibody wherein said domain is a $V_H$ domain. Thus, in one aspect, the binding molecules of the invention comprise or consist of at least one immunoglobulin single variable heavy chain domain antibody (sVD, sdAb or ISV) that has a $V_H$ domain, but is devoid of $V_L$ domains. As further described herein, the binding molecule may comprise two or more single $V_H$ domain antibodies. Such binding molecules may be monospecific or multispecific, monovalent or multivalent as explained in further detail below.

Thus, in some preferred embodiments of the invention, the binding molecule does not comprise a light chain. In some embodiments, the binding molecule does not comprise heavy chain domains $C_H2$ and $C_H3$. In some embodiments, the binding molecule does not comprise a hinge region and heavy chain domains $C_H2$ and $C_H3$. In some embodiments, the binding molecule does not comprise heavy chain domains $C_H1$, $C_H2$, and $C_H3$. In some embodiments the binding molecule does not comprise heavy chain domain $C_H1$, a hinge region heavy chain domain $C_H2$ and heavy chain domain $C_H3$. In some embodiments the binding molecule does not comprise a light chain, a heavy chain domain $C_H1$, a hinge region heavy chain domain $C_H2$ and heavy chain domain $C_H3$.

Each $V_H$ domain comprises three CDRs and four FRs, arranged from amino-terminus to carboxy-terminus in the following order: FR1, CDR1, FR2, CDR2, FR3, CDR3, FR4. Modifications to the $V_H$ framework may be made to improve binding properties. For example, the $V_H$ domain may comprise C or N-terminal extensions. In one embodiment, the $V_H$ domain comprises C-terminal extensions of from 1 to 10, for example 1, 2, 3, 4, 5, 6, 7, 8, 9 or 10 additional amino acids. In one embodiment, the $V_H$ domain comprises C-terminal extensions of from 1 to 12 amino acid residues, for example 1, 2, 3, 4, 5, 6, 7, 8, 9 or 10 additional amino acids of the $C_H1$ domain. In one embodiment, said extension comprises at least 1 alanine residue, for example a single alanine residue, a pair of alanine residues or a triplet of alanine residues. Such extended $V_H$ domains are within the scope of the invention. Also within the scope of the invention are $V_H$ domains that comprise additional C or N-terminal residues, for example linker residues and/or His tags, e.g., hexa-His (SEQ ID No. 251) or myc tags. Additional residues of the vector may also be present, for example in addition to tags. Binding molecules used may have the additional residues (SEQ ID No. 252).

According to the various aspects and embodiments of the invention, the variable domain of the single domain antibodies of the invention is preferably a human variable domain ($V_H$). As used herein, a human $V_H$ domain includes a fully human or substantially fully human $V_H$ domain. As used herein, the term human $V_H$ domain also includes $V_H$ domains that are isolated from heavy chain only antibodies made by transgenic mice expressing fully human immunoglobulin heavy chain loci, in particular in response to an immunisation with an antigen of interest, for example as described in WO2016/062990 and in the examples. In one embodiment, a human $V_H$ domain can also include a $V_H$ domain that is derived from or based on a human $V_H$ domain amino acid or nucleic acid sequence encoding such $V_H$ domain.

Thus, the term includes variable heavy chain regions derived from or encoded by human germline immunoglobulin sequences. A substantially human $V_H$ domain or $V_H$ domain that is derived from or based on a human $V_H$ domain may include amino acid residues not encoded by human germline immunoglobulin sequences (e.g., mutations introduced in vitro, e.g. by random or site-specific mutagenesis, or introduced by somatic mutation in vivo). The term "human $V_H$ domain" therefore also includes a substantially human $V_H$ domain wherein one or more amino acid residue has been modified. For example, a substantially human $V_H$ domain the $V_H$ domain may include up to 10, for example 1, 2, 3, 4 or 5 amino acid modifications compared to a fully human sequence. However, the term "human $V_H$ domain" or "substantially human $V_H$ domain", as used herein, is not intended to include antibodies in which CDR sequences derived from the germline of another mammalian species, such as a mouse, have been grafted onto human framework sequences. Preferably, the term "human $V_H$ domain", as used herein, is also not intended to include camelized $V_H$ domains, that is human $V_H$ domains that have been specifically modified, for example in vitro by conventional mutagenesis methods to select predetermined positions in the $V_H$ domains sequence and introduce one or more point mutation at the predetermined position to change one or more predetermined residue to a specific residue that can be found in a camelid $V_{HH}$ domain.

As used herein, the term $V_H$ or "variable domain" refers to immunoglobulin variable domains defined by Kabat et al., Sequences of Immunological Interest, $5^{th}$ ed., U.S. Dept. Health & Human Services, Washington, D.C. (1991). The numbering and positioning of CDR amino acid residues within the variable domains is in accordance with the well-known Kabat numbering convention.

More particularly, the invention provides a single $V_H$ domain antibody or a binding molecule comprising one or more single $V_H$ domain antibody wherein said single $V_H$ domain antibody binds to human PSMA with an affinity, a Kon-rate, a Koff rate, KD and/or KA, EC50 and IC50 values as further described herein, in particular in the examples. Assays suitable for measuring these values are also shown in the examples.

A binding molecule of the invention, in particular the single $V_H$ domain antibody, comprises or consists of an amino acid sequence and preferred sequences and/or parts thereof, such as CDRs, as defined herein.

The term "CDR" refers to the complementarity-determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs have been defined differently according to different systems. The system described by Kabat is used herein. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242).

As described in more detail in the experimental part, single $V_H$ domain antibodies were isolated and grouped into families based on sequence homology in the CDR3 sequence. Through a process of optimization, a panel of variant single $V_H$ domain antibodies with a CDR sequence derived from a parent CDR sequence were also generated to improve affinities to PSMA and/or improve potencies compared to the parent molecule.

In one aspect, the invention relates to a binding molecule capable of binding human PSMA comprising or consisting of or wherein the PSMA binding part comprises or consists of a single $V_H$ domain antibody comprising or consisting of a family 1 member as shown in table 1a or a family-1 like sequence, that is a variant of family 1 as shown in table 1a as defined herein. In one embodiment, the binding molecule comprises or consists of at least one single $V_H$ domain antibody capable of binding PSMA, preferably human PSMA, comprising a family 1 single $V_H$ domain antibody as shown in table 1a or a variant of family 1 as shown in table 1a as defined herein. Thus, the invention relates to a single $V_H$ domain antibody capable of binding PSMA, preferably human PSMA, wherein said single $V_H$ domain antibody is as shown in table 1a or is a variant of family 1 as shown in table 1a as defined herein. The single $V_H$ domain antibody may include CDR1, CDR2 and CDR3 sequences, as shown in below. CDR sequences and full length $V_H$ sequences in family 1a are numbered according to Table 1a as shown below.

| Name | CDR1 | CDR2 | CDR3 | $V_H$ Full length sequence |
|---|---|---|---|---|
| 1.21 | SEQ ID NO. 1 SYALS | SEQ ID NO. 2 SIGENDGTTDYADFVKG | SEQ ID NO. 3 DGVH | SEQ ID NO. 4 EVQLLESGGGLVQPGGSLRLSCAASGFSFSSYALSWVRQAPGKGLEWVSSIGENDGTTDYADFVKGRFTISRDNSKNTLYLQMNSLRVEDTAVYYCVKDGVHWGQGTLVTVSS |
| 1.22 | SEQ ID NO. 5 SYALS | SEQ ID NO. 6 SIGENDGTTDYADNVKG | SEQ ID NO. 7 DGVH | SEQ ID NO. 8 EVQLLESGGGLVQPGGSLRLSCAASGFSFSSYALSWVRQAPGKGLEWVSSIGENDGTTDYADNVKGRFTISRDNSKNTLYLQMNSLRVEDTAVYYCVKDGVHWGQGTLVTVSS |
| 1.23 | SEQ ID NO. 9 SYALS | SEQ ID NO. 10 SIGENDGTTDYAADVKG | SEQ ID NO. 11 DGVH | SEQ ID NO. 12 EVQLLESGGGLVQPGGSLRLSCAASGFSFSSYALSWVRQAPGKGLEWVSSIGENDGTTDYAADVKGRFTISRDNSKNTLYLQMNSLRVEDTAVYYCVKDGVHWGQGTLVTVSS |
| 1.24 | SEQ ID NO. 13 SYALS | SEQ ID NO. 14 SIGENDGTTDYADVVKG | SEQ ID NO. 15 DGVH | SEQ ID NO. 16 EVQLLESGGGLVQPGGSLRLSCAASGFSFSSYALSWVRQAPGKGLEWVSSIGENDGTTDYADVVKGRFTISRDNSKNTLYLQMNSLRVEDTAVYYCVKDGVHWGQGTLVTVSS |
| 1.25 | SEQ ID NO. 17 SYALS | SEQ ID NO. 18 SIGENDGTTDYAAFVKG | SEQ ID NO. 19 DGVH | SEQ ID NO. 20 EVQLLESGGGLVQPGGSLRLSCAASGFSFSSYALSWVRQAPGKGLEWVSSIGENDGTTDYAAFVKGRFTISRDNSKNTLYLQMNSLRVEDTAVYYCVKDGVHWGQGTLVTVSS |
| 1.26 | SEQ ID NO. 21 SYALS | SEQ ID NO. 22 SIGENDGTTDYADTVKG | SEQ ID NO. 23 DGVH | SEQ ID NO. 24 EVQLLESGGGLVQPGGSLRLSCAASGFSFSSYALSWVRQAPGKGLEWVSSIGENDGTTDYADTVKGRFTISRDNSKNTLYLQMNSLRVEDTAVYYCVKDGVHWGQGTLVTVSS |
| 1.27 | SEQ ID NO. 25 SYALS | SEQ ID NO. 26 SIGENDGTTDYADAVKG | SEQ ID NO. 27 DGVH | SEQ ID NO. 28 EVQLLESGGGLVQPGGSLRLSCAASGFSFSSYALSWVRQAPGKGLEWVSSIGENDGTTDYADAVKGRFTISRDNSKNTLYLQMNSLRVEDTAVYYCVKDGVHWGQGTLVTVSS |
| 1.28 | SEQ ID NO. 29 SYALS | SEQ ID NO. 30 SIGENDGTTDYAASVKG | SEQ ID NO. 31 DGVH | SEQ ID NO. 32 EVQLLESGGGLVQPGGSLRLSCAASGFSFSSYALSWVRQAPGKGLEWVSSIGENDGTTDYAASVKGRFTISRDNSKNTLYLQMNSLRVEDTAVYYCVKDGVHWGQGTLVTVSS |
| 1.29 | SEQ ID NO. 33 SYALS | SEQ ID NO. 34 SIGENDGTTDYAAYVKG | SEQ ID NO. 35 DGVH | SEQ ID NO. 36 EVQLLESGGGLVQPGGSLRLSCAASGFSFSSYALSWVRQAPGKGLEWVSSIGENDGTTDYAAYVKGRFTISRDNSKNTLYLQMNSLRVEDTAVYYCVKDGVHWGQGTLVTVSS |
| 1.30 | SEQ ID NO. 37 SYALS | SEQ ID NO. 38 SIGENDGTTDYAATVKG | SEQ ID NO. 39 DGVH | SEQ ID NO. 40 EVQLLESGGGLVQPGGSLRLSCAASGFSFSSYALSWVRQAPGKGLEWVSSIGENDGTTDYAATVKGRFTISRDNSKNTLYLQMNSLRVEDTAVYYCVKDGVHWGQGTLVTVSS |

Table 1a. This shows sequences of single $V_H$ domain antibodies that are within the scope of the invention.

| Name | $V_H$ Full length sequence |
|---|---|
| 1.1 | SEQ ID NO. 41 EVQLLESGGGLVQPGGSLRLSCAASGFSFSSYAMSWVRQAPGKGLEWVSSIGENDGTTDYADSVKGRFTISRDNSKSMLYLQMNSLRVEDTAVYYCVKDGVHWGQGTLVTVSS |
| 1.2 | SEQ ID NO. 42 EVQLVESGGGLVQPGGSLRLSCAASGFTFSSYAMSWVRQAPGKGLEWVSSIGDNNNSTEYADSVKGRFTISRDNSKSTLYLQMNSLSAEDTAVYYCVKDGVHWGQGTLVTVSS |
| 1.3 | SEQ ID NO. 43 EVQLVESGGGLVQPGGSLRLSCAASGFSFSSYAMSWVRQAPGKGLEWVSSIGDNNNSTDYADSVKGRFTISRDNSKSTLYLQMNSLRAEDTAVYYCVKDGVHWGQGTLVTVSS |
| 1.4 | SEQ ID NO. 44 EVQLVESGGGLVQPGGSLRLSCAASGFTFSSYAMSWVRQAPGKGLEWVSSIGDGTTYYADSVKGRFTISRDNSKSTLYLQMNSLRAEDTAVYYCAKDGVHWGQGTLVTVSS |
| 1.5 | SEQ ID NO. 45 EVQLVESGGGLVQPGGSLRLSCAASGFTFSTYAMSWVRQAPGKGLEWVSSIGENDRTTYYVDSVKGRFTISRDNSKSTLYLQMNSLRAEDTAVYYCAKDGVHWGQGTLVTVSS |
| 1.6 | SEQ ID NO. 46 QVQLVESGGGLVQPGGSLRLSCAASGFTFSSYAMSWVRQAPGKGLEWVSSIGDNNRTTYYADSVKGRFTISRDNSKSTLYLQMNSLRAEDTAVYYCAKDGVHWGQGTLVTVSS |
| 1.7 | SEQ ID NO. 47 EVQLVESGGGLVQPGGSLRLSCAASGFTFSSYAMSWVRQAPGKGLEWVSSIGDGTTYYADSVKGRFTISRDNSKSTLYLQMNSLRAEDTAVYYCAKDGVHWGQGTLVTVSS |
| 1.8 | SEQ ID NO. 48 EVQLLESGGGLVQPGGSLRLSCAASGFSFSSYAMSWVRQAPGKGLEWVSSIGENDGTTDYADSVKGRFTISRDNSKNTLYLQMNSLRVEDTAVYYCVKDGVHWGQGTLVTVSS |
| 1.9 | SEQ ID NO. 49 EVQLLESGGGLVQPGGSLRLSCAASGFSFSSYALSWVRQAPGKGLEWVSSIGENDGTTDYADSVKGRFTISRDNSKNTLYLQMNSLRVEDTAVYYCVKDGVHWGQGTLVTVSS |
| 1.10 | SEQ ID NO. 50 EVQLLESGGGLVQPGGSLRLSCAASGFSFSSYALSWVRQAPGKVGLEWSSIGENNATTDYADFVKGRFTISRDNSKNTLYLQMNSLRVEDTAVYYCVKDGVHWGQGTLVTVSS |
| 1.11 | SEQ ID NO. 51 EVQLLESGGGLVQPGGSLRLSCAASGFSFSSYALSWVRQAPGKGLEWVSSIGENNDTTDYADNVKGRFTISRDNSKNTLYLQMNSLRVEDTAVYYCVKDGVHWGQGTLVTVSS |
| 1.12 | SEQ ID NO. 52 EVQLLESGGGLVQPGGSLRLSCAASGFSFSSYALSWVRQAPGKGLEWVSSIGENNATTDYADAVKGRFTISRDNSKNTLYLQMNSLRVEDTAVYYCVKDGVHWGQGTLVTVSS |
| 1.13 | SEQ ID NO. 53 EVQLLESGGGLVQPGGSLRLSCAASGFSFSSYALSWVRQAPGKGLEWVSSIGENNHTTDYAADVKGRFTISRDNSKNTLYLQMNSLRVEDTAVYYCVKDGVHWGQGTLVTVSS |
| 1.14 | SEQ ID NO. 54 EVQLLESGGGLVQPGGSLRLSCAASGFSFSSYALSWVRQAPGKGLEWVSSIGENNATTDYADVVKGRFTISRDNSKNTLYLQMNSLRVEDTAVYYCVKDGVHWGQGTLVTVSS |
| 1.15 | SEQ ID NO. 55 EVQLLESGGGLVQPGGSLRLSCAASGFSFSSYALSWVRQAPGKGLEWVSSIGENNHTTDYAAFVKGRFTISRDNSKNTLYLQMNSLRVEDTAVYYCVKDGVHWGQGTLVTVSS |

-continued

| Name | $V_H$ Full length sequence |
|---|---|
| 1.16 | SEQ ID NO. 56 EVQLLESGGGLVQPGGSLRLSCAASGFSFSSYALSWVRQAPGK GLEWVSSIGENNHTTDYADTVKGRFTISRDNSKNTLYLQMNSL RVEDTAVYYCVKDGVHWGQGTLVTVSS |
| 1.17 | SEQ ID NO. 57 EVQLLESGGGLVQPGGSLRLSCAASGFSFSSYALSWVRQAPGK GLEWVSSIGENNDTTDYADAVKGRFTISRDNSKNTLYLQMNSL RVEDTAVYYCVKDGVHWGQGTLVTVSS |
| 1.18 | SEQ ID NO. 58 EVQLLESGGGLVQPGGSLRLSCAASGFSFSSYALSWVRQAPGK GLEWVSSIGENNATTDYAASVKGRFTISRDNSKNTLYLQMNSL RVEDTAVYYCVKDGVHWGQGTLVTVSS |
| 1.19 | SEQ ID NO. 59 EVQLLESGGGLVQPGGSLRLSCAASGFSFSSYALSWVRQAPGK GLEWVSSIGENNDTTDYAAYVKGRFTISRDNSKNTLYLQMNSL RVEDTAVYYCVKDGVHWGQGTLVTVSS |
| 1.20 | SEQ ID NO. 60 EVQLLESGGGLVQPGGSLRLSCAASGFSFSSYALSWVRQAPGK GLEWVSSIGENNHTTDYAATVKGRFTISRDNSKNTLYLQMNSL RVEDTAVYYCVKDGVHWGQGTLVTVSS |

Table 1b This shows other family 1 members that share or have similar CDR3 sequences with those family members listed in table 1a.

In one embodiment, the single $V_H$ domain antibody comprises CDR1, 2, and 3 sequences as set out below. Thus, according to the invention, the single $V_H$ domain antibody may be selected from one of the following: a single $V_H$ domain antibody comprising a CDR1 sequence comprising SEQ ID NO. 1, a CDR2 sequence comprising SEQ ID NO. 2 and a CDR3 sequence comprising SEQ ID NO. 3; a single $V_H$ domain antibody comprising a CDR1 sequence comprising SEQ ID NO. 5, a CDR2 sequence comprising SEQ ID NO. 6 and a CDR3 sequence comprising SEQ ID NO. 7; a single $V_H$ domain antibody comprising a CDR1 sequence comprising SEQ ID NO. 9, a CDR2 sequence comprising SEQ ID NO. 10 and a CDR3 sequence comprising SEQ ID NO. 11; a single $V_H$ domain antibody comprising a CDR1 sequence comprising SEQ ID NO. 13, a CDR2 sequence comprising SEQ ID NO. 14 and a CDR3 sequence comprising SEQ ID NO. 15; a single $V_H$ domain antibody comprising a CDR1 sequence comprising SEQ ID NO. 17, a CDR2 sequence comprising SEQ ID NO. 18 and a CDR3 sequence comprising SEQ ID NO. 19; a single $V_H$ domain antibody comprising a CDR1 sequence comprising SEQ ID NO. 21, a CDR2 sequence comprising SEQ ID NO. 22 and a CDR3 sequence comprising SEQ ID NO. 23; a single $V_H$ domain antibody comprising a CDR1 sequence comprising SEQ ID NO. 25, a CDR2 sequence comprising SEQ ID NO. 26 and a CDR3 sequence comprising SEQ ID NO. 27; a single $V_H$ domain antibody comprising a CDR1 sequence comprising SEQ ID NO. 29, a CDR2 sequence comprising SEQ ID NO. 30 and a CDR3 sequence comprising SEQ ID NO. 31; a single domain $V_H$ domain antibody comprising a CDR1 sequence comprising SEQ ID NO. 33, a CDR2 sequence comprising SEQ ID NO. 34 and a CDR3 sequence comprising SEQ ID NO. 35; a single $V_H$ domain antibody comprising a CDR1 sequence comprising SEQ ID NO. 37, a CDR2 sequence comprising SEQ ID NO. 38 and a CDR3 sequence comprising SEQ ID NO. 39. In one embodiment, the single $V_H$ domain antibody of the invention comprises a CDR1 sequence comprising SEQ ID NO. 25, a CDR2 sequence comprising SEQ ID NO. 26 and a CDR3 sequence comprising SEQ ID NO. 27.

In one embodiment, said single $V_H$ domain antibody comprises or consists of a sequence selected from SEQ ID NOs 4, 8, 12, 16, 20, 24, 28, 32, 36 or 40. In one embodiment, the single $V_H$ domain antibody comprises or consists of a sequence selected from SEQ ID NOs 4, 8, 12, 16, 20, 24, 28, 32, 36 or 40 or a sequence with at least 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto but wherein no changes are made to CDR2. In one embodiment, said single $V_H$ domain antibody comprises a CDR2 as identified in any of SEQ ID NOs 2, 6, 10, 14, 18, 22, 26, 30, 34 or 38. In one embodiment, said CDR2 is SEQ ID NO. 26. In one embodiment, said modification(s) is in FR1, CDR1, FR2, CDR3, FR3, FR4.

In one embodiment, the single $V_H$ domain antibody has a $V_H$ domain that comprises or consists of SEQ ID NO. 4, 8, 12, 16, 20, 24, 28, 32, 36 or 40. In one embodiment, the binding molecules is selected from $V_H$ single domain antibodies 1.21, 1.22, 1.23, 1.24, 1.25, 1.26, 1.27, 1.28, 1.29 or 1.30. In one embodiment, the single $V_H$ domain antibody has a $V_H$ domain that comprises or consists of SEQ ID NO. 28.

Thus, in some embodiments, the invention also provides variant $V_H$ single domain antibodies that are variants of parent molecules 1.21 to 1.30 as shown in Table 1a, wherein these variants do not have a modification in the CDR2 sequence. Such variants have one or more amino acid substitution, deletion, insertion or other modification, and which retain a biological function of the parent single domain antibody. Thus, a variant $V_H$ single domain antibody retains binding to human PSMA. The parent single domain antibody can be sequence engineered to arrive at the variant. Modifications may include one or more substitution, deletion or insertion of one or more codons encoding the single domain antibody or polypeptide that results in a change in the amino acid sequence as compared with the native sequence $V_H$ single domain antibody or polypeptide. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence. A variant of a $V_H$ single domain antibody as used herein generally has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology to the non-variant molecule, preferably at least 90%, 91%, 92%, 93%, 94%, 95%, 96%, 97%, 98% or 99% sequence homology. Variants of a $V_H$ single domain antibody as shown in table 1a preferably do not have any modifications in the CDR2 region.

In one embodiment, the invention encompasses a $V_H$ single domain antibody as defined in SEQ ID NO. 41 or 48 and which has modifications at positions 62 and 63, but no modification at positions 55 and 56. Residues DS at positions 62 and 63 may for example be modified to AT, DF, DN, DA, AD, DV, AF, DT, DA, AS or AY.

In one embodiment, the modification in a variant is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody of the invention can be replaced with other amino acid residues from the same side chain family and the altered antibody can be tested for retained function (i.e., the functions set forth in (c) through (I) above) using the functional assays described herein.

In some embodiments, the variant of the single domain antibody selected from those shown in Table 1a that comprises one or more sequence modification and has improvements in one or more of a property such as binding affinity, specificity, thermostability, expression level, effector function, glycosylation, reduced immunogenicity, or solubility as compared to the unmodified single domain antibody.

A skilled person will know that there are different ways to identify, obtain and optimise the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used. The invention therefore also comprises sequence optimised variants of the single domain antibodies described herein.

In one embodiment, modifications can be made to decrease the immunogenicity of the single domain antibody. For example, one approach is to revert one or more framework residues to the corresponding human germline sequence. More specifically, a single domain antibody that has undergone somatic mutation may contain framework residues that differ from the germline sequence from which the single domain antibody is derived. Such residues can be identified by comparing the single domain antibody framework sequences to the germline sequences from which the single domain antibody is derived. To return one or more of the amino acid residues in the framework region sequences to their germline configuration, the somatic mutations can be "backmutated" to the germline sequence by, for example, site-directed mutagenesis or PCR-mediated mutagenesis.

Another type of framework modification involves mutating one or more residues within the framework region, or even within one or more CDR regions, to remove T cell epitopes to thereby reduce the potential immunogenicity of the antibody. In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

The family 1 or variants (family 1-like) binding molecules preferably have KD, Koff, KA, Kd, $EC_{50}$ and $IC_{50}$ values as further described herein and as shown in the examples. The term "KD" as used in this application refers to the "equilibrium dissociation constant" and refers to the value obtained in a titration measurement at equilibrium, or by dividing the dissociation rate constant (Koff) by the association rate constant (Kon). "KA" as used in this application refers to the affinity constant. The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay and assays described in the examples can be used to test the binding molecules of the invention.

In one aspect, the invention also relates to isolated nucleic acid sequences comprising or consisting of a sequence selected from SEQ ID NOs. 61 to 70 which encode $V_H$ domains 1.21 to 1.30. In one embodiment, the sequence is SEQ ID NO. 67.

Nucleic acid may include DNA and/or RNA. In one aspect, the present invention provides a nucleic acid that codes for a CDR or set of CDRs or a $V_H$ domain of the invention as defined above. A nucleic acid according to the present invention may comprise DNA or RNA and may be wholly or partially synthetic or recombinantly produced. Reference to a nucleotide sequence as set out herein encompasses a DNA molecule with the specified sequence, and encompasses a RNA molecule with the specified sequence in which U is substituted for T, unless context requires otherwise.

Furthermore, the invention relates to a nucleic acid construct comprising at least one nucleic acid defined above. The construct may be in the form of a plasmid, vector, transcription or expression cassette. The invention also relates to an isolated recombinant host cell comprising one or more nucleic acid construct as described above. The host cell may be a bacterial, yeast, viral, mammalian or other suitable host cell. In one embodiment, the cell is an *E. coli* cell. In another embodiment, the cell is a yeast cell. In another embodiment, the cell is a Chinese Hamster Ovary (CHO) cell.

A binding molecule described herein may be provided as a fusion protein with one or more additional protein moiety. For example, the single domain antibody, described herein (a first moiety) may be provided as a fusion with a second moiety.

The second moiety may comprise a $V_H$ domain that is also specific for human PSMA thus providing a bivalent binding molecule. In one embodiment, the binding molecule is biparatopic. Biparatopic binding molecules comprise antigen-binding moieties that bind to different epitopes. Biparatopic binding molecules of the present invention can be constructed using methods known art.

For example, to generate a bivalent binding molecule, two single domain antibodies of the invention may be connected, the two binding molecules may be from the same family or from different families of binding molecules of the invention. For example, a family 1 single $V_H$ domain antibody as described above and for example as shown in Table 1 or a variant thereof may be linked to a family 2 to 15 or family 2-like to 15-like single $V_H$ domain antibody. A family-like single $V_H$ domain antibody refers to a variant as defined elsewhere herein. In one embodiment of the invention, a $V_H$ as defined for single $V_H$ domain antibody 1.27 (SEQ ID NO. 28) is connected to another single $V_H$ domain antibody selected from family 2 or family 3, for example to the single $V_H$ domain antibody as defined for clone 2.1. Two or more single $V_H$ domain antibody may be connected by a linker, for example a polypeptide linker. Suitable linkers, for example comprising linker include GS residues such as $(Gly_4Ser)_n$, where n=from 1 to 10, e.g., 1, 2, 3, 4, 5, 6, 7, 8, 9 or 10.

TABLE 2

Family 2 single $V_H$ domain antibodies.

| Name | $V_H$ Full length sequence |
|---|---|
| 2.1-2.25 | SEQ ID NO. 71-95 |

TABLE 3

Family 3 members

| Name | $V_H$ Full length sequence |
|---|---|
| 3.1-3.24 | SEQ ID NO. 96-119 |

TABLE 4

Family 4 members

| Name | $V_H$ Full length sequence |
|---|---|
| 4.1-4.4 | SEQ ID NO. 120-123 |

TABLE 5

Family 5 members

| Name | $V_H$ Full length sequence |
|---|---|
| 5.1-5.2 | SEQ ID NO. 124-125 |

TABLE 6

Family 6 members

| Name | $V_H$ Full length sequence |
|---|---|
| 6.1-6.7 | SEQ ID NO. 126-132 |

TABLE 7

Family 7 members

| Name | $V_H$ Full length sequence |
|---|---|
| 7.1-7.8 | SEQ ID NO. 133-140 |

TABLE 8

Family 8 members

| Name | $V_H$ Full length sequence |
|---|---|
| 8.1 | SEQ ID NO. 141 |

TABLE 9

Family 9 members

| Name | $V_H$ Full length sequence |
|---|---|
| 9.1 | SEQ ID NO. 142 |

TABLE 10

Family 10 members

| Name | $V_H$ Full length sequence |
|---|---|
| 10.1 | SEQ ID NO. 143 |

TABLE 11

Family 11 members

| Name | $V_H$ Full length sequence |
|---|---|
| 11.1 | SEQ ID NO. 144 |

TABLE 12

Family 12 members

| Name | $V_H$ Full length sequence |
|---|---|
| 12.1 | SEQ ID NO. 145 |

TABLE 13

Family 13 members

| Name | $V_H$ Full length sequence |
|---|---|
| 13.1 | SEQ ID NO. 146 |

TABLE 14

Family 14 members

| Name | $V_H$ Full length sequence |
|---|---|
| 14.1 | SEQ ID NO. 147 |

TABLE 15

Family 15 members

| Name | $V_H$ Full length sequence |
|---|---|
| 15.1 | SEQ ID NO. 148 |

Thus, in another aspect, the invention relates to a binding molecule comprising a first single $V_H$ domain antibody capable of binding human PSMA with a CDR1, 2 or 3 sequence as shown for any of $V_H$ 1.21 to 1.30 as shown in Table 1a or variant thereof (said variant preferably retaining one of the CDR2 sequences as set out in table 1a) and a second single $V_H$ domain antibody capable of binding human PSMA. In one embodiment, said single first domain $V_H$ domain antibody comprises a sequence selected from SEQ ID NOs 4, 8, 12, 16, 20, 24, 28, 32, 36 or 40.

In one embodiment, the second $V_H$ domain binds to the same epitope, part, domain, subunit or confirmation of PSMA as the first $V_H$ domain. For example, the second $V_H$ domain may be selected from family 1, 5, 6, 12 or 13 or family 1, 5, 6, 12 or 13-like sequence. In one embodiment, the first $V_H$ domain comprises or consists of SEQ ID No: 28.

In one embodiment, the second $V_H$ domain binds to a different epitope, part, domain, subunit or confirmation of PSMA than the first $V_H$ domain. Thus, the molecule is biparatopic. The second $V_H$ domain may be selected from a family 2, 3, 4, 7, 9, 10, 11 or 14 or a family 2, 3, 4, 7, 9, 10, 11 or 14-like sequence. In one embodiment said second $V_H$ domain antibody is selected from Table 2. In one embodiment, the first $V_H$ domain comprises SEQ ID No:28 and the second $V_H$ domain comprises SEQ ID NO:71. In one embodiment said second $V_H$ domain antibody is selected from Table 2.

In one embodiment the first single $V_H$ domain antibody is located C or N terminally. In one embodiment said first and second $V_H$ domain are covalently linked by a peptide. In one embodiment the peptide is between 3 and 50 amino acids long. In one embodiment the linker comprises glycine and serine amino acid residues. In one embodiment the peptide linker consists of the formula $(Gly_4Ser)_n$, where n=from 1 to 10.

Nucleic acids encoding Family members of families 2-15 (i.e. SEQ ID Nos. 149-226) can be used in the constructs for the expression of bivalent binding molecules together with a nucleic acid selected from any of SEQ ID Nos. 61-70.

In another embodiment, the second moiety may comprise a $V_H$ domain or another antibody fragment that is specific for a different antigen to provide a bispecific binding molecule. As used herein, the term "bispecific binding molecule" thus refers to a polypeptide that comprises a binding molecule as described herein which has a binding site that has binding specificity for PSMA, and a second polypeptide domain which has a binding site that has binding specificity for a second target, i.e., the bispecific binding molecule has specificity for two targets. The first target and the second target are not the same, i.e. are different targets, e.g., proteins; both may be present on a cell surface. Accordingly, a bispecific binding molecule as described herein can selectively and specifically bind to a cell that expresses (or displays on its cell surface) the first target and the second target. In another embodiment, the binding molecule comprises more than two antigen-binding moieties.

As used herein, the terms first and second do not designate the orientation of the molecule, that is the first VH may be C or N-terminally located.

In another embodiment, more than two moieties are joined together providing a multispecific binding molecule. A multispecific polypeptide agent as described herein can in addition to binding PSMA bind one or more additional targets, i.e., a multispecific polypeptide can bind at least two, at least three, at least four, at least five, at least six, or more targets, wherein the multispecific polypeptide agent has at least two, at least, at least three, at least four, at least five, at least six, or more target binding sites respectively.

As used herein, the term "target" refers to a biological molecule (e.g., antigen, peptide, polypeptide, protein, lipid, carbohydrate) to which a polypeptide domain which has a binding site can selectively bind. The target can be, for example, an intracellular target (such as an intracellular protein target) or a cell-surface target (such as a membrane protein, e.g., a receptor protein). Preferably, a target is a cell-surface target, such as a cell-surface protein. Preferably, the first cell-surface target and second cell-surface target are both present on a cell. In one embodiment, the target is an immunooncology target.

Multispecific antibodies of the present invention can be constructed using methods known art. If desired, bispecific or multispecific binding molecules can be linked to an antibody Fc region or fragment thereof, comprising one or both of $C_H2$ and $C_H3$ domains, and optionally a hinge region. For example, vectors encoding bispecific or multispecific binding molecules linked as a single nucleotide sequence to an Fc region or fragment thereof can be used to prepare such polypeptides.

In one embodiment, the second moiety may serve to prolong the half-life of the binding molecule. The second moiety may comprise a protein, for example and antibody, or part thereof that binds a serum albumin, e.g., human serum albumin (HSA) or mouse serum albumin (MSA). The second moiety may comprise a $V_H$ domain that binds serum albumin, e.g., human serum albumin (HSA) or mouse serum albumin (MSA).

The second moiety may comprise a serum albumin, e.g. a human serum albumin (HSA) or a variant thereof such as HSA C34S. Further provided is binding molecule as described herein comprising a $V_H$ domain and an Fc domain, e.g., wherein the $V_H$ domain is fused to an Fc domain. Further provided is a binding molecule that comprises a second variable domain that specifically binds a second antigen, where the second antigen is an antigen other than human PSMA. The second antigen may be a cluster of differentiation (CD) molecule or a Major Histocompatibility Complex (MHC) Class II molecule.

In one embodiment, the binding molecule of the invention is labelled with a detectable or functional label. A label can be any molecule that produces or can be induced to produce a signal, including but not limited to fluorescers, radiolabels, enzymes, chemiluminescers, a nuclear magnetic resonance active label or photosensitizers. Thus, the binding may be detected and/or measured by detecting fluorescence or luminescence, radioactivity, enzyme activity or light absorbance.

In still other embodiments, the binding molecule of the invention is coupled to at least one therapeutic moiety, such as a drug, an enzyme or a toxin. In one embodiment, the therapeutic moiety is a toxin, for example a cytotoxic radionuclide, chemical toxin or protein toxin. For example, the PSMA binding molecule of the invention can be coupled to a radioactive isotope such as an α-, β-, or γ-emitter, or a β- and γ-emitter.

The toxin as used in the various aspects and embodiments of the invention may be selected from calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, docetaxel, dolastatin 10, auristatin E and auristatin PHE. In other embodiments, the therapeutic moiety is an immunostimulatory or immunomodulating agent.

In one aspect, the invention thus provides an immunoconjugate comprising a single $V_H$ domain antibody described herein.

In one aspect, the invention relates to an immunoconjugate of the formula A-(L-D)n wherein A is an antigen-binding moiety comprising a first human single heavy chain variable immunoglobulin ($V_H$) domain antibody capable of binding specifically to human PSMA as described herein, optionally comprising a second human single heavy chain variable immunoglobulin ($V_H$) domain antibody capable of binding specifically to human PSMA and optionally comprising a third human single heavy chain variable immunoglobulin ($V_H$) domain antibody, L is a linker, and D is an auristatin or a derivative thereof and n is 1, 2, 3, 4, 5, 6, 7, 8, 9 or 10.

Thus, the single $V_H$ domain antibody comprising a CDR1, CDR2 and CDR3 sequence as described herein can be used in an immunoconjugate as described above. Said single domain $V_H$ domain antibody comprises a sequence selected from SEQ ID NOs 4, 8, 12, 16, 20, 24, 28, 32, 36 or 40. In one embodiment, the sequence is SEQ ID No. 28 and the $V_H$ is $V_H$ 1.27. In one embodiment, said second single domain $V_H$ domain antibody is selected from Family 2.

In one embodiment, D is MMAE, MMAF, or a derivative thereof. In one embodiment, D is MMAE or a derivative thereof conjugated to the antigen-binding moiety via a valine-citrulline (vc) linker (vc-MMAE). In one embodiment, D is MMAF or a derivative thereof conjugated to the antigen-binding moiety via a maleimidocaproyl linker (mc-MMAF). In one embodiment, L-D is vedotin or mafodotin.

The immunoconjugates of the invention are preferably of the formula A-(L-D)n wherein A is an Auristatin or derivative thereof. In one embodiment, D is MMAE, MMAF, or a derivative thereof.

Auristatins are synthetic analogues of the antineoplastic natural product Dolastatin. Auristatins inhibit cell division by blocking the polymerisation of tubulin and are used as toxic payloads in antibody-drug conjugates. The family of auristatins includes monomethyl auristatin E (MMAE) and monomethyl auristatin F (MMAF). In preclinical models, auristatins have been found to be 100- to 1,000-fold more potent than traditionally-used chemotherapeutics.

MMAE & Vedotin

Monomethyl auristatin E (MMAE, desmethyl-auristatin E) is a synthetic antimitotic, antineoplastic agent The IUPAC name for MMAE is (S)—N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide.

Monomethyl auristatin E or MMAE is 100-1000 times more potent than doxorubicin, but its toxicity is such that cannot be used as a drug itself. However, it has been used as part of an antibody-drug conjugate or ADC, wherein MMAE is linked to a monoclonal antibody (mAb) that recognizes a specific marker expressed in cancer cells and directs MMAE to the cancer cell.

As MMAE is toxic, it has been used as a therapeutic only when conjugated to a monoclonal antibody (mAb) to target the MMAE to cancer cells. In the International Nonproprietary Names for MMAE-mAb-conjugates, the name “vedotin” denotes MMAE plus its linking structure to the antibody. The structure linking the targeting mAb to MMAE may comprise an attachment group (maleimide (mal) and caproic acid (cap)), a spacer (paraaminobenzoic acid) and a cathepsin-cleavable linker (amino acids valine (Val) and citrulline (Cit)).

The tether that connects MMAE to the monoclonal antibody is stable in extracellular fluid, but is cleaved by cathepsin once the antibody-drug-conjugate has bound to the targeted cancer cell antigen and entered the cancer cell, after which the ADC releases the toxic MMAE and activates the potent anti-mitotic mechanism. Antibody-drug conjugates enhance the antitumor effects of antibodies and reduce adverse systemic effects of highly potent cytotoxic agents.

MMAF & Mafodotin

Monomethyl auristatin F (MMAF, desmethyl-auristatin F) is a synthetic antineoplastic agent. The IUPAC name for MMAF is (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid.

MMAF is the toxic payload used in some experimental anti-cancer antibody-drug conjugates such as vorsetuzumab mafodotin and SGN-CD19A. In International Nonproprietary Names for MMAF-antibody-conjugates, the name mafodotin refers to MMAF plus its attachment structure to the antibody. The attachment group may consist of maleimide and caproic acid.

Auristatins and their use as components of ADC are reviewed by Maderna and Leverett in “Recent Advances in the Development of New Auristatins: Structural Modifications and Application in Antibody Drug Conjugates”; Mol. Pharmaceutics, 2015, 12 (6), pp 1798-1812 Mendelsohn et al., “Investigation of Hydrophilic Auristatin Derivatives for Use in Antibody Drug Conjugates”. Bioconjugate Chem., Article ASAP DOI: 10.1021/acs.bioconjchem.6b00530, Publication Date (Web): Jan. 6, 2017 describe derivatives of the natural product dolastatin 10 containing pyridines and other basic amines, which were examined to assess more hydrophilic auristatin derivatives would be sufficiently potent for use in ADC. A pyridine derivative, monomethyl auristatin PYE, showed the greatest potency when tested in vivo.

The immunoconjugate, compositions and methods of the invention may feature an auristatin which is either monomethylauristatin E (MMAE) or monomethylauristatin F (MMAF) or a derivative thereof.

MMAE may be conjugated to the antigen-binding moiety via a valine-citrulline (vc) linker (vc-MMAE). MMAF is conjugated to the antigen-binding moiety via a maleimidocaproyl linker (mc-MMAF) using HiPEG™ technology (WO 2009/047500; Cong et al., (2012) Bioconjugate Chem. 2012, 23, 248-263.

Thus, in one embodiment, D is MMAE or a derivative thereof conjugated to the antigen-binding moiety via a valine-citrulline (vc) linker (vc-MMAE). In another embodiment D is MMAF or a derivative thereof conjugated to the antigen-binding moiety via a maleimidocaproyl linker (mc-MMAF). In another embodiment L-D is vedotin or mafodotin. L-D may also comprise one of more H amino acid which links A and L-D.

The immunoconjugate may comprise a further toxic moiety, a label, half life extension or other moiety.

Also within the scope of the invention are methods of treatment comprising administration of said immunoconjugate to a subject in need thereof. Furthermore, the immunoconjugate may be used in the manufacture of the manufacture of a medicament for the treatment of a cancer associated with expression of PSMA, prostate cancer or a prostatic disorder. The invention also relates to immunoconjugate as described above for treatment of a disease as described herein.

Toxin-conjugated forms of the PSMA binding molecules of the present invention preferably mediate specific cell killing of PSMA-expressing cells at picomolar concentrations.

In another aspect, the PSMA binding molecules of the invention are modified to increase half-life, for example by a chemical modification, especially by PEGylation, or by incorporation in a liposome or using a serum albumin protein.

In one embodiment, the binding molecule of the invention is covalently modified. The term "covalently modified/covalent modification" includes modifications of a binding molecule according to the present invention, e.g., of a specified sequence herein; with an organic proteinaceous or non-proteinaceous derivatizing agent, fusions to heterologous polypeptide sequences, and post-translational modifications. Covalent modified polypeptides, e.g., of a specified sequence, still have the functional properties described herein, for example the ability to bind the human PSMA or, Covalent modifications are generally introduced by reacting targeted amino acid residues with an organic derivatizing agent that is capable of reacting with selected side chains or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the [alpha]-amino groups of lysine, arginine, and histidine side chains. Covalent modifications, e.g., include fusion proteins comprising a PSMA binding molecule according to the present invention, e.g., of a specified sequence and their amino acid sequence variants, such as immunoadhesins, and N-terminal fusions to heterologous signal sequences.

The binding molecules of the invention have certain functional properties as further described below. These and other pharmacological activities of the binding molecules of the invention may be demonstrated in standard test methods for example as described in the art.

The binding molecules of the invention can be internalised into a cell along with the prostate-specific membrane antigen. Binding molecules of the invention bind specifically to epitopes on the extracellular domain of human PSMA. In one embodiment, binding molecules of the invention specifically bind PSMA in its dimeric form. Binding molecules of the invention can be conjugated to a toxic moiety and used to ablate or kill PSMA-expressing prostatic or cancerous cells.

Binding molecules of the invention can bind live cells, such as a tumor cell or a prostate cell, such as human PSMA expressing CHO cells, LNCaP cells as shown in the examples (see examples 7b and Tables 18 and 19). In a further aspect, the present invention provides single domain antibodies that bind to PSMA with an EC50 value of between 100 nM and 100 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less, such as less than 500, 400, 300, 200, 100 pM, or even less, such as less than 4 pM, preferably as measured in a FMAT binding assay. In particular, EC50 values are shown in Table 19. In one embodiment, binding molecules of the invention are capable of binding specifically to human PSMA and to cynomolgus monkey PSMA.

Potency is normally expressed as an $IC_{50}$ value, in nM unless otherwise stated. In functional assays, $IC_{50}$ is the concentration of a binding member that reduces a biological response by 50% of its maximum. $IC_{50}$ may be calculated by plotting % of maximal biological response as a function of the log of the binding member concentration, and using a software program to fit a sigmoidal function to the data to generate $IC_{50}$ values. Methods for measuring $IC_{50}$ are well known in the art. For example, to determine the $IC_{50}$, a HIS ZAP Cell Killing assay may be employed to determine $IC_{50}$. $EC_{50}$ designates the half maximal effective concentration.

In another aspect, the invention relates to a binding molecule comprising or consisting of at least one immunoglobulin single domain antibody directed against PSMA, preferably human PSMA, wherein said domain is a human $V_H$ domain and has an $IC_{50}$ of about 0.2 to about 1000 nM or more, for example 0.2 to 900, 0.2 to 800, 0.2 to 700, 0.2 to 600, 0.2 to 500, 0.2 to 400, 0.2 to 300, 0.2 to 200, 0.2 to 100, 0.2 to 50, 0.2 to 40, 0.2 to 30, 0.2 to 20, 0.2 to 10, 0.2 to 9, 0.2 to 8, 0.2 to 7, 0.2 to 6, 0.2 to 5, 0.2 to 4, 0.2 to 3, 0.2 to 2 or 0.2 to 1 when tested as described in the examples.

Additionally, binding kinetics and affinity (expressed as the equilibrium dissociation constant, KD) of PSMA binding molecules of the invention for binding PSMA may be determined, e.g., using surface plasmon resonance such as BIAcore® or Octet, or KD may be estimated from pA2 analysis. In particular, the molecules of the invention are very potent (i.e., EC50 values as measured, e.g., in the experimental part in the pM range).

In a further aspect, the present invention provides a single domain antibody as described herein, wherein said sdAb binds to said PSMA with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less such, as less than 10 pM. Preferably, the KD is determined as shown in the examples (example 8b).

In one embodiment, a binding molecule according to the invention has a binding affinity to PSMA with an affinity constant of at least about $10^7$ $M^{-1}$, preferably about $10^9$ $M^{-1}$, and more preferably, about $10^{10}$ $M^{-1}$ to $10^{11}$ $M^{-1}$ or higher. In one embodiment, a binding molecule according to the invention has a Kon of 1.00E+04 to 1.00E+6 (1/Ms). In one embodiment, a binding molecule according to the invention has Koff of 1.00E−03 to 1.00E−05 (1/s).

Binding molecules of the invention have shown excellent stability, including heat and serum stability (see examples). Furthermore, binding molecules of the invention show rapid tumor targeting as shown in the examples. Furthermore, binding molecules of the invention also show high specificity for human PSMA and low uptake in non-target tissues (see examples).

In one embodiment, binding molecules of the invention show fast blood clearance. In one embodiment, binding molecules of the invention show low renal retention. In one embodiment, binding molecules can inhibit, e.g., competitively inhibit, the binding of another antibody e.g., J591, to human PSMA.

In one embodiment, the binding molecule of the invention as defined herein may have one or more property select from the following non-limiting list:

a) high-affinity binding to human and/or cynomolgus prostate-specific membrane antigen in its native form occurring on the surface of tumor cells,
b) internalization by a tumor cell,
c) low uptake in non-target tissues,
d) rapid tumor targeting,
e) binding strongly to LNCaP cells, but not or only minimally to cells which lack expression of prostate-specific membrane antigen and/or
f) binding to a unique epitope on PSMA.

Methods for preparing or generating the polypeptides, nucleic acids, host cells, products and compositions described herein using in vitro expression libraries can comprise the steps of:
a) providing a set, collection or library of nucleic acid sequences encoding amino acid sequences; and
b) screening said set, collection or library for amino acid sequences that can bind to/have affinity for PSMA and
c) isolating the amino acid sequence(s) that can bind to/have affinity for PSMA.

In the above methods, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art (see for example Phage Display of Peptides and Proteins: A Laboratory Manual, Academic Press; 1st edition (Oct. 28, 1996) Brian K. Kay, Jill Winter, John McCafferty).

A binding molecule described herein, including heavy chain antibody with a $V_H$ domain, can be expressed in a transgenic rodent, for example a mouse. The transgenic rodent, for example a mouse, may have a reduced capacity to express endogenous antibody genes. Thus, in one embodiment, the rodent has a reduced capacity to express endogenous light and/or heavy chain antibody genes. The rodent may therefore comprise modifications to disrupt expression of endogenous light and/or heavy chain antibody genes so that no functional light and/or heavy chains are produced.

In another aspect of the present invention, there is provided a pharmaceutical composition comprising a PSMA binding molecule according to the present invention and optionally a pharmaceutically acceptable carrier. The binding molecule of the present invention or compositions can be administered by any convenient route. The compounds may be administered by any route, including oral and parenteral administration. Parenteral administration includes, for example, intravenous, intramuscular, intraarterial, intraperitoneal, intranasal, rectal, intravesical, intradermal, topical or subcutaneous administration. Compositions can take the form of one or more dosage units.

The composition of the invention can be in the form of a liquid, e.g., a solution, emulsion or suspension. The liquid can be useful for delivery by injection, infusion (e.g., IV infusion) or sub-cutaneously. The liquid compositions of the invention, whether they are solutions, suspensions or other like form, can also include one or more of the following: sterile diluents such as water, saline solution, preferably physiological saline, Ringer's solution, isotonic sodium chloride, fixed oils such as synthetic mono or diglycerides, polyethylene glycols, glycerin, or other solvents; antibacterial agents such as benzyl alcohol or methyl paraben; and agents for the adjustment of tonicity such as sodium chloride or dextrose. A composition can be enclosed in an ampoule, a disposable syringe or a multiple-dose vial made of glass, plastic or other material.

In specific embodiments, it can be desirable to administer one or more binding molecule of the present invention or compositions locally to the area in need of treatment, or by intravenous injection or infusion.

The amount of the binding molecule of the present invention that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions of the invention comprise an effective amount of a binding molecule of the present invention such that a suitable dosage will be obtained. The correct dosage of the compounds will vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Typically, this amount is at least about 0.01% of a binding molecule of the present invention by weight of the composition.

Preferred compositions of the present invention are prepared so that a parenteral dosage unit contains from about 0.01% to about 2% by weight of the binding molecule of the present invention.

For intravenous administration, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight.

The present compositions can take the form of suitable carriers, such aerosols, sprays, suspensions, or any other form suitable for use. Other examples of suitable pharmaceutical carriers are described in "Remington's Pharmaceutical Sciences" by E. W. Martin.

The pharmaceutical compositions can be prepared using methodology well known in the pharmaceutical art. For example, a composition intended to be administered by injection can be prepared by combining a binding molecule of the present invention with water so as to form a solution. A surfactant can be added to facilitate the formation of a homogeneous solution or suspension.

The invention furthermore relates to a method for the prevention and/or treatment of cancer, in particular prostate cancer, comprising administering a binding molecule of the invention to a patient, said method comprising administering, to a subject in need thereof, a pharmaceutically active amount of a binding molecule and/or of a pharmaceutical composition of the invention. In particular, the invention relates to a method for the prevention and/or treatment of cancer, in particular prostate cancer, said method comprising administering, to a subject in need thereof, a pharmaceutically active amount of a binding molecule or a pharmaceutical composition of the invention.

The invention also relates to a binding molecule of the invention for use in the treatment of disease. The invention also relates to a binding molecule of the invention for use in the treatment of cancer, in particular prostate cancer or a prostatic disorder. "Prostate cancer" refers to all stages and all forms of cancer arising from the tissue of the prostate gland. The invention also relates to the treatment of a disease characterized by aberrant expression of PSMA.

In another aspect, the invention relates to the use of a binding molecule of the invention in the treatment of disease. In another aspect, the invention relates to the use of a binding molecule of the invention in the manufacture of a medicament for the treatment of cancer, in particular prostate cancer or a prostatic disorder.

The binding molecules of the invention are also useful for the treatment, prevention, or amelioration of cancer, in particular prostate cancer or a prostatic disorder. A prostatic disorder refers to any disease that afflicts the prostate gland in the male reproductive system. The prostate gland is dependent on the hormonal secretions of the testes. Expression of PSMA has been detected in other cancers, more specifically in the neovasculature associated with these cancers. A wide range of carcinomas, including conventional (clear cell) renal cell, transitional cell of the bladder, testicular-embryonal, neuroendocrine, colon, and breast, and the different types of malignancies were found consistently and strongly to express PSMA in their neovasculature.

The binding molecule of the invention may be administered as the sole active ingredient or in combination with one or more other therapeutic and/or cytotoxic moiety. In one embodiment, the binding molecule may be conjugated to a toxic moiety.

In therapies of prostatic disorders, e.g., prostate cancer, the anti-PSMA binding molecule can be used in combination with existing therapies. In one embodiment, the single domain antibody is used in combination with an existing therapy or therapeutic agent, for example an anti-cancer therapy. Thus, in another aspect, the invention also relates to a combination therapy comprising administration of a single domain antibody or pharmaceutical composition of the invention and an anti-cancer therapy. The anti-cancer therapy may include a therapeutic agent or radiation therapy and includes gene therapy, viral therapy, RNA therapy bone marrow transplantation, nanotherapy, targeted anti-cancer therapies or oncolytic drugs. Examples of other therapeutic agents include other checkpoint inhibitors, antineoplastic agents, immunogenic agents, attenuated cancerous cells, tumor antigens, antigen presenting cells such as dendritic cells pulsed with tumor-derived antigen or nucleic acids, immune stimulating cytokines (e.g., IL-2, IFNa2, GM-CSF), targeted small molecules and biological molecules (such as components of signal transduction pathways, e.g. modulators of tyrosine kinases and inhibitors of receptor tyrosine kinases, and agents that bind to tumor-specific antigens, including EGFR antagonists), an anti-inflammatory agent, a cytotoxic agent, a radiotoxic agent, or an immunosuppressive agent and cells transfected with a gene encoding an immune stimulating cytokine (e.g., GM-CSF), chemotherapy. In one embodiment, the single domain antibody is used in combination with surgery. The binding molecule of the invention may be administered at the same time or at a different time as the other therapy, e.g., simultaneously, separately or sequentially.

In another aspect, the invention provides a kit for detecting prostate cancer for diagnosis, treatment, prognosis or monitoring comprising a binding molecule of the invention. The kit may also comprise instructions for use. The kits may include a labeled binding molecule of the invention as described above and one or more compounds for detecting the label. The invention in another aspect provides a binding molecule of the invention packaged in lyophilized form, or packaged in an aqueous medium.

The invention also relates to detection methods using the binding molecule of the invention. Given their ability to bind to human PSMA, the human-PSMA-binding molecules, disclosed herein can be used to detect PSMA (e.g., in a biological sample, such as serum or plasma), using a conventional immunoassay, such as an enzyme linked immunosorbent assays (ELISA), an radioimmunoassay (RIA) or tissue immunohistochemistry. In particular, the invention also relates to in vitro or in vivo methods for diagnosing or monitoring progression of a cancer, in particular prostate cancer. In vitro methods comprise detecting the presence of a PSMA protein in a test sample and comparing this with control sample from a normal subject or with a standard value or standard value range for a normal subject. The sample may be selected from blood, plasma, serum, semen, urine or a tissue biopsy.

The method may include: (a) contacting the sample (and optionally, a reference, e.g., a positive and/or negative control sample) with a PSMA binding molecule of the invention and (b) detecting either the binding molecule bound to PSMA or unbound binding molecule in the sample, to thereby detect PSMA in the biological sample. The binding molecule can be directly or indirectly labeled with a detectable substance to facilitate detection of the bound or unbound antibody. Suitable detectable substances include various enzymes, prosthetic groups, fluorescent materials, luminescent materials and radioactive materials.

In vivo methods may comprise detecting the presence of PSMA in vivo, for example by imaging in a subject. In this method, a PSMA binding molecule of the invention is labeled to detect binding.

As an alternative to labeling the binding molecule of the invention, human PSMA can be assayed in biological fluids by a competition immunoassay utilizing PSMA standards labeled with a detectable substance and an unlabeled human PSMA binding molecule. In this assay, the biological sample, the labeled PSMA standards and the human PSMA binding molecule are combined and the amount of labeled PSMA standard bound to the unlabeled binding molecule is determined. The amount of human PSMA in the biological sample is inversely proportional to the amount of labeled PSMA standard bound to the PSMA binding molecule. Similarly, human PSMA can also be assayed in biological fluids by a competition immunoassay utilizing PSMA standards labeled with a detectable substance and an unlabeled human PSMA binding molecule.

Binding molecules disclosed herein can be used to inhibit PSMA activity, e.g., in a cell culture containing PSMA, in human subjects or in other mammalian subjects having PSMA with which a binding molecule disclosed herein cross-reacts. In one embodiment, a method for inhibiting or increasing PSMA activity is provided comprising contacting PSMA with a binding molecule disclosed herein such that PSMA activity is inhibited or increased. For example, in a cell culture containing, or suspected of containing PSMA, a binding molecule disclosed herein can be added to the culture medium to inhibit PSMA activity in the culture.

Therefore, in one embodiment, the invention also relates to a method of ablating or killing a cell that expresses PSMA, e.g., a cancerous or non-cancerous prostatic cell. Methods of the invention include contacting the cell, with PSMA binding molecule of the invention, in an amount sufficient to ablate or kill, the cell. The methods can be used on cells in culture, e.g., in vitro or ex vivo.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including references to gene accession numbers.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

Sequence Listing

The instant application contains a Sequence Listing which has been filed electronically in ASCII format and is hereby incorporated by reference in its entirety.

The invention is further described in the non-limiting examples.

EXAMPLES

Example 1. Construction of Tg/TKO Mice

Mice carrying a heavy-chain antibody transgenic locus in germline configuration within a background that is silenced for endogenous heavy and light chain antibody expression (triple knock-out, or TKO) were created as previously described (WO2004/076618 and WO2003/000737, Ren et al., Genomics, 84, 686, 2004; Zou et al., J. Immunol., 170, 1354, 2003, WO2016/062990). Briefly, transgenic mice were derived following pronuclear microinjection of freshly fertilised oocytes with a yeast artificial chromosome (YAC) comprising a plethora of human $V_H$, D and J genes in combination with mouse immunoglobulin constant region genes lacking $C_H1$ domains, mouse enhancer and regulatory regions.

Example 2. Antigen for Immunisation

The immunisations used recombinant purified protein or Human Cell Line LNCap. Recombinant human PMSA was purchased from R&D, (cat. no. 4234-ZN), while the LNCap cells were from Sigma Aldrich (cat. no. 89110211-1VL).

Example 3. Immunisation Protocol

Briefly, Tg/TKO mice aged 8-12 weeks of age each received a total of 50 µg of recombinant purified human PSMA protein, emulsified in Complete Freund's Adjuvant and delivered subcutaneously, or 10 million LNCap cells in PBS delivered intraperitoneally, followed by boosts of 1-10 µg of the recombinant protein, emulsified in Incomplete Freund's Adjuvant, also administered subcutaneously, given at various intervals following the initial priming. A final dose of the recombinant purified human PSMA protein antigen was administered intraperitoneally, in phosphate buffered saline, in the absence of adjuvant. Alternative immunisation routes and procedures can also be employed. For example, different adjuvants or immune potentiating procedures may be used instead of Freund's adjuvant. DNA immunisations are often delivered intramuscularly or via a Genegun. Transfected cells or membrane preparations from such cells are often, although not exclusively, administered intraperitoneally.

Example 4. Serum ELISA

During and following immunisation, serum was collected from mice and checked for the presence of heavy-chain antibody responses to the immunogen by ELISA. Nunc Maxisorp plates (Nunc cat. no. 443404) were coated overnight at 4° C. with 50 µl/well of a 1 µg recombinant antigen/ml of PBS solution. Following decanting of the antigen solution, plates were washed using PBS (prepared from PBS Tablets, Oxoid cat. no. BR0014G) supplemented with 0.05% (v/v) Tween® 20 (Sigma P1379), followed by washes with PBS without added Tween 20. To block non-specific protein interactions, a solution of 3% (w/v) skimmed milk powder (Marvel®) in PBS was added to the wells and the plate was incubated for at least one hour at room temperature. Dilutions of serum in 3% Marvel™/PBS were prepared in polypropylene tubes or plates and incubated for at least one hour at room temperature prior to transfer to the blocked ELISA plate where a further incubation of at least one hour took place. Unbound protein was then washed away using repetitive washes with PBS/Tween 20 followed by PBS. A solution of biotin-conjugated, goat anti-mouse IgG, Fcgamma subclass 1 specific antibody (Jackson cat. no. 115-065-205), prepared in PBS/3% Marvel was then added to each well and a further incubation at room temperature for at least one hour took place. Unbound detection antibody was removed by repeated washing using PBS/Tween 20 and PBS. Neutravidin-HRP solution (Pierce cat. no. 31030) in 3% Marvel/PBS was then added to the ELISA plates and allowed to bind for at least 30 minutes. Following further washing, the ELISA was developed using TMB substrate (Sigma cat. no. T0440) and the reaction was stopped after 10 minutes by the addition of 0.5M $H_2SO_4$ solution (Sigma cat. no. 320501). Absorbances were determined by reading at an optical density of 450 nm. Alternative assays, such as ELISPOT assays, may also be used to check for immunisation induced heavy-chain antibody responses.

Example 5. Generation of Libraries from Immunised Mice a) Processing Tissues, RNA Extraction and cDNA Manufacture Spleen, inguinal and brachial lymph nodes were collected into RNAlate® from each immunised animal. For each animal, ½ of the spleen and 4 lymph nodes were processed separately. Initially, the tissues were homogenised; following transfer of tissues to Lysing matrix D bead tubes (MP Bio. Cat. no. 116983001), 600 µl of RLT buffer containing p-mercaptoethanol (from Qiagen RNeas® kit cat. no. 74104) was added before homogenisation in a MP Bio Fastprep96 homogeniser (cat #116010500) at 1600 rpm for 60 seconds. The tubes containing the homogenised tissues were transferred to ice and debris was pelleted by centrifugation at 1200 rpm for 5 minutes. A 400 μl sample of the supernatant was removed and used for RT-PCR. Initially, RNA was extracted using Qiagen RNeasy® kit (cat. no. 74104) following the manufacturer's protocol. Each RNA sample was then used to make cDNA using Superscript III RT-PCR high-fidelity kit (Invitrogen cat. no. 12574-035). For each spleen and lymphnodes RNA sample, 5 RT-PCR reactions were performed, each with $V_H$_J/F (long) primer in combination with a primer for $V_H1$, $V_H2$, $V_H3$, $V_H4$ or $V_H6$ family. Details of the primers are below.

TABLE 16

| Primers for V10: | |
|---|---|
| V1a/pelB(long) | **GCCGCTGGATTGTTATTACTCGCGGCCCAGCCGGCCATGGCC**CAGGTBCA GCTGGTGCAGTCTGGGGCTGAGG SEQ ID No. 227 |
| V2/pelB(long) | **GCCGCTGGATTGTTATTACTCGCGGCCCAGCCGGCCATGGCC**AGATCAC CTTGAAGGAGTCTGG SEQ ID No. 228 |
| V3/pelB(long) | **GCCGCTGGATTGTTATTACTCGCGGCCCAGCCGGCCATGGCC**SAGGTGCA GCTGGTGGAGTCTGGGGGAGG SEQ ID No. 229 |
| V4-4/pelB(long) | **GCCGCTGGATTGTTATTACTCGCGGCCCAGCCGGCCATGGCC**CAGGTGC AGCTGCAGGAGTCGGG SEQ ID No. 230 |
| V6/pelB(long) | **GCCGCTGGATTGTTATTACTCGCGGCCCAGCCGGCCATGGCC**CAGGTACA GCTGCAGCAGTCAGG SEQ ID No. 231 |
| VH_J/F(long) | **CCGTGGTGATGGTGGTGATGGCTACCGCCACCCTCGAGT**GARGAGACRG TGACC SEQ ID No. 232 |

Residues in bold have homology with pUCG3

TABLE 17

| Primers for V23 | |
|---|---|
| VH1-2 (long) | **GCCGCTGGATTGTTATTACTCGCGGCCCAGCCGGCCATGGCC** CAGGTGCAGCTGGTGCAGTCTGGGGCTGAGG SEQ ID No. 233 |
| VH1-3 (long) | **GCCGCTGGATTGTTATTACTCGCGGCCCAGCCGGCCATGGCC** CAGGTCCAGCTCGTGCAGTCTGGGGCTGAGG SEQ ID No. 234 |
| VH1-18 (long) | **GCCGCTGGATTGTTATTACTCGCGGCCCAGCCGGCCATGGCC** CAGGTTCAGCTGGTGCAGTCTGGAGCTGAGG SEQ ID No. 235 |
| VH1-24 (long) | **GCCGCTGGATTGTTATTACTCGCGGCCCAGCCGGCCATGGCC** CAGGTCCAGCTGGTACAGTCTGGGGCTGAGG SEQ ID No. 236 |
| VH2 (long) | **GCCGCTGGATTGTTATTACTCGCGGCCCAGCCGGCCATGGCC** CAGRTCACCTTGAAGGAGTCTGG SEQ ID No. 237 |
| VH3-7 (long) | **GCCGCTGGATTGTTATTACTCGCGGCCCAGCCGGCCATGGCC** GAGGTGCAGCTGGTGGAGTCTGGGGGAGG SEQ ID No. 238 |
| VH3-9 (long) | **GCCGCTGGATTGTTATTACTCGCGGCCCAGCCGGCCATGGCC** GAAGTGCAGCTGGTGGAGTCTGGGGGAGG SEQ ID No. 239 |
| VH3-11 (long) | **GCCGCTGGATTGTTATTACTCGCGGCCCAGCCGGCCATGGCC** CAGGTGCAGCTGGTGGAGTCTGGGGGAGG SEQ ID No. 240 |
| VH3-23 (long) | **GCCGCTGGATTGTTATTACTCGCGGCCCAGCCGGCCATGGCC** GAGGTGCAGCTGTTGGAGTCTGGGGGAGG SEQ ID No. 241 |
| VH3-23 (long) | **GCCGCTGGATTGTTATTACTCGCGGCCCAGCCGGCCATGGCC** GAGGTGCAGCTGTTGGAGTCTGGGGGAGG SEQ ID No. 242 |
| VH4-4 (long) | **GCCGCTGGATTGTTATTACTCGCGGCCCAGCCGGCCATGGCC** CAGGTGCAGCTGCAGGAGTCGGG SEQ ID No. 243 |
| VH4-34 (long) | **GCCGCTGGATTGTTATTACTCGCGGCCCAGCCGGCCATGGCC** CAGGTGCAGCTACAGCAGTGGGGC SEQ ID No. 244 |
| VH6-1 (long) | **GCCGCTGGATTGTTATTACTCGCGGCCCAGCCGGCCATGGCC** CAGGTACAGCTGCAGCAGTCAGG SEQ ID No. 245 |
| VH_J/F (long) | **CCGTGGTGATGGTGGTGATGGCTACCGCCACCCTCGAGT**GAR GAGACRGTGACC SEQ ID No. 246 |

Residues in bold have homology with pUCG3

The code for the choice of nucleotide for degenerate primer is: R: A, G. Y: C, T. M: A, C. K: G, T. S: C, G. W: A, T. B: C, G, T. V: A, C, G. D: A, G, T. N: A, C, G, T Mastermixes were prepared for the RT-PCR reactions. Products in the range of 370 bp were confirmed by gel electrophoresis.

a) Cloning into Phagemid Vector

The phagemid vector, pUCG3, was employed in these studies. A PCR-based method was used to construct the $V_H$ phagemid libraries from the amplified $V_H$ sequences. The following procedure was used: A linearised version of pUCG3 was created using PCR; with the following primers: pUCG3-pHENAPmut4 SEQ ID No. 247 pUCG3-pHENAPmut5mycHis SEQ ID No. 248

Phusion High fidelity PCR master mix with GC buffer (cat. no. F532L, NEB) was used for the PCR reactions. The PCR product (3152 bp) was gel purified using Fermentas GeneJet Gel purification kit (cat. no. K0691), according to the manufacturer's instructions, with final elution in 40 μl of elution buffer. The purified $V_H$ RT-PCR products were employed as megaprimers with the linearised pUCG3 to give phagemid products for transformation and library creation.

Example 6. Selection Strategies for Isolation of PSMA Binders

Preparation of library phage stocks and phage display selections were performed according to published methods (Antibody Engineering, edited by Benny Lo, chapter 8, p 161-176, 2004). In most cases, phage display combined with a panning approach was used to isolate binding $V_H$ domains. However, a variety of different selection methods are well described in the art, including soluble selection and selections performed under stress (e.g. heat). Selections to promote internalising anti-PSMA $V_H$ were also conducted with monovalent and multivalent phage (patent US2009170792 (A1)—2009 Jul. 2). Briefly, blocked phage in ice-cold cell media were added to 4 ml ice-cold cell media containing $2.5\times10^6$ LnCAP cells. Phage and cells were incubated on ice for 2 hours, mixing occasionally to prevent cell clumping. Unbound or weakly bound phage were removed by washing five times in ice-cold PBS. The phage were then allowed to internalise by incubating the cells in media at 37° C. before removing phage bound to the outside of the cells with a 5 minutes wash step in a low pH cell-stripping buffer at 4° C. The cells were then lysed to harvest internalised phage using trimethylamine. Both the stripped and internalised fractions were neutralised with Tris buffer before being used to infect *E. coli*. The phage outputs were analysed as described for panning selections on recombinant proteins.

Example 7. Assays for Target Binding $V_H$ from the different selections were screened in one or more of the following assays to identify specific $V_H$ capable of binding PMSA.

a) Binding ELISA

Following selections of the libraries, specific $V_H$ antibodies were identified by phage ELISA following published methods (Antibody Engineering, edited by Benny Lo, chapter 8, p 161-176, 2004). Phage ELISAs were performed against target protein and an unrelated antigen as control. In some cases, purified or crude extracts of $V_H$ domains were assayed by ELISA instead of using a phage ELISA. In these cases, bacterial periplasmic extracts or purified $V_H$ were used.

b) FMAT Direct cell Binding Assay

Periplasmic extracts from *E. coli* were screened for production of PSMA-binding-His-tagged $V_H$ using Fluorescence Microvolume Assay Technology (FMAT), a fluorescence-based platform that detects fluorescence localized to beads or cells settled at the bottom of microwells (Dietz et al., *Cytometry* 23:177-186 (1996), Miraglia et al., *J. Biomol. Screening* 4:193-204 (1999). CHO TREX human and cynomolgus cell lines were generated in-house using full-length human and cynomolgus PSMA using standard procedures. LnCAP cells were purchased from Sigma Aldrich.

Figure 1B:
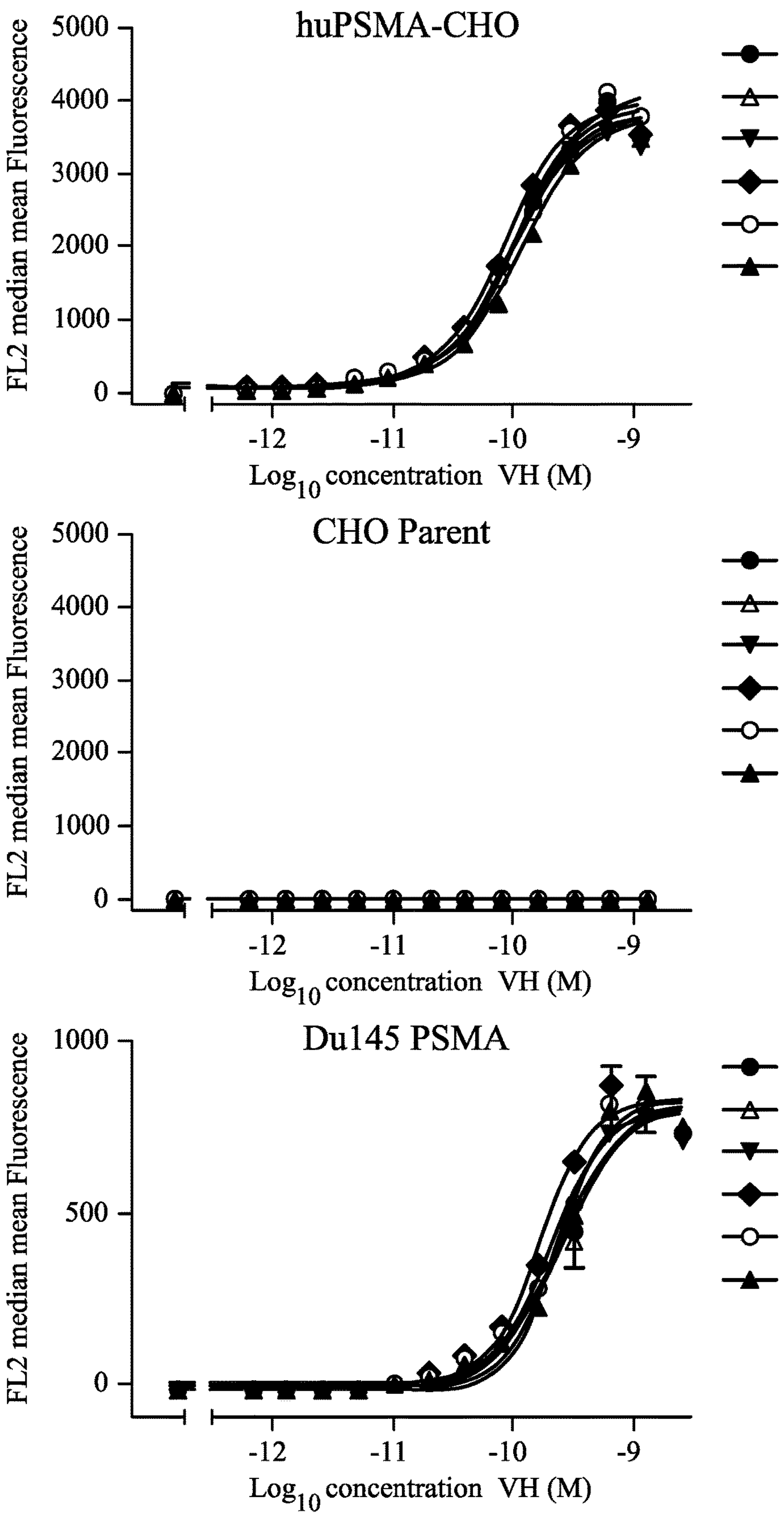
Figure 1B:
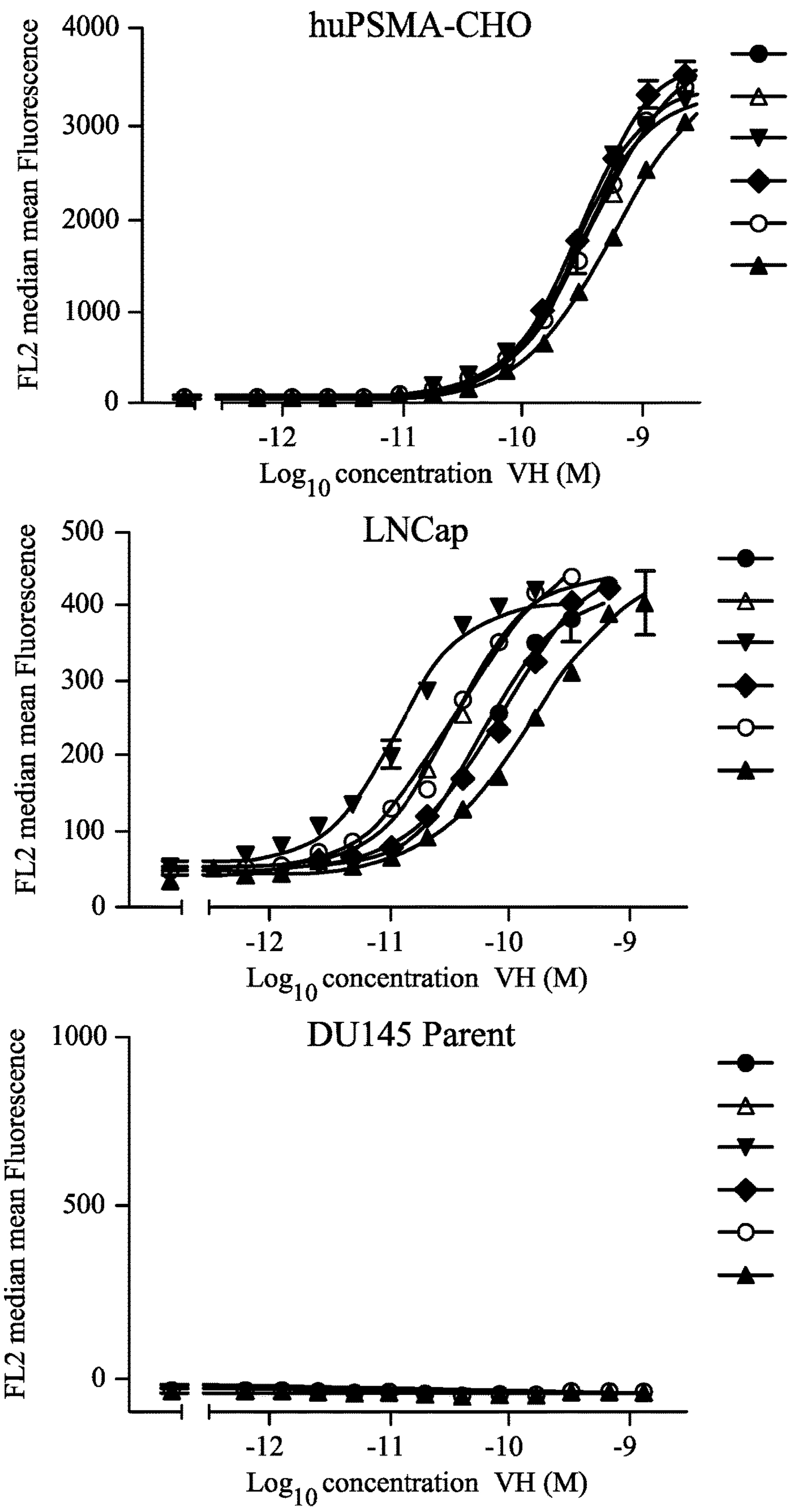
Figure 1C:
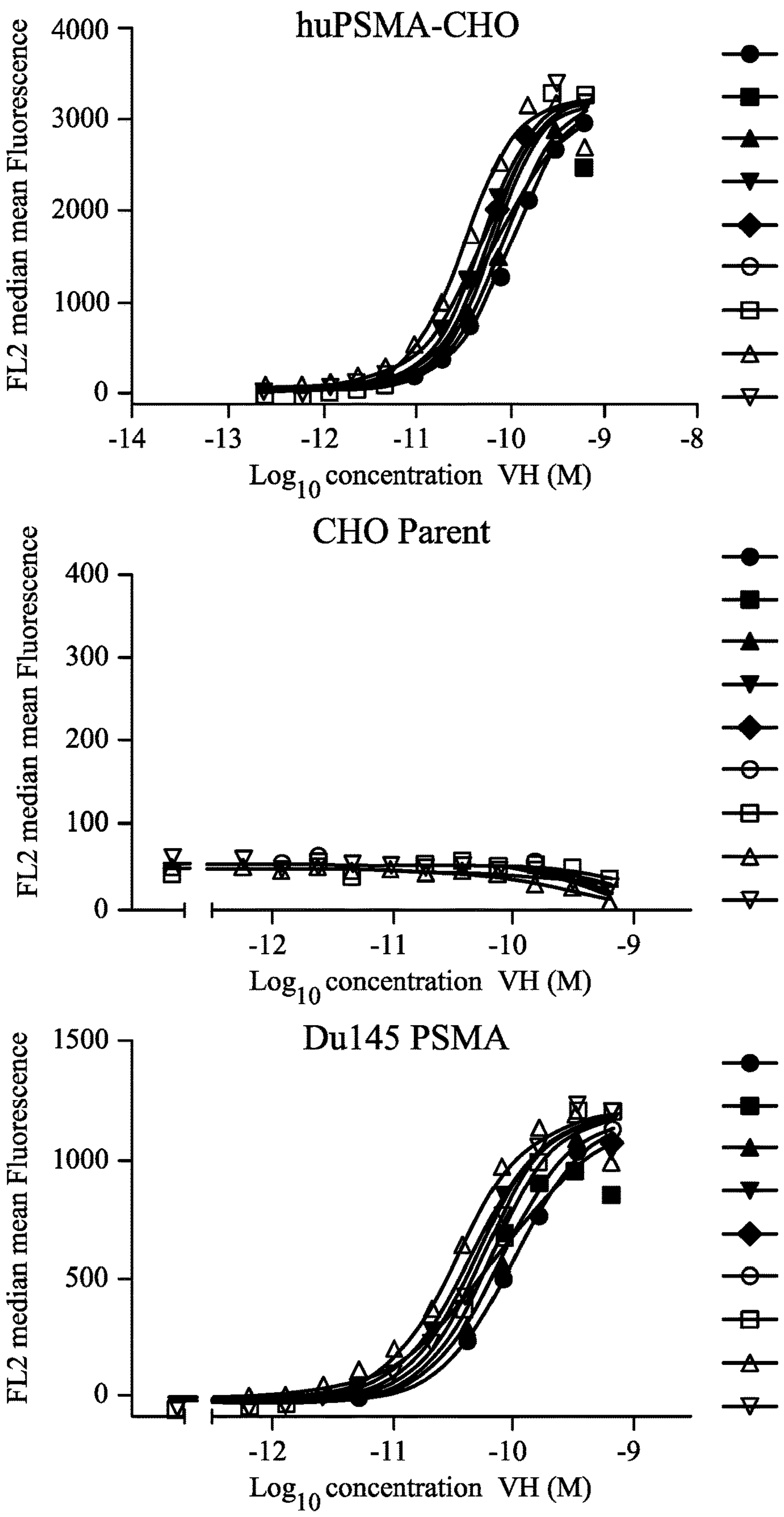
Figure 1C:
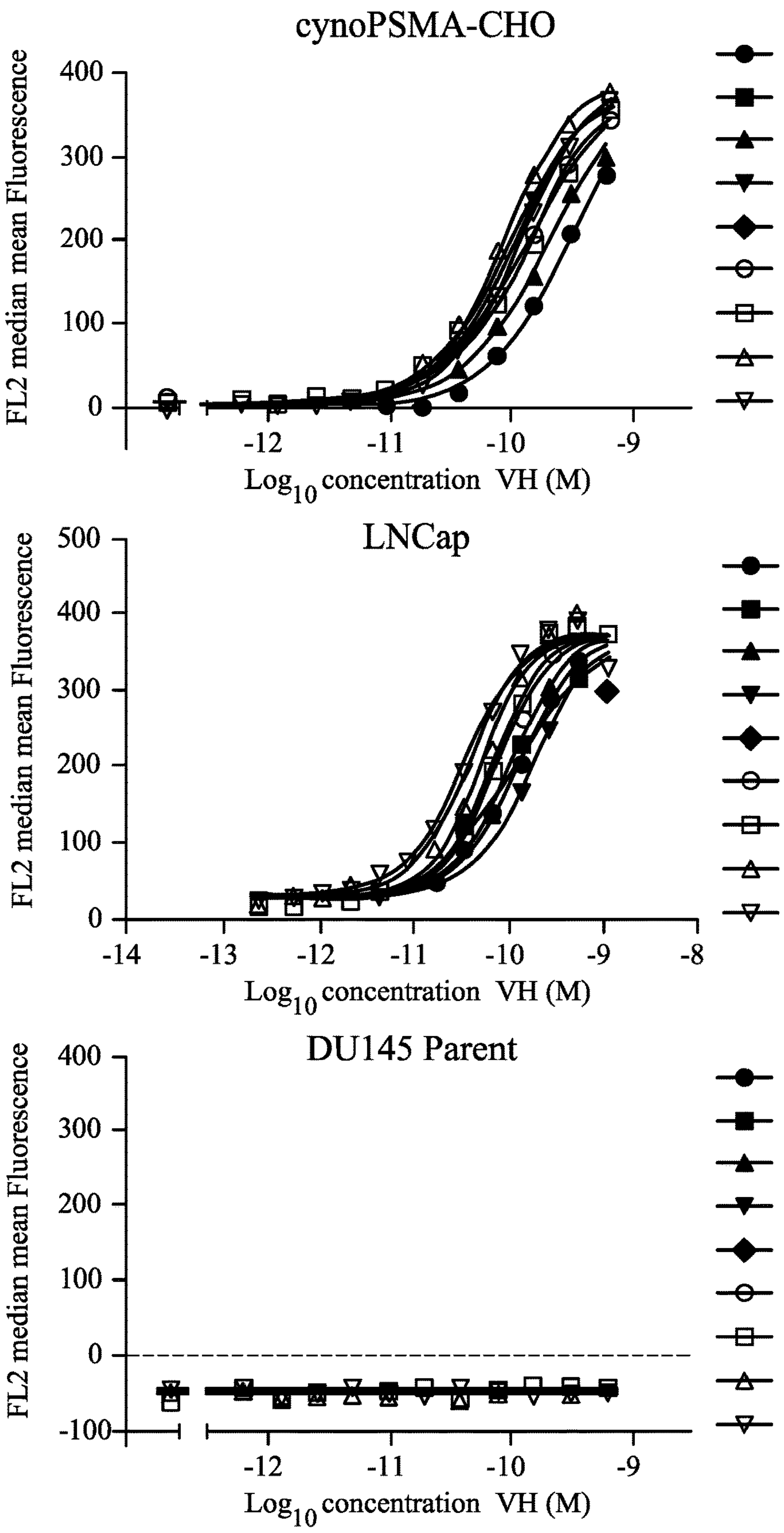

Peripreps were tested by single point screening for the presence of $V_H$ that bound specifically to CHO human PSMA, CHO cyno PSMA and LnCAP cells with no binding to CHO parental cells in an FMAT Direct Binding Assay. For titrations, $V_H$ purified via the terminal His tag were serially diluted in FMAT assay buffer then binding was measured as described above (FIG. 1). Improved variants show similar properties to the parent $V_H$ (FIGS. 1*b* and 1*c*).

TABLE 18

EC50 values for anti-PSMA $V_H$ binding to PSMA expressing cell lines. Values are in the picomolar range (prepared from purified $V_H$)

a)

| EC50 | huPSMA CHO (M) | cynoPSMA CHO (M) | DU145 PSMA (M) | LNCap (M) |
|---|---|---|---|---|
| 2.1 | 1.097E−10 | 3.667E−10 | 2.304E−10 | 6.07E−11 |
| 2.18 | 1.044E−10 | 3.370E−10 | 2.496E−10 | 3.54E−11 |
| 2.17 | 1.004E−10 | 3.082E−10 | 2.181E−10 | 1.13E−11 |
| 2.15 | 9.212E−11 | 3.335E−10 | 1.663E−10 | 8.41E−11 |
| 2.14 | 1.103E−10 | 4.269E−10 | 2.023E−10 | 3.32E−11 |
| 2.22 | 1.232E−10 | 6.129E−10 | 2.293E−10 | 1.53E−10 |
| 1.8 | 1.029E−10 | 3.099E−10 | 9.455E−11 | 1.473E−10 |
| 1.10 | 7.182E−11 | 1.518E−10 | 6.699E−11 | 1.328E−10 |
| 1.11 | 8.634E−11 | 2.168E−10 | 7.604E−11 | 1.189E−10 |
| 1.12 | 5.023E−11 | 1.097E−10 | 4.15E−11 | 1.992E−10 |
| 1.13 | 5.127E−11 | 1.154E−10 | 4.564E−11 | 3.862E−11 |
| 1.14 | 5.884E−11 | 1.45E−10 | 5.201E−11 | 8.329E−11 |
| 1.16 | 6.805E−11 | 1.458E−10 | 5.938E−11 | 7.539E−11 |
| 1.17 | 3.338E−11 | 9.127E−11 | 3.099E−11 | 5.853E−11 |
| 1.18 | 5.858E−11 | 1.237E−10 | 4.949E−11 | 4.239E−11 |

b) $EC_{50}$ values for anti-PSMA $V_H$ binding to human PSMA-CHO. The linker length used was 6GS (i.e. $(G_4S)_6$).

| No | Construct | EC50 |
|---|---|---|
| 1 | 1.1-2.1 | 3.616E−10 |
| 2 | 1.1-2.17 | 2.639E−10 |
| 3 | 1.1-2.15 | 1.948E−10 |
| 4 | 1.1-2.22 | 1.784E−10 |
| 5 | 1.16-2.1 | 3.057E−10 |
| 6 | 1.16-2.17 | 3.327E−10 |
| 7 | 1.16-2.15 | 1.967E−10 |
| 8 | 1.16-2.22 | 2.250E−10 |
| 9 | 1.11-2.1 | 2.871E−10 |
| 10 | 1.11-2.17 | 2.805E−10 |
| 11 | 1.11-2.15 | 2.100E−10 |
| 12 | 1.11-2.22 | 2.187E−10 |
| 13 | 1.18-2.1 | 2.938E−10 |
| 14 | 1.18-2.17 | 2.778E−10 |
| 15 | 1.18-2.15 | 1.921E−10 |
| 16 | 1.18-2.22 | 1.958E−10 |
| 17 | 1.17-2.1 | 3.252E−10 |
| 18 | 1.17-2.15 | 2.986E−10 |
| 19 | 1.17-2.17 | 1.921E−10 |
| 20 | 1.17-2.22 | 1.989E−10 |

Sequencing

Each individual $V_H$ clone as identified above was sequenced from the phagemid and grouped based on $V_H$ germline and CDR3 amino acid similarity into separate families. Representative clones were further characterised. Variants, including germlined variants, were generated by standard methods of parent clones e.g. 1.1 or 2.1. Table 1 shows the sequences of clones family in family 1. Clones 1.8-1.30 are variants of 1.1. Clones 1.21 to 1.30 are improved sequence optimised variants with liability corrections in the CDR2 sequence.

Example 8—Characterisation of $V_H$ a) Specificity of anti-PMSA

The specificity of individual $V_H$ for target antigen was confirmed by ELISA, following the methods described in Example 7(a). $V_H$ were tested for binding to PMSA and shown not to cross react with irrelevant proteins.

b) Measurement of Binding Kinetics Using Octet

Binding kinetics of purified anti-PSMA $V_H$ antibodies were measured on a ForteBio Octet RED 384 instrument. Recombinant PMSA was diluted to 20 μg/ml in sodium acetate buffer, pH 5 (ForteBio, cat. no. 18-1069) and coupled to ARG2G biosensors (ForteBio cat. no. 18-5092) using amine-coupling chemistry (NHS-EDC amine-coupling, ForteBio cat. nos. 18-1067 and 18-1033), followed by quenching in ethanolamine (ForteBio cat. no. 18-1071). Binding kinetics of anti-PSMA $V_H$ antibodies were then determined by preparing each $V_H$ antibody in dilution series (typically 1:2 dilution series starting with 15 μg/ml, $V_H$ at the highest concentration), and then measuring binding of the different $V_H$ concentrations to the PSMA– coupled biosensors. $V_H$ binding kinetics were then determined from the (blank subtracted) sensorgram trace using 1:1 binding models and ForteBio Octet DataAnalysis software. Binding affinities from 1-150 nM and in the subnanomolar range were detected and examples of the Octet profiles are shown in FIG. 2 and in the binding parameters thereof in Table 19 below.

TABLE 19

| | KD (nM) | Kdis (1/s) |
|---|---|---|
| 2.1 | 1.64 | 4.56E−04 |
| 1.1 | 2.44 | 1.54E−03 |
| 3.1 | 3.78 | 4.52E−04 |

Further family members in particular variants of parent molecules were also tested as below using 1:2 dilution series starting with 0.375 μg/ml. Binding affinities from in the low nanomolar to picomolar range were detected as shown in Tables 20 and 21.

TABLE 20

| Clone | KD (nM) | Kdis (1/s) |
|---|---|---|
| 1.8 | 1.95 | 1.04E−03 |
| 1.10 | 0.67 | 4.18E−04 |
| 1.11 | 0.80 | 4.95E−04 |
| 1.12 | 0.55 | 4.28E−04 |
| 1.14 | 0.46 | 3.35E−04 |
| 1.16 | 0.44 | 3.65E−04 |
| 1.17 | 0.61 | 5.51E−04 |
| 1.18 | 0.59 | 5.72E−04 |

TABLE 21

| Clone | KD (nM) | Kdis (1/s) |
|---|---|---|
| | a) | |
| 2.1 | 0.32 | 2.28E−04 |
| 2.13 | 0.99 | 7.43E−04 |
| 2.17 | 0.76 | 7.26E−04 |
| 2.15 | 4.72 | 3.44E−03 |
| 2.12 | 1.56 | 1.57E−03 |
| 2.22 | 2.62 | 2.44E−03 |
| | b) | |
| 1.8 | 0.85 | 6.80E−04 |
| 1.17 | 0.58 | 3.92E−04 |
| 1.27 | 0.49 | 6.45E−04 |
| | c) | |
| 1.8 | 1.95 | 1.04E−03 |
| 1.17 | 0.61 | 5.51E−04 |
| 1.27 | 0.49 | 6.45E−04 |

Single domain antibodies purified from periplasmic extracts using Ni-NTA chromatography (via the C-terminal His-tag) were also tested. Results are shown in the Table below. Binding affinities from 1-150 nM and in the low nanomolar range were detected as shown in Table 22.

TABLE 22

| clone number | KD (nM) | Kdiss (1/s) |
|---|---|---|
| 4.1 | 45 | 1.4 × 10−2 |
| 5.1 | 30 | 9.1 × 10−3 |
| 12.1 | 3.9 | 1.37E−03 |
| 10.1 | 95 | 1.85 × 10−3 |
| 11.1 | 26 | 0.00149 |
| 7.1 | 41 | 4.783 × 10−4 |
| 13.1 | 4.2 | 6 × 10−4 |
| 6.1 | 16 | 3.65 × 10−3 |
| 14.1 | 17 | 1.1 × 10−3 |

c) Measurement of Internalization of Cynomolgus PSMA-Binding $V_H$ Using Fluorescence Microvolume Assay Technology Internalization of purified $V_H$ was measured using the pH-sensitive fluorescent dye pHrodo® green. Anti-His antibody (Millipore cat. no. 05-949) was labelled with pHrodo® Green STP ester (Molecular Probes cat. no. P35369) according to the manufacturer's instructions. All samples and reagents were prepared in internalization buffer (pH 7.4) containing PBS and 0.1% Bovine Serum Albumin. CHO cells expressing cynomolgus PSMA were resuspended at $0.1\times10^6$ cells/ml and 120 nM DRAQ5 added to the cell suspension. $V_H$ (10 μl) were transferred into 384-well black clear-bottomed assay plates (Costar cat. no. 3655) and 10 μl of 40 nM pHrod® green labelled Anti-His antibody added followed by 20 μl DRAQ5 stained cells. Plates were incubated at 37° C. for 2 hr then equilibrated to room temperature. Fluorescence emission in the FL2 (502 nm-537 nm) and FL5 (677-800 nm) channels were measured on TTP Mirrorball plate reader following excitation at 488 nm and 640 nm. Data was gated on FL5 perimeter and peak intensity and the FL2 median mean fluorescence intensity of the gated data used for determination of $V_H$ internalization (FIG. 3).

Internalization of variants of single domain antibodies 1.1 and 1.2 was measured using the pH sensitive fluorescent dye pHrodo® green as described above except serially diluted $V_H$ were pre-incubated with pHrodo® green labelled Anti His antibody for 30 minutes at room temperature prior to addition of DRAQ5 stained CHO human PSMA clone 1A10 cells (20 μl). Plates were incubated for 2 hour at room temperature then fluorescent emission measured. Activity of the $V_H$ in the assay is shown in Table 23 below.

TABLE 23

| Name | pH ® RodoGreen Internalization Assay human PSMA Average $EC_{50}$ (M) |
|---|---|
| | a) |
| 1.8 | 5.0E−10 |
| 1.10 | 6.4E−10 |
| 1.11 | 3.7E−10 |
| 1.12 | 5.7E−10 |
| 1.14 | 4.4E−10 |
| 1.16 | 4.8E−10 |
| 1.17 | 2.9E−10 |
| 1.18 | 3.1E−10 |
| 2.1 | 8.0E−10 |
| 2.13 | 5.8E−10 |
| 2.17 | 8.0E−10 |
| 2.15 | 7.2E−10 |
| 2.12 | 5.3E−10 |
| 2.22 | 6.7E−10 |
| | b) |
| 1.8 | 1.2E−09 |
| 1.17 | 6.8E−10 |
| 1.27 | 3.9E−10 |

d) Measurement of Internalization of PSMA Binding $V_H$ Using the his-ZAP Assay

Internalization of His tagged PSMA binding $V_H$ was assessed using an anti-His antibody conjugated to saporin toxin (His-ZAP Advanced targeting Systems cat. No. IT52). The His-ZAP reagent binds to the $V_H$ and is internalized through the $V_H$ interaction with PSMA on the cell surface. Saporin toxin is released from the complex in the endosome and inactivates ribosomes eventually resulting in cell death.

CHO cells expressing human or cynomolgus PSMA (400 cells per well in a 30 μl volume) were seeded into 384-well black clear-bottomed tissue culture-treated assay plates (Costar cat. no. 3712) in Hams F12 (Sigma cat. no. N6658) media containing 10% foetal bovine serum, 2 mM L-glutamine, 10 μg/ml blasticidin, 300 μg/ml Zeocin, penicillin/streptomycin, 1 μg/ml tetracycline and incubated overnight in a $CO_2$ incubator at 37° C. Purified $V_H$ were serially diluted in media then an equal volume of 40 nM His-ZAP added. Following incubation for 30 minutes at 37° C. the $V_H$/His-ZAP samples (10 μl) were transferred to the cell assay plates and incubated for either 72 or 48 hours in a $CO_2$ incubator at 37° C. His-ZAP control wells (cells with His-ZAP reagent) and background controls (media only) were set up on each plate for data normalization. Cell viability was determined following either 72 or 48 hour incubation using the Cell Titer-Glo Cell Viability assay (Promega cat. no. G7571) according to the manufacturer's instructions. Relative luminescent signal (RLU) was measured using the BMG PHERAstar plate reader. The data was normalized by subtraction of the RLU signal obtained in the absence of cells and expression as a percentage of the background-corrected signal of the His-ZAP control wells. Examples are given in FIGS. 4A&B.

For LnCAP assays, cells (2000 per well in a 100 μl volume) were seeded into 96-well TC-treated plates (Costar cat. No. 3340) in RPMI 1640 media containing 10% foetal bovine serum, 2 mM L-glutamine and penicillin/streptomycin. Purified $V_H$ were serially diluted in media, then an equal volume of 60 nM His-ZAP was added. Following incubation for 30 minutes at 37° C. the $V_H$/His-ZAP samples (100 μl) were transferred to the cell assay plates and incubated for 96 hours in $CO_2$ incubator at 37° C. Cell viability was measured using the Cell Titer-Glo Cell Viability assay and data analysed as described above. Examples are given in FIG. 5.

The ability of variants of single domain antibodies 1.1 and 2.1 to internalize with a bound saporin conjugated anti His antibody, resulting in toxin mediated cell death, was determined. Assays were performed as described above except CHO human PSMA clone 1A10 cells were used for human PSMA assays and plates were incubated for 72 hours in a $CO_2$ incubator at 37° C. prior to measurement of cell viability. Activity of the single domain antibodies tested in the assay is shown in Table 24 below.

TABLE 24 a)

| | human PSMA Average $EC_{50}$ (M) | cyno PSMA $EC_{50}$ (M) |
|---|---|---|
| 1.8 | 2.6E−11 | 1.4E−09 |
| 1.10 | 2.1E−11 | 1.3E−09 |
| 1.11 | 1.4E−11 | 4.1E−10 |
| 1.12 | 1.8E−11 | 9.7E−10 |
| 1.14 | 1.7E−11 | 7.9E−10 |
| 1.16 | 1.7E−11 | 4.2E−10 |
| 1.17 | 1.5E−11 | 5.6E−10 |

TABLE 24-continued

| | | |
|---|---|---|
| 1.18 | 2.3E−11 | 4.8E−10 |
| 2.1 | 1.4E−11 | 5.2E−11 |
| 2.13 | 2.7E−11 | 8.0E−11 |
| 2.17 | 3.5E−11 | 7.0E−11 |
| 2.15 | 6.9E−11 | 1.6E−10 |
| 2.12 | 1.6E−11 | 9.1E−11 |
| 2.22 | 6.9E−11 | 1.8E−10 |

b)

| | human PSMA Average $EC_{50}$ (M) | human PSMA SD (M) |
|---|---|---|
| 1.8 | 4.0E−11 | 1.3E−11 |
| 1.17 | 2.6E−11 | 5.9E−12 |
| 1.27 | 5.2E−11 | 4.2E−11 |

c) Biparatopic molecules were tested and showed the following $EC_{50}$ values.

| | human PSMA Average $EC_{50}$ (M) | cyno PSMA Average $EC_{50}$ (M) |
|---|---|---|
| 1.1-6GS-2.1 | 1.4E−11 | 1.2E−11 |
| 1.1-6GS-2.17 | 1.2E−11 | 1.1E−11 |
| 1.1-6GS-2.15 | 1.3E−11 | 8.6E−12 |
| 1.1-6GS-2.22 | 8.8E−12 | 7.8E−12 |
| 1.16-6GS-2.1 | 1.4E−11 | 1.3E−11 |
| 1.16-6GS-2.17 | 1.5E−11 | 1.1E−11 |
| 1.16-6GS-2.15 | 1.8E−11 | 1.1E−11 |
| 1.16-6GS-2.22 | 2.0E−11 | 1.1E−11 |
| 1.11-6GS-2.1 | 1.7E−11 | 1.2E−11 |
| 1.11-6GS-2.17 | 7.9E−12 | 8.1E−12 |
| 1.11-6GS-2.15 | 1.1E−11 | 9.0E−12 |
| 1.11-6GS-2.22 | 1.0E−11 | 9.5E−12 |
| 1.18- 6GS-2.1 | 5.7E−12 | 5.8E−12 |
| 1.18-6GS-2.17 | 1.2E−11 | 5.6E−12 |
| 1.18-6GS-2.15 | 1.4E−11 | 1.0E−11 |
| 1.18-6GS-2.22 | 1.5E−11 | 1.4E−11 |
| 1.17-6GS-2.1 | 1.3E−11 | 1.5E−11 |
| 1.17-6GS-2.17 | 1.4E−11 | 1.0E−11 |
| 1.17-6GS-2.15 | 1.5E−11 | 1.2E−11 |
| 1.17-6GS-2.22 | 1.8E−11 | 1.2E−11 |

Example 9—Stability of $V_H$ $V_H$ from the different CDR3 families were tested for developability characteristics.

a) Heat Stability: HPLC Size Exclusion Chromatography

Purified $V_H$ were subjected to size exclusion chromatography. Briefly, purified $V_H$ were stored in PBS buffer for 0-14 days at either 4° C. or 40° C., and then analysed at various time points using a Waters H-Class Bio UPLC containing a PDA detector (detection at 280 nm) with separation on a Waters ACQUITY BEH 125 Å SEC column. Samples were injected in 10 μl volumes and were run in a mobile phase containing 200 mM NaCl, 100 mM sodium phosphate, pH 7.4+5% propan-1-ol at a flow rate of 0.4 ml/min. Data were collected for 6 minutes and the percentage of monomer remaining after storage as compared to that present at the start (T=0) was calculated. Parent molecules showed high stability. Variants were also tested.

Concentration of samples varied: Monovalent 1.1 variants: 5.0 mg/ml

Monovalent 2.1 variants: 3.5 mg/ml

Results are shown in the Tables below.

TABLE 25

| | % Area T0 Monomer 4° C. | | | | % Area T0 Monomer 40° C. | | | | |
|---|---|---|---|---|---|---|---|---|---|
| Name | 0 | 4 | 7 | 14 | 0 | 1 | 4 | 7 | 14 |
| 1.8 | 100.00 | 100.47 | 99.06 | 102.71 | 100.00 | 98.65 | 97.70 | 90.78 | 88.64 |
| 1.10 | 100.00 | 100.75 | 99.74 | 101.47 | 100.00 | 97.73 | 94.35 | 82.99 | 85.89 |
| 1.11 | 100.00 | 101.34 | 100.41 | 103.26 | 100.00 | 98.34 | 97.92 | 90.95 | 100.75 |
| 1.12 | 100.00 | 100.97 | 103.69 | 110.61 | 100.00 | 97.62 | 97.03 | 87.86 | 100.99 |
| 1.14 | 100.00 | 101.44 | 101.09 | 109.51 | 100.00 | 97.55 | 95.03 | 83.69 | 88.01 |
| 1.16 | 100.00 | 101.44 | 100.84 | 107.00 | 100.00 | 97.24 | 93.57 | 82.10 | 88.46 |
| 1.17 | 100.00 | 101.06 | 100.29 | 108.35 | 100.00 | 98.44 | 100.56 | 93.92 | 108.68 |
| 1.18 | 100.00 | 100.36 | 101.41 | 106.39 | 100.00 | 98.38 | 98.70 | 88.09 | 95.31 |

TABLE 26 a)

| | % Area T0 Monomer 4° C. | | | | % Area T0 Monomer 40° C. | | | | |
|---|---|---|---|---|---|---|---|---|---|
| Name | 0 | 4 | 7 | 14 | 0 | 1 | 4 | 7 | 14 |
| 2.1 | 100.00 | 100.85 | 98.69 | 101.05 | 100.00 | 99.75 | 100.07 | 100.59 | 100.55 |
| 2.13 | 100.00 | 103.11 | 100.91 | 99.78 | 100.00 | 99.80 | 99.92 | 100.30 | 100.34 |
| 2.17 | 100.00 | 101.89 | 99.62 | 99.64 | 100.00 | 100.10 | 101.00 | 101.17 | 101.50 |
| 2.15 | 100.00 | 102.20 | 99.85 | 99.20 | 100.00 | 99.46 | 100.23 | 100.28 | 101.03 |
| 2.12 | 100.00 | 100.06 | 99.56 | 99.66 | 100.00 | 99.51 | 99.92 | 100.84 | 101.71 |
| 2.22 | 100.00 | 100.76 | 99.91 | 100.48 | 100.00 | 99.12 | 99.88 | 100.23 | 102.02 |

b)

| | % Area T0 Monomer 4° C. | | | | % Area T0 Monomer 40° C. | | | | |
|---|---|---|---|---|---|---|---|---|---|
| Name | 0 | 4 | 7 | 14 | 0 | 1 | 4 | 7 | 14 |
| 1.1-6GS-2.1 | 100.00 | 109.56 | 68.16 | 68.02 | 100.00 | 105.79 | 94.77 | 64.98 | 64.58 |
| 1.1-6GS-2.17 | 100.00 | 116.15 | 75.23 | 75.20 | 100.00 | 111.31 | 101.98 | 68.73 | 63.67 |
| 1.1-6GS-2.15 | 100.00 | 111.01 | 72.93 | 73.21 | 100.00 | 106.51 | 95.09 | 70.50 | 58.28 |
| 1.1-6GS-2.22 | 100.00 | 116.88 | 80.88 | 80.66 | 100.00 | 110.00 | 105.22 | 74.44 | 75.37 |
| 1.16-6GS-2.1 | 100.00 | 135.96 | 110.01 | 110.26 | 100.00 | 101.92 | 116.20 | 106.53 | 106.74 |
| 1.16-6GS-2.17 | 100.00 | 125.26 | 106.57 | 106.10 | 100.00 | 117.55 | 110.34 | 100.59 | 96.83 |
| 1.16-6GS-2.15 | 100.00 | 136.57 | 117.42 | 118.25 | 100.00 | 121.10 | 117.79 | 107.33 | 106.12 |
| 1.16-6GS-2.22 | 100.00 | 122.20 | 105.46 | 104.15 | 100.00 | 100.32 | 104.92 | 97.31 | 93.30 |
| 1.11-6GS-2.1 | 100.00 | 76.33 | 98.05 | 97.37 | 100.00 | 96.51 | 95.53 | N/A | 98.38 |
| 1.11-6GS-2.17 | 100.00 | 45.23 | 98.17 | 97.40 | 100.00 | 96.51 | 94.72 | N/A | 90.52 |
| 1.11-6GS-2.15 | 100.00 | 101.17 | 98.87 | 98.68 | 100.00 | 97.23 | 94.78 | N/A | 87.98 |
| 1.11-6GS-2.22His | 100.00 | 102.38 | 100.84 | 99.07 | 100.00 | 98.45 | 100.47 | N/A | 82.62 |
| 1.18-6GS-2.1 | 100.00 | 102.42 | 98.53 | 97.83 | 100.00 | 92.81 | 90.11 | 85.86 | 85.82 |
| 1.18-6GS-2.17 | 100.00 | 101.18 | 97.79 | 97.30 | 100.00 | 92.66 | 87.07 | 84.42 | 79.49 |
| 1.18-6GS-2.15 | 100.00 | 100.57 | N/A | N/A | 100.00 | 88.40 | 93.87 | N/A | N/A |
| 1.18-6GS-2.22 | 100.00 | 102.69 | 97.73 | 97.54 | 100.00 | 94.07 | 91.87 | 86.53 | 100.98 |
| 1.17-6GS-2.1 | 100.00 | 101.15 | 98.97 | 97.85 | 100.00 | 97.08 | 96.59 | 95.85 | 97.40 |
| 1.17-6GS-2.17 | 100.00 | 98.88 | 98.94 | 99.34 | 100.00 | 96.16 | 95.61 | 98.86 | 92.37 |
| 1.17-6GS-2.15 | 100.00 | 97.67 | N/A | N/A | 100.00 | 99.14 | 99.77 | N/A | N/A |
| 1.17-6GS-2.22 | 100.00 | 100.20 | 97.98 | 98.47 | 100.00 | 101.00 | 102.12 | 102.52 | 100.19 |

Long term stability up to 35 days was also tested and showed a good profile.

b) Heat Stability: Mirror Ball

Purified $V_H$ samples were incubated for 0-8 days at 40° C. and then tested for binding to CHO cells expressing cynomolgus PSMA using the FMAT Direct Binding Assay as detailed in Examples 7(b) (FIGS. 6A&B).

c) Assessment of $V_H$ Serum Stability Using a Homogenous Time Resolved Fluorescence (HTRF) Assay.

Purified $V_H$ were mixed with cynomolgus monkey serum and incubated for 0-7 days at 37° C. Samples were then assessed for binding to PSMA using an HTRF assay. Briefly, PSMA (R&D Systems cat. no. 4234-ZN) was biotinylated using the Pierce EZ-Link Micro-Sulfo-NHS-LC-Biotinylation kit. (Thermo Scientific cat. no. 21935). For HTRF binding assays all samples and reagents were prepared in HTRF assay buffer containing PBS, 0.1% (w/v) BSA and 0.4M Potassium Fluoride. $V_H$ (C-terminally His-Myc tagged) were incubated with 3 nM biotinylated PSMA, 1.5 nM Streptavidin cryptate (Cisbio cat. no. 610SAKLA) and 10 nM Anti-Myc-Alexa Fluor-647 (AbD Serotec cat. no. MCA2200AF647) in a total assay volume of 10 µl in black 384-shallow-well plates (Costar cat. no. 3676) for a minimum of 3 hours at room temperature. Time-resolved fluorescent emission at 620 nm and 665 nm was measured following excitation at 337 nm on the BMG PHERAstar plate reader and the data obtained is shown in FIGS. 7A, B and C.

In another experiment, purified $V_H$ were mixed with human serum for 0-7 days at 37° C. and then assessed for binding to huPSMA CHO 1A10 cells as described in examples' 7(b) FMAT Direct cell Binding Assay. Data obtained is shown in FIG. 8 and EC50 values are shown in Tables 27 and 28 below.

TABLE 27

| VH | EC50 |
|---|---|
| 2.1 Day 0 | 2.49E−10 |
| 2.1 Day 1 | 2.54E−10 |
| 2.1 Day 4 | 2.60E−10 |
| 2.1 Day 7 | 3.01E−10 |
| 2.17 Day 0 | 2.30E−10 |
| 2.17 Day 1 | 2.10E−10 |
| 2.17 Day 4 | 2.28E−10 |
| 2.17 Day 7 | 2.38E−10 |
| 2.15 Day 0 | 2.66E−10 |
| 2.15 Day 1 | 4.97E−10 |
| 2.15 Day 4 | 3.93E−10 |
| 2.15 Day 7 | 3.76E−10 |
| 2.22 Day 0 | 3.05E−10 |
| 2.22 Day 1 | 2.91E−10 |
| 2.22 Day 4 | 3.40E−10 |
| 2.22 Day 7 | 3.28E−10 |

TABLE 28 a)

| VH | EC50 |
|---|---|
| 1.8 Day 0 | 4.09E−10 |
| 1.8 Day 1 | 4.86E−10 |
| 1.8 Day 4 | 4.96E−10 |
| 1.8 Day 7 | 5.42E−10 |
| 1.11 Day 0 | 2.34E−10 |
| 1.11 Day 1 | 2.08E−10 |
| 1.11 Day 4 | 2.27E−10 |
| 1.11 Day 7 | 2.78E−10 |
| 1.16 Day 0 | 1.65E−10 |
| 1.16 Day 1 | 2.43E−10 |
| 1.16 Day 4 | 2.42E−10 |
| 1.16 Day 7 | 2.36E−10 |
| 1.17 Day 0 | 2.73E−10 |
| 1.17 Day 1 | 2.53E−10 |
| 1.17 Day 4 | 2.59E−10 |
| 1.17 Day 7 | 2.74E−10 |
| 1.18 Day 0 | 3.04E−10 |
| 1.18 Day 1 | 3.11E−10 |
| 1.18 Day 4 | 3.19E−10 |
| 1.18 Day 7 | 3.13E−10 |

b)

| VH | EC50 |
|---|---|
| 1.8 Day 0 | 1.7E−10 |
| 1.8 Day 1 | 2.2E−10 |
| 1.8 Day 4 | 2.5E−10 |
| 1.8 Day 7 | 2.7E−10 |
| 1.17 Day 0 | 1.6E−10 |
| 1.17 Day 1 | 1.6E−10 |
| 1.17 Day 4 | 1.8E−10 |
| 1.17 Day 7 | 1.5E−10 |
| 1.27 Day 0 | 1.3E−10 |
| 1.27 Day 1 | 1.1E−10 |
| 1.27 Day 4 | 1.2E−10 |
| 1.27 Day 7 | 1.1E−10 |

c) To assess the serum stability of the different biapartopic combinations the purified biparatopic $V_H$ were mixed with human serum for 0-7 days at 37° C. and then assessed for binding to huPSMA CHO cells as described in examples 7(b) FMAT Direct cell Binding Assay. EC50 values were obtained.

| Biparatopic binding molecule | Days | EC50 |
|---|---|---|
| 1.1-6GS-2.1 | 0 | 8.02E−11 |
| | 1 | 1.03E−10 |
| | 4 | 7.86E−11 |
| | 7 | 7.88E−11 |
| 1.1-6GS-2.17 | 0 | 7.7E−11 |
| | 1 | 9.16E−11 |
| | 4 | 8.49E−11 |
| | 7 | 7.42E−11 |
| 1.11-6GS-2.1 | 0 | 8.92E−11 |
| | 1 | 6.05E−11 |
| | 4 | 7.36E−11 |
| | 7 | 8.65E−11 |
| 1.11-6GS-2.17 | 0 | 6.39E−11 |
| | 1 | 7.25E−11 |
| | 4 | 8.44E−11 |
| | 7 | 1.01E−10 |
| 1.16-6GS-2.1 | 0 | 9.02E−11 |
| | 1 | 8.60E−11 |
| | 4 | 1.00E−10 |
| | 7 | 1.07E−10 |
| 1.16-6GS-2.17 | 0 | 7.41E−11 |
| | 1 | 9.44E−11 |
| | 4 | 6.28E−11 |
| | 7 | 6.75E−11 |
| 1.17-6GS-2.1 | 0 | 5.69E−11 |
| | 1 | 4.77E−11 |
| | 4 | 4.58E−11 |
| | 7 | 5.44E−11 |
| 1.17-6GS-2.17 | 0 | 6.74E−11 |
| | 1 | 3.32E−11 |
| | 4 | 4.73E−11 |
| | 7 | 5.7E−11 |

d) Assessment of $V_H$ Thermal Stability

Differential scanning calorimetry (DSC) was conducted using a MicroCal VP-Capillary DSC (Malvern). 300 μl of protein at 0.25 mg/ml in PBS was run using a scan rate of 60° C. per minute between 10 and 90° C. Data was analysed using the MicroCal software.

Results are shown in Table 29 below.

TABLE 29

| Name | $T_m$ (° C.) | $T_{onset}$ (° C.) | $T_{1/2}$ (° C.) |
|---|---|---|---|
| a) | | | |
| 2.1 | 73.91 | 70.12 | 2.5 |
| 2.17 | 72.55 | 59.96 | 7.04 |
| 2.15 | 63.62 | 46.37 | 11.75 |
| 2.22 | 71.18 | 56.74 | 8.05 |
| 1.1 | 63.92 | 54.86 | 4.02 |
| 1.11 | 61.51 | 52.62 | 3.25 |
| 1.16 | 60.02 | 48.77 | 5.19 |
| 1.17 | 62.15 | 53.59 | 3.69 |
| 1.18 | 60.34 | 51.44 | 3.69 |
| b) | | | |
| 1.1-6GS-2.1 | 67.63 | 57.06 | 6.37 |
| 1.1-6GS-2.17 | 65.60 | 58.39 | 3.52 |
| 1.1-6GS-2.15 | 61.28 | 50.36 | 3.69 |
| 1.1-6GS-2.22 | 64.39 | 57.01 | 3.53 |
| 1.16-6GS-2.1 | 64.18 | 54.28 | 9.07 |
| 1.16-6GS-2.17 | 62.98 | 53.08 | 5.37 |
| 1.16-6GS-2.15 | 58.97 | 48.07 | 4.03 |
| 1.16-6GS-2.22 | 61.54 | 51.97 | 4.86 |
| 1.11-6GS-2.1 | 65.75 | 54.00 | 7.56 |
| 1.11-6GS-2.17 | 64.36 | 55.80 | 4.03 |
| 1.11-6GS-2.15 | 60.05 | 50.81 | 3.52 |
| 1.11-6GS-2.22 | 63.07 | 54.00 | 4.02 |
| 1.18-6GS-2.1 | 63.89 | 53.15 | 9.57 |
| 1.18-6GS-2.17 | 62.98 | 52.92 | 5.70 |
| 1.18-6GS-2.15 | 60.75 | 48.67 | 7.38 |
| 1.18-6GS-2.22 | 61.75 | 51.68 | 5.04 |
| 1.17-6GS-2.1 | 66.58 | 54.49 | 7.22 |
| 1.17-6GS-2.17 | 64.84 | 56.45 | 4.20 |
| 1.17-6GS-2.15 | 60.69 | 51.29 | 3.86 |
| 1.17-6GS-2.22 | 63.23 | 53.83 | 4.53 |

Example 10 Imaging Studies in Mice $V_H$ were injected in mice ($V_H$1.1, $V_H$2.1 and $V_H$2.1 with half-life extension). The mice contain PSMA positive (+) and PSMA negative (−) tumours. Studies were carried out as follows:

~100 MBq of Tc-99m injected activity per mouse

SPECT/CT at 5 min, 30 min, 60 min, 3 hrs, 6 hrs & 24 hrs.

images shown for different time points

Post imaging ex vivo biodistribution and autoradiography

Negative control $V_H$(αHEL4)

The half-life extended $V_H$ comprises an anti-mouse serum albumin (anti-MSA) $V_H$ with the following sequence: SEQ ID NO: 249.

The experiments show high levels of specific tumor targeting, faster penetration and greater accumulation of the injected dose to PSMA expressing (PSMA+) tumor, in particular compared to a control monoclonal IgG anti-PSMA antibody. This can be further improved by extending the half life of the $V_H$. Furthermore, the data shows quick clearance of the naked Humabody® $V_H$. The results are shown in FIGS. 9 to 15.

Example 11 Epitope Mapping

In tandem epitope mapping of PSMA binding VH against each other was carried out using Octet RED 384. $V_H$ binding was then determined from the (reference sensor subtracted) sensorgram trace using 1:1 binding models and ForteBio Octet DataAnalysis software. See also example 8b. The epitope binning results are shown in Table 30. Some clones showed partial blocking.

TABLE 30

| Group 1 | Group 2 |
|---|---|
| 3.6 | 1.4 |
| 2.1 | 12.1 |
| 11.1 | 5.1 |
| 4.1 | 13.1 |
| 7.1 | 6.1 |
| 14.1 | |
| 10.1 | |
| 9.1 | |

In a further experiment, epitope competition between single domain antibodies 1.1 and 2.1 was further characterised. PSMA was coupled onto AR2G biosensors using the amine coupling second generation kit (ForteBio) and then used for epitope binning experiments conducted using the Octet RED384. In these experiments each $V_H$ was diluted to a concentration of 4 ug/ml. Biosensors were loaded with no $V_H$ or either 2.1 or 1.1 until binding to PSMA reached saturation level. These sensors were then briefly dipped into PBS/Tween before undergoing a second association step. The second association step involved dipping biosensors into wells containing the same $V_H$ only or both 2.1 and 1.1. The presence of the first $V_H$ in the later combination ensured that it continued to saturate its PSMA binding sites. The binding profiles were then studied using the ForteBio Analysis software. These data obtained demonstrate that single domain antibodies 2.1 and 1.2 bind distinct epitopes on PSMA.

Example 12 Imaging Studies

The following constructs were tested in these studies:

VH 2.1
VH 2.1-HIS, 1.2 mg/ml
SEQ ID NO. 253
VH 1.1
VH 1.1-HIS
SEQ ID NO. 254
VH 1.1-Hel4
HEL-4-HIS
SEQ ID NO. 255
VH 2.1-VH 2.1
VH 2.1-6GS-VH 2.1 SEQ ID NO. 256
VH 2.1-VH 1.1
VH 2.1-6GS-VH 1.1 SEQ ID NO. 257

All $V_H$ domains used in this study were expressed in *E. coli*. The proteins were purified from filtered supernatant using nickel affinity chromatography and size exclusion chromatography (SEC) as described in example 7a. After buffer exchange into storage buffer, the some proteins were concentrated using spin concentrators. The protein purity was analysed using SDS-PAGE and analytical SEC. Binding to PSMA was checked using recombinant protein and/or cells expressing PSMA. Stability was checked by heating the protein to 40° C. for an extended period of time (ranging from overnight to 4 weeks) and measuring the degree of protein degradation. Aliquots of the proteins were stored at −80° C. until use.

Confocal fluorescence microscopy method to test the occurrence of co-localization between the $V_H$ of interest (in a monovalent, bivalent and biparatopic format) and the markers of endocytosis LAMP-1 (staining lysosome) and EEA-1 (staining early endosome) in a PSMA expressing cell line. An IgG benchmark antibody that binds to PSMA was used as a positive control. The results demonstrate improved internalisation of bivalent and biparatopic $V_H$ constructs.

Experimental Protocol

The cell line used was a CHO T-REx huPSMA cell line.

1) CHO T-REx huPSMA cells were induced with tetracycline for PSMA expression the day before the experiment and plated on coverslips.

2) On the following day cells were incubated with media comprising the test $V_H$ (either in their monovalent, bivalent or biparatopic format) at 500 nM or with the positive control.

3) Samples were first incubated on ice for 30 min to block endocytosis and then fixed with 4% PFA 10 min at RT, followed by 3 washes in PBS. Duplicate samples are further incubate at 37° C. for 2 hrs to trigger endocytosis, then fixed.

4) After fixation samples, were permeabilized with buffer.

5) Cells that were incubated with the positive control were stained using an anti-human-488 antibody diluted 1:2000 in 0.5% BSA/PBS+0.05% Tween for 1 hr, followed by three washes in PBS+0.05% Tween (5 min each).

6) Cells that were incubated with monovalent or bivalent/biparatopic test $V_H$ were stained using a primary anti-HIS antibody (mouse) for 1 hr, followed by washes, and then incubated with the secondary anti-mouse 488 antibody for 1 hr, followed by washes.

7) Lysosomes and endosomes are stained using a primary antibody against either the early endosome antigen 1 (EEA-1) or the lysosome membrane antigen 1 (LAMP-1) (both rabbit) for 1 hr. Cells are further incubated for 1 hr RT with anti-rabbit-647 secondary antibody, followed by washes.

8) All samples are also stained with HOECHST 1:1000 (0.5 ug/ml) for 5 min then washed. 9) Coverslips are mounted into frosty end slides and imaged using a NIKON AIR confocal system.

Pictures were taken using the program NIS-ELEMENTS AR.

Laser lines used were: 407.7 nm (HOECHST), 487.7 nm (VH/monoclonal benchmark), 639.7 (LAMP-1, EEA-1)

Objective: Apo 60× Oil λS DIC N2

For confocal mode: Pinhole Size (um): 39.6, Z step: 0.49 um.

Further imaging studies were conducted using CHO cells expressing human PSMA (15000/well) were seeded onto 96 well Poly-L-Lysine (Sigma P4707) coated plates (Perkin Elmer 6005550) in Hams F12 (Sigma N6658) media containing 10% Foetal Bovine Serum, 2 mM L-Glutamine, 10 µg/ml Blasticidin, 300 µg/ml Zeocin, penicillin/streptomycin, 1 µg/ml Tetracycline and incubated overnight in a $CO_2$ incubator at 37° C. VH were added to the plates and incubated at 4° C. for 30 minutes following by 37° C. for 2 hours. Plates were washed three times with PBS then the cells fixed in 4% paraformaldehyde and permeabilised with 0.5% saponin. Internalized VH were detected by staining with anti-His (Millipore 05-949) and anti-mouse AF488 (Jackson ImmunoResearch 115-545-098). Lysosomes were stained with LAMP-1 (Abcam Ab24170) and anti-rabbit AF647 (Jackson ImmunoResearch 111-605-008). Nuclei were stained using Hoescht stain (Life technologies H3570). Plates were imaged using the IN Cell Analyzer 6000 and Images processed using ImageJ software.

Example 13 Potency of MMAE Toxin Conjugated to Immunoconjugates In Vitro

The ability of MMAE-toxin-conjugated $V_H$ to internalize into PSMA-expressing cells resulting in cell killing was determined using an in vitro cytotoxicity assay. Human cells (DU-145, ATCC HTB-81) stably expressing human PSMA or matched PSMA negative cells were seeded into 384-well black clear-bottomed tissue culture treated assay plates at 3000 cells per well in RPMI 1640 medium containing 10% foetal bovine serum, 2 mM L-Glutamine, 1× penicillin/streptomycin, and incubated overnight in a $CO_2$ incubator at 37° C. Cells were then incubated with serially-diluted MMAE-toxin-conjugated $V_H$ for 48 or 72 hours. Untreated control wells (cells in the absence of toxin-conjugated $V_H$) and background control wells (media only) were set up on each plate for data normalization. Cell killing was determined following the incubation using the Cell Titer-Glo Cell Viability assay (Promega G7571) according to the manufacturer's instructions. Relative luminescent signal (RLU) was measured using the BMG PHERAstar plate reader. The data was normalized by subtraction of the RLU signal obtained in the background control wells then expressed as a % of the untreated control wells (% survival). FIG. 16 illustrates dose response curves obtained using a human-PSMA-expressing human cell line and the matched parent (i.e. non-transfected) PSMA negative cell line in a representative experiment (48 hour incubation). $IC_{50}$ values and maximum % cell killing obtained for the MMAE-conjugated constructs are summarized in Table 31. Crescendo's Humabody® $V_H$ were conjugated to MMAE using HiPEG™ technology (WO 2009/047500; Cong et al., (2012) Bioconjugate Chem. 2012, 23, 248-263); the positive ADC control was generated using ThioBridge™ technology (WO 2016063006; WO 2005/007197; Balan et al., (2007) Bioconjugate Chem., 18, 61-76). The anti-PSMA-MMAE-conjugated $V_H$ specifically killed PSMA positive cells with minimal cell killing observed for the PSMA negative control cell line. The biparatopics that consist of two $V_H$ targeting different epitopes of the PSMA were more potent than the monovalent or bivalent PSMA $V_H$ constructs. The DU145 assay was performed with a 48 h and with a 72 h HDC incubation. This had an impact on the $IC_{50}$ values measured and the % maximum kill, but was not expected to affect the ranking of the different HDC formats. For screening, a 48 h incubation was preferred for higher throughput. Using the 48 h incubation none of the constructs tested reached 100% cell kill (even at the highest concentrations tested). The maximum response leveled off at approx. 70-85% (see Table 31). Table 31 shows the IC50 values and FIG. 17 illustrates the higher maximum % cell killing observed using a 72 hour incubation time (n=1 data).

TABLE 31

Summary of in vitro cytotoxicity data obtained with the human-PSMA-expressing human cell line following a 48 hour incubation.

| Construct | | | DAR | Mean $IC_{50}$ ± SD (nM), Mean Max % Cell kill, (n number) | $IC_{50}$ Toxin (nM) |
|---|---|---|---|---|---|
| HiPEG ™ A-$His_6$ val-cit-PAB-MMAE | Monovalent | 2.1-myc-his | 1 | 1.2 ± 0.7 nM Max cell kill 74% (n = 4) | 1.16 |
| HiPEG ™ B-$His_6$ val-cit-PAB-MMAE | Monovalent | 1.1-myc-his | 0.9 | 2.7 ± 2.5 nM Max cell kill 73% (n = 4) | 2.43 |
| HiPEG ™ C-$His_6$ val-cit-PAB-MMAE | Monovalent | 3.1-myc-his | 1 | 5.2 ± 2.6 nM Max cell kill 59% (n = 4) | 5.21 |
| HiPEG ™ D-$His_6$ val-cit-PAB-MMAE | Monovalent | HEL4-his | | >300 nM (n = 3) | |
| HiPEG ™ A-2-A-$His_6$ val-cit-PAB-MMAE | Bivalent | 2.1-(G4S)6-2.1 | 1 | 0.32 ± 0.2 nM Max cell kill 57% (n = 3) | 0.32 |
| HiPEG ™ B-2-B-$His_6$ val-cit-PAB-MMAE | Bivalent | 1.1-(G4S)6-1.1 | 0.7 | 18 ± 8 nM (n = 3) Max cell kill 80% (Estimated) | 12.6 |

TABLE 31-continued

Summary of in vitro cytotoxicity data obtained with the human-PSMA-expressing human cell line following a 48 hour incubation.

| Construct | | | DAR | Mean $IC_{50}$ ± SD (nM), Mean Max % Cell kill, (n number) | $IC_{50}$ Toxin (nM) |
|---|---|---|---|---|---|
| HiPEG ™ C-2-C-$His_6$ val-cit-PAB-MMAE | Bivalent | 3.1-(G4S)6-3.1 | 1 | 4.5 ± 2.4 nM Max cell kill 69% (n = 3) | 4.54 |
| HiPEG ™ A-1-B-$His_6$ val-cit-PAB-MMAE | Biparatopic | 2.1-(G4S)2-1.1 | 1 | 0.67 ± 0.3 nM Max cell kill 75% (n = 4) | 0.67 |
| HiPEG ™ A-2-B-$His_6$ val-cit-PAB-MMAE | Biparatopic | 2.1-(G4S)6-1.1 | 1 | 0.37 ± 0.1 nM Max cell kill 78% (n = 3) | 0.37 |
| HiPEG ™ B-1-A-$His_6$ val-cit-PAB-MMAE | Biparatopic | 1.1-(G4S)2-2.1 | 1 | 0.13 ± 0.1 nM Max cell kill 79% (n = 3) | 0.13 |
| HiPEG ™ B-2-A-$His_6$ val-cit-PAB-MMAE | Biparatopic | 1.1-(G4S)6-2.1 | 1 | 0.15 ± 0.1 nM Max cell kill 79% (n = 3) | 0.15 |
| ThioBridge ™ anti-PSMA val-cit-PAB-MMAE | Control ADC | control ADC | 4 | 0.03 ± 0.02 nM Max cell kill 82% (n = 3) | 0.13 |

TABLE 32

Summary of in vitro cytotoxicity data obtained with the human-PSMA-expressing human cell line following a 72 hour incubation.

| Construct | Format | VH | DAR | $IC_{50}$ (nM) | $IC_{50}$ (toxin) nM |
|---|---|---|---|---|---|
| HiPEG ™ A-$His_6$ val-cit-PAB-MMAE | monovalent | 2.1-myc-his | 1 | 0.55 | 0.55 |
| HiPEG ™ B-$His_6$ val-cit-PAB-MMAE | monovalent | 1.1-myc-his | 0.9 | 4.1 | 3.69 |
| HiPEG ™ A-2-A-$His_6$ val-cit-PAB-MMAE | bivalent | 2.1-(G4S)6-2.1 | 1 | 0.19 | 0.19 |
| HiPEG ™ B-2-B-$His_6$ val-cit-PAB-MMAE | bivalent | 1.1-(G4S)6-1.1 | 0.7 | 21 | 14.7 |
| HiPEG ™ A-2-B-$His_6$ val-cit-PAB-MMAE | biparatopic | 2.1-(G4S)6-1.1 | 1 | 0.29 | 0.29 |
| HiPEG ™ B-1-A-$His_6$ val-cit-PAB-MMAE | biparatopic | 1.1-(G4S)2-2.1 | 1 | 0.1 | 0.1 |
| ThioBridge ™ anti-PSMA val-cit-PAB-MMAE | mAb | Control ADC | 4 | 0.042 | 0.168 |

The order of potency observed for the monovalent constructs was $V_H$2.1>$V_H$1.1>$V_H$3.1.

Procedure for the Preparation of Humabody™ Drug Conjugates (HDCs)

A stock solution of conjugation reagent, HiPEG™ val-cit-PAB-MMAE (FIG. 18), was prepared in MeCN prior to performing conjugation reactions. A solution of Humabody™ (0.9 mg/mL in PBS; 20 mM EDTA, pH 7.5) was mixed gently with HiPEG™ val-cit-PAB-MMAE reagent (1.5 equiv. per Humabody™; 5% (v/v) final MeCN concentration) and incubated at 22° C. for 19 h. After 19 h, the conjugation reaction was mixed with an equal volume of 600 mM sodium phosphate buffer (150 mM NaCl; 20 mM EDTA), pH 7.5 and cooled to 4° C. A stock solution of 1 mg/mL $NaBH_4$ solution was prepared in 0.1 M NaOH. Two aliquots each of $NaBH_4$ solution, (10 equiv. per reagent), were added to the cooled conjugation reaction with a 30 min interval between additions. After a further 30 min interval, the crude mixture was purified by hydrophobic interaction chromatography (HIC) using a TOSOH ToyoPearl Phenyl-650S column. The sample was bound and washed onto the column using 50 mM sodium phosphate (2 M NaCl), pH 7 (buffer A) and eluted using a gradient of 50 mM sodium phosphate (20% v/v isopropanol), pH 7 (buffer B). Fractions containing the mono-loaded product were pooled and concentrated using Vivaspin20 concentrators fitted with 5 kDa MWCO PES membranes. The concentrated fractions were buffer exchanged into DPBS using PD10 columns and the buffer exchanged material sterile filtered using 0.2 μm PVDF syringe filtration unit.

The HiPEG val-cit-PAB-MMAE moiety is attached via a C terminal His6-tag on a $V_H$. Two histidines are needed for attachment of each "payload" toxin molecule. Humabody $V_H$, DAR=1 species were purified for use in cytotoxicity studies, in some instances an exact DAR of 1 was not achieved (see table below). In the examples herein a single MMAE moiety was attached, but multiple payloads are possible (DARs>1).

Procedure for the Preparation of Control ADC with Drug: Antibody Ratio (DAR) of 3.5

Positive control antibody Pro_006 is an anti-PSMA antibody composed of heavy and light chain sequences described within U.S. Pat. No. 8,470,330 and exemplified as antibody 006.

Conjugation 1:

A solution of mAb Pro_006 (5.07 mg/mL) in reaction buffer (20 mM sodium phosphate, 150 mM NaCl; 20 mM EDTA, pH 7.5), was warmed to 40° C. for 15 min. TCEP (5 mM, 2 equiv. per mAb) was added to the mAb solution, mixed gently and incubated at 40° C. for 1 h. A stock solution of conjugation reagent, mc-val-cit-PAB-MMAE (FIG. 19) was prepared in DMF at 2.8 mM. The reduced mAb was cooled to 22° C., diluted to 4.2 mg/mL with reaction buffer and mc-val-cit-PAB-MMAE (5.25 equiv. per mAb) was added. The conjugation mixture was incubated at 22° C. for 2 h. The crude conjugation mixture was treated with 50 mM N-acetyl-L-cysteine (20 equiv. over reagent) at 22° C. for 30 min. The reaction mixture was diafiltered against DPBS using a Vivaspin20 concentrator fitted with 30 kDa MWCO PES membranes. The diafiltered ADC solution was buffer exchanged into DPBS using a Centripure P50 column. The DAR of the sample was assessed by HIC (average DAR=3.21).

Conjugation 2:

A solution of mAb Pro_006 (5.07 mg/mL) in reaction buffer (20 mM sodium phosphate 150 mM NaCl; 20 mM EDTA), pH 7.5 was warmed to 40° C. for 15 min. TCEP (5 mM, 2.75 equiv. per mAb) was added to the mAb solution, mixed gently and incubated at 40° C. for 1 h. A stock solution of conjugation reagent, mc-val-cit-PAB-MMAE (FIG. 19) was prepared in DMF at 4.0 mM. The reduced mAb was cooled to 22° C., diluted to 4.2 mg/mL with reaction buffer and mc-val-cit-PAB-MMAE (7 equiv. per mAb) was added. The conjugation mixture was incubated at 22° C. for 2 h. The crude conjugation mixture was treated with 50 mM N-acetyl-L-cysteine (20 equiv. over reagent) at 22° C. for 30 min. The reaction mixture was diafiltered against DPBS using a Vivaspin20 concentrator fitted with 30 kDa MWCO PES membranes. The diafiltered ADC solution was buffer exchanged into DPBS using a Centripure P50 column. The DAR of the sample was assessed by HIC (average DAR=4.52).

Production of average DAR 3.5 ADC: ADC 1 (DAR 3.21) and ADC 2 (DAR 4.52) were mixed in a 4:1 mol ratio to prepare an ADC with intermediate DAR. The resulting sample was sterile filtered using 0.2 μm PVDF syringe filtration unit. The DAR of the sample was assessed by HIC (average DAR=3.45).

In Vitro Potency of Half-Life Extended HDCs

The in vitro potency of half-life extended HDCs was assessed using the DU145 cell killing assay (72 h).

This material described in Table 34 was generated to test the effect of adding a half-life extension moiety to the HDCs. Half-life-extended versions (HLE) were generated using the MSA-binding $V_H$ (SEQ ID No. 528). In vitro potency was assessed using the DU145 cell killing assay (72 h).

TABLE 34

$IC_{50}$ values PSMA-DU145 cytotoxicity assay (72 h):

| Format | VH | Name | DAR | $IC_{50}$ (nM) | $IC_{50}$ (toxin) (nM) | Average Max Cell Kill % |
|---|---|---|---|---|---|---|
| Monovalent | HEL4 | HiPEG ™ HEL4-His val-cit-PAB-MMAE | 1 | >100 | >100 | |
| Biparatopic | 1.1-6GS-2.1 | HiPEG ™ 1.1-6GS-2.1-His val-cit-PAB-MMAE | 1 | 0.27 | 0.27 | 86 |
| Biparatopic-HLE | 1.1-6GS-2.1-6GS-half life extension | HiPEG ™ 1.1-6GS-2.1-6GS- half life extension -His val-cit-PAB-MMAE | 1 | 0.82 | 0.82 | 82 |
| Monovalent-HLE | HEL4-6GS-half life extension | HiPEG ™ HEL4-6GS- half life extension -His val-cit-PAB-MMAE | 1 | >100 | >100 | |
| mAb | Control PSMA mAb-MMAE | Pro_006-mc-val-cit-PAB-MMAE | 3.5 | 0.061 | 0.2135 | 89 |

The invention claimed is:

1. A binding molecule capable of binding human PSMA comprising a single human variable heavy chain domain ($V_H$) antibody selected from the group consisting of:

a single $V_H$ domain antibody, comprising a CDR1 sequence comprising SEQ ID NO: 1, a CDR2 sequence comprising SEQ ID NO: 2 and a CDR3 sequence comprising SEQ ID NO: 3;

a single $V_H$ domain antibody comprising a CDR1 sequence comprising SEQ ID NO: 5, a CDR2 sequence comprising SEQ ID NO: 6 and a CDR3 sequence comprising SEQ ID NO: 7;

a single $V_H$ domain antibody comprising a CDR1 sequence comprising SEQ ID NO: 9, a CDR2 sequence comprising SEQ ID NO: 10 and a CDR3 sequence comprising SEQ ID NO: 11;

a single $V_H$ domain antibody, comprising a CDR1 sequence comprising SEQ ID NO: 13, a CDR2 sequence comprising SEQ ID NO: 14 and a CDR3 sequence comprising SEQ ID NO: 15;

a single $V_H$ domain antibody comprising a CDR1 sequence comprising SEQ ID NO: 17, a CDR2 sequence comprising SEQ ID NO: 18 and a CDR3 sequence comprising SEQ ID NO: 19;

a single $V_H$ domain antibody comprising a CDR1 sequence comprising SEQ ID NO: 21, a CDR2 sequence comprising SEQ ID NO: 22 and a CDR3 sequence comprising SEQ ID NO: 23;

a single $V_H$ domain antibody, comprising a CDR1 sequence comprising SEQ ID NO: 25, a CDR2 sequence comprising SEQ ID NO: 26 and a CDR3 sequence comprising SEQ ID NO: 27;

a single $V_H$ domain antibody comprising a CDR1 sequence comprising SEQ ID NO: 29, a CDR2 sequence comprising SEQ ID NO: 30 and a CDR3 sequence comprising SEQ ID NO: 31;

a single $V_H$ domain antibody comprising a CDR1 sequence comprising SEQ ID NO: 33, a CDR2 sequence comprising SEQ ID NO: 34 and a CDR3 sequence comprising SEQ ID NO: 35; and a single $V_H$ domain antibody comprising a CDR1 sequence comprising SEQ ID NO: 37, a CDR2 sequence comprising SEQ ID NO: 38 and a CDR3 sequence comprising SEQ ID NO: 39.

2. The binding molecule according to claim 1 wherein said single $V_H$ domain antibody comprises a sequence selected from SEQ ID Nos: 4, 8, 12, 16, 20, 24, 28, 32, 36 and 40.

3. A binding molecule comprising a first single human heavy chain variable immunoglobulin ($V_H$) domain antibody capable of binding human PSMA and a second single $V_H$ domain antibody capable of binding human PSMA, wherein said first single human heavy chain variable immunoglobulin ($V_H$) domain antibody capable of binding human PSMA is according to claim 1.

4. The binding molecule according to claim 3 wherein said first single human heavy chain variable immunoglobulin ($V_H$) domain antibody and said second single $V_H$ domain antibody bind to the same epitope on human PSMA.

5. The binding molecule according to claim 3 wherein said first single human heavy chain variable immunoglobulin ($V_H$) domain antibody binds to a first epitope on PSMA and said second single $V_H$ domain antibody binds to a second epitope on PSMA wherein said first and said second epitope are not identical.

6. The binding molecule according to claim 5 wherein said second single $V_H$ domain antibody is selected from the group consisting of SEQ ID Nos: 71-95.

7. The binding molecule according to claim 3 wherein the first single human heavy chain variable immunoglobulin ($V_H$) domain antibody is located C or N terminally.

8. The binding molecule according to claim 3 wherein said first single human heavy chain variable immunoglobulin ($V_H$) domain antibody and said second single $V_H$ domain antibody are covalently linked by a peptide linker.

9. The binding molecule according to claim 8 wherein the peptide linker is between 3 and 50 amino acids long.

10. The binding molecule according to claim 8 wherein the peptide linker comprises glycine and serine amino acid residues.

11. The binding molecule according to claim 1 wherein said binding molecule is conjugated to a toxin, enzyme, radioisotope or other chemical moiety.

12. A pharmaceutical composition comprising the binding molecule according to claim 1 and a pharmaceutical carrier.

13. A method for treating prostate cancer or a prostatic disorder comprising administering a therapeutically-effective amount of the binding molecule according to claim 1.

14. An in vivo or in vitro method for reducing human PSMA activity comprising contacting human PSMA with the binding molecule according to claim 1.

15. A method for determining the presence of PSMA in a test sample by an immunoassay comprising contacting said sample with the binding molecule according to claim 1 and at least one detectable label.

16. An isolated nucleic acid molecule comprising a nucleotide sequence encoding the binding molecule according to claim 1.

17. A construct or host cell comprising the nucleic acid according to claim 16.

18. A method for producing the binding molecule according to claim 1 comprising expressing a nucleic acid encoding said binding molecule in a host cell and isolating the binding molecule from the host cell culture.

19. A kit comprising the binding molecule according to claim 1 or the pharmaceutical composition according to claim 12.

20. A multispecific binding molecule comprising the binding molecule according to claim 1.

21. The binding molecule according to claim 1 wherein said binding molecule is capable of being internalised by a cell.

22. An immunoconjugate conjugate comprising the binding molecule according to claim 1.

* * * * *

UNITED STATES PATENT AND TRADEMARK OFFICE

CERTIFICATE OF CORRECTION

PATENT NO. : 11,401,342 B2
APPLICATION NO. : 16/627968
DATED : August 2, 2022
INVENTOR(S) : Royle et al.

It is certified that error appears in the above-identified patent and that said Letters Patent is hereby corrected as shown below:

On the Title Page

(30) Foreign Application Priority Data: Please correct "1711068" to read --1711068.5--

In the Specification

Column 1, Lines 20-21: Please remove the paragraph break between "relapse." and "Whilst"

Column 4, Line 2: Please correct "• 3.1" to read --▪ 3.1--

Column 4, Line 5: Please correct "• 1.10" to read --▪ 1.10--

Column 4, Line 5: Please correct "○ 01.14" to read --○ 1.14--

Column 4, Lines 24-25: Please remove the paragraph break between "B." and "$V_H$ 1.1."

Column 7, Lines 43-44: Please remove the paragraph break between "-FR4." and "Thus,"

Column 8, Lines 56-57: Please remove the paragraph break between "below." and "Thus,"

Column 9, Lines 40-41: Please remove the paragraph break between "domain." and "Thus,"

Column 14, Lines 18-19: Please remove the paragraph break between "FR4." and "In one"

Column 15, Line 26: Please correct "(c) through (I)" to read --(c) through (l)--

Column 45, Line 2: Please insert a paragraph break between "washed." and "9)"

Signed and Sealed this
Twenty-second Day of November, 2022

Katherine Kelly Vidal
*Director of the United States Patent and Trademark Office*

In the Claims

Column 215, Line 40, Claim 1: Please correct “antibody, comprising” to read --antibody comprising--

Column 215, Line 52, Claim 1: Please correct “antibody, comprising” to read --antibody comprising--

Column 215, Line 64, Claim 1: Please correct “antibody, comprising” to read --antibody comprising--

Column 218, Line 23, Claim 22: Please correct “immunoconjugate conjugate comprising” to read --immunoconjugate comprising--